US008703387B2

(12) United States Patent
Kawaue et al.

(10) Patent No.: US 8,703,387 B2
(45) Date of Patent: Apr. 22, 2014

(54) RESIST COMPOSITION, METHOD OF FORMING RESIST PATTERN, NOVEL COMPOUND, AND ACID GENERATOR

(75) Inventors: Akiya Kawaue, Kawasaki (JP); Yoshiyuki Utsumi, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 0 days.

(21) Appl. No.: 13/478,390

(22) Filed: May 23, 2012

(65) Prior Publication Data

US 2012/0301829 A1 Nov. 29, 2012

(30) Foreign Application Priority Data

May 25, 2011 (JP) ................................. 2011-117366

(51) Int. Cl.

| | |
|---|---|
| ***G03F 1/00*** | (2012.01) |
| ***G03F 7/00*** | (2006.01) |
| ***C07C 309/25*** | (2006.01) |
| ***C07C 317/04*** | (2006.01) |
| ***C07D 327/10*** | (2006.01) |

(52) U.S. Cl.

USPC .......... 430/270.1; 430/914; 430/921; 549/10; 549/31; 562/30; 562/100

(58) Field of Classification Search

USPC ....................................... 430/270.1, 914, 921

See application file for complete search history.

(56) References Cited

U.S. PATENT DOCUMENTS

| | | | | |
|---|---|---|---|---|
| 5,945,517 | A | 8/1999 | Nitta et al. | |
| 6,153,733 | A | 11/2000 | Yukawa et al. | |
| 6,949,325 | B2 | 9/2005 | Li et al. | |
| 7,074,543 | B2 | 7/2006 | Iwai et al. | |
| 7,579,497 | B2 | 8/2009 | Harada et al. | |
| 2001/0049073 | A1 | 12/2001 | Hada et al. | |
| 2008/0187860 | A1 | 8/2008 | Tsubaki et al. | |
| 2009/0130597 | A1 * | 5/2009 | Seshimo et al. | 430/285.1 |
| 2010/0121077 | A1 * | 5/2010 | Seshimo et al. | 549/31 |

FOREIGN PATENT DOCUMENTS

| | | |
|---|---|---|
| JP | A-09-208554 | 8/1997 |
| JP | A-11-035551 | 2/1999 |
| JP | A-11-035552 | 2/1999 |
| JP | A-11-035573 | 2/1999 |
| JP | A-11-322707 | 11/1999 |
| JP | A-2000-206694 | 7/2000 |
| JP | A-2003-241385 | 8/2003 |
| JP | A-2005-037888 | 2/2005 |
| JP | A-2005-336452 | 12/2005 |
| JP | A-2006-259582 | 9/2006 |
| JP | A-2006-317803 | 11/2006 |
| JP | A-2008-292975 | 12/2008 |
| JP | A-2010-039146 | 2/2010 |
| WO | WO 2004/074242 A2 | 9/2004 |

* cited by examiner

*Primary Examiner* — Cynthia H Kelly
*Assistant Examiner* — Anna Conlin
(74) *Attorney, Agent, or Firm* — Knobbe Martens Olson & Bear LLP

(57) ABSTRACT

A resist composition comprising a base component (A) which exhibits changed solubility in a developing solution under action of acid and an acid-generator component (B) which generates acid upon exposure, the acid-generator component (B) comprising an acid generator (B1) composed of a compound represented by general formula (b1-1) shown below [wherein, X represents a cyclic group of 3 to 30 carbon atoms which may have a substituent, provided that a ring skelton of the cyclic group contains an $—SO_2—$ bond or an $—O—SO_2—$ bond, and at least one carbon atom which is not adjacent to the $—SO_2—$ bond or the $—O—SO_2—$ bond has an oxygen atom as a substituent; $Q^1$ represents a divalent linking group or a single bond; $Y^1$ represents an alkylene group which may have a substituent or a fluorinated alkylene group which may have a substituent; and $A^+$ represents an organic cation].

[Chemical Formula 1]

$$X\text{-}Q^1\text{-}Y^1—SO_3^{\ominus}A^{\oplus} \quad (b1\text{-}1)$$

7 Claims, No Drawings

RESIST COMPOSITION, METHOD OF FORMING RESIST PATTERN, NOVEL COMPOUND, AND ACID GENERATOR

TECHNICAL FIELD

The present invention relates to a resist composition exhibiting excellent lithography properties and excellent pattern shape, a method of forming a resist pattern using the resist composition, and a new compound as an acid generator for the resist composition, and an acid generator.

Priority is claimed on Japanese Patent Application No. 2011-117366, filed May 25, 2011, the content of which is incorporated herein by reference.

DESCRIPTION OF RELATED ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter (energy higher) than these excimer lasers, such as electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified resist composition is used, which includes a base material component that exhibits a changed solubility in a developing solution under the action of acid and an acid-generator component that generates acid upon exposure.

For example, in the case where the developing solution is an alkali developing solution (alkali developing process), a chemically amplified positive resist which contains, as a base component (base resin), a resin which exhibits increased solubility in an alkali developing solution under action of acid, and an acid generator is typically used. If the resist film formed using the resist composition is selectively exposed during formation of a resist pattern, then within the exposed portions, acid is generated from the acid-generator component, and the action of this acid causes an increase in the solubility of the resin component in an alkali developing solution, making the exposed portions soluble in the alkali developing solution. In this manner, the unexposed portions remain to form a positive resist pattern. The base resin used exhibits increased polarity by the action of acid, thereby exhibiting increased solubility in an alkali developing solution, whereas the solubility in an organic solvent is decreased. Therefore, when such a base resin is applied to a process using a developing solution containing an organic solvent (organic developing solution) (hereafter, this process is referred to as “solvent developing process” or “negative tone-developing process”) instead of an alkali developing process, the solubility of the exposed portions in an organic developing solution is decreased. As a result, in the solvent developing process, the unexposed portions of the resist film are dissolved and removed by the organic developing solution, and a negative resist pattern in which the exposed portions are remaining is formed. The negative tone-developing process is proposed, for example, in Patent Document 1.

Currently, resins that contain structural units derived from (meth)acrylate esters within the main chain (acrylic resins) are now widely used as base resins for resist compositions that use ArF excimer laser lithography, as they exhibit excellent transparency in the vicinity of 193 nm (for example, see Patent Document 2).

On the other hand, as acid generators usable in a chemically amplified resist composition, various types have been proposed including, for example, onium salt acid generators; oxime sulfonate acid generators; diazomethane acid generators; nitrobenzylsulfonate acid generators; iminosulfonate acid generators; and disulfone acid generators. Among these, as the onium salt acid generators, iodonium salts having an iodonium ion as the cation or sulfonium salts having a sulfonium ion as the cation have been conventionally used. As the anion moiety (acid) that forms a salt with the cation, a fluorinated alkylsulfonate ion is typically used (for example, see Patent Document 3).

Further, there have been proposed resist compositions containing a sulfonium compound or a iodonium compound as an acid generator which has a lactone-containing cyclic group having —C(═O)—O— in the ring structure in the anion moiety (for example, see Patent Documents 4 and 5).

DOCUMENTS OF RELATED ART

Patent Document

[Patent Document 1] Japanese Unexamined Patent Application, First Publication No. 2008-292975

[Patent Document 2] Japanese Unexamined Patent Application, First Publication No. 2003-241385

[Patent Document 3] Japanese Unexamined Patent Application, First Publication No. 2005-037888

[Patent Document 4] U.S. Pat. No. 7,579,497

[Patent Document 5] Japanese Unexamined Patent Application, First Publication No. 2010-39146

SUMMARY OF THE INVENTION

As further progress is made in lithography techniques and miniaturization of resist patterns, further improvement in resist materials has been demanded in terms of various lithography properties such as LWR, EL margin, and MEF and resist pattern shape.

However, when conventional acid generators as those disclosed in Patent Documents 3 to 5 were used, there was still room for improvement in lithography properties and resist pattern shape.

The present invention takes the above circumstances into consideration, with an object of providing a resist composition, a method of forming a resist pattern using the same, a novel compound useful as an acid generator for a resist composition, and an acid generator.

For solving the above-mentioned problems, the present invention employs the following aspects.

Specifically, a first aspect of the present invention is a resist composition including a base component (A) which exhibits changed solubility in a developing solution under action of acid and an acid-generator component (B) which generates acid upon exposure, the acid-generator component (B) including an acid generator (B1) represented by general formula (b1-1) shown below.

[Chemical Formula 1]

$$X\text{-}Q^1\text{-}Y^1\text{—}SO_3^{\ominus}A^{\oplus} \quad \text{(b1-1)}$$

wherein, X represents a cyclic group of 3 to 30 carbon atoms which may have a substituent, provided that a ring skelton of the cyclic group contains an $—SO_2—$ bond or an $—O—SO_2—$ bond, and at least one carbon atom which is not adjacent to the $—SO_2—$ bond or the $—O—SO_2—$ bond has an oxygen atom as a substituent; $Q^1$ represents a divalent linking group or a single bond; $Y^1$ represents an alkylene group which may have a substituent or a fluorinated alkylene group which may have a substituent; and $A^+$ represents an organic cation.

A second aspect of the present invention is a method of forming a resist pattern, including: using a resist composition of the first aspect to form a resist film on a substrate; conducting exposure of the resist film; and developing the resist film to form a resist pattern.

A third aspect of the present invention is a compound represented by general formula (b1-1) shown below.

[Chemical Formula 2]

$$X\text{-}Q^1\text{-}Y^1\text{—}SO_3^{\ominus}A^{\oplus} \quad \text{(b1-1)}$$

wherein, X represents a cyclic group of 3 to 30 carbon atoms which may have a substituent, provided that a ring skelton of the cyclic group contains an $—SO_2—$ bond or an $—O—SO_2—$ bond, and at least one carbon atom which is not adjacent to the $—SO_2—$ bond or the $—O—SO_2—$ bond has an oxygen atom as a substituent; $Q^1$ represents a divalent linking group or a single bond; $Y^1$ represents an alkylene group which may have a substituent or a fluorinated alkylene group which may have a substituent; and $A^+$ represents an organic cation.

A fourth aspect of the present invention is an acid generator including the compound of the third aspect.

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified.

The term "alkylene group" includes linear, branched or cyclic, divalent saturated hydrocarbon, unless otherwise specified. The same applies for the alkyl group within an alkoxy group.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with fluorine atom(s).

The term "structural unit" refers to a monomer unit that contributes to the formation of a polymeric compound (resin, polymer, copolymer).

An "acrylate ester" refers to a compound in which the terminal hydrogen atom of the carboxy group of acrylic acid ($CH_2{=}CH—COOH$) has been substituted with an organic group.

A "structural unit derived from an acrylate ester" refers to a structural unit that is formed by the cleavage of the ethylenic double bond of an acrylate ester.

Examples of the substituent bonded to the carbon atom on the α-position in the "acrylate ester which may have the hydrogen atom bonded to the carbon atom on the α-position substituted with a substituent" include a halogen atom, an alkyl group of 1 to 5 carbon atoms, a halogenated alkyl group of 1 to 5 carbon atoms and a hydroxyalkyl group. With respect to the "structural unit derived from an acrylate ester", the "α-position (the carbon atom on the α-position)" refers to the carbon atom having the carbonyl group bonded thereto, unless specified otherwise.

Examples of the halogen atom as the substituent which may be bonded to the carbon atom on the α-position include a fluorine atom, a chlorine atom, a bromine atom and an iodine atom.

Specific examples of the alkyl group of 1 to 5 carbon atoms for the substituent which may be bonded to the carbon atom on the α-position include linear or branched alkyl groups such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group of 1 to 5 carbon atoms for the substituent include groups in which part or all of the hydrogen atoms of the aforementioned "alkyl group of 1 to 5 carbon atoms for the substituent" are substituted with halogen atoms. Examples of the halogen atom include a fluorine atom, a chlorine atom, a bromine atom and an iodine atom, and a fluorine atom is particularly desirable.

Specific examples of the hydroxyalkyl group of 1 to 5 carbon atoms for the substituent include groups in which part or all of the hydrogen atoms of the aforementioned "alkyl group of 1 to 5 carbon atoms for the substituent" are substituted with hydroxy groups.

In the present invention, it is preferable that a hydrogen atom, an alkyl group of 1 to 5 carbon atoms or a halogenated alkyl group of 1 to 5 carbon atoms is bonded to the carbon atom on the α-position, a hydrogen atom, an alkyl group of 1 to 5 carbon atoms or a fluorinated alkyl group of 1 to 5 carbon atoms is more preferable, and in terms of industrial availability, a hydrogen atom or a methyl group is the most desirable.

The term "exposure" is used as a general concept that includes irradiation with any form of radiation.

The present invention relates to a resist composition exhibiting excellent pattern shape and excellent lithography properties, a method of forming a resist pattern using the resist composition, and a new compound as an acid generator for a resist composition, and an acid generator.

DETAILED DESCRIPTION OF THE INVENTION

<<Resist Composition>>

The resist composition according to the first aspect of the present invention includes a base component (A) which exhibits changed solubility in a developing solution under action of acid (hereafter, referred to as "component (A)") and an acid-generator component (B) which generates acid upon exposure (hereafter, referred to as "component (B)").

With respect to a resist film formed using the resist composition, when a selective exposure is conducted during formation of a resist pattern, acid is generated from the component (B), and the generated acid acts on the component (A) to change the solubility of the component (A) in a developing solution. As a result, the solubility of the exposed portions in a developing solution is changed, whereas the solubility of the unexposed portions in a developing solution remains unchanged. Therefore, the exposed portions are dissolved and removed by developing in the case of a positive pattern, whereas unexposed portions are dissolved and removed in the case of a negative pattern, and hence, a resist pattern can be formed.

The resist composition of the present invention may be either a negative resist composition or a positive resist composition.

In the present specification, a resist composition which forms a positive pattern by dissolving and removing the exposed portions is called a positive resist composition, and a resist composition which forms a negative pattern by dissolving and removing the unexposed portions is called a negative resist composition.

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The "organic compound having a molecular weight of 500 or more" which can be used as a base component is broadly classified into non-polymers and polymers.

In general, as a non-polymer, any of those which have a molecular weight in the range of 500 to less than 4,000 is used. Hereafter, a non-polymer having a molecular weight in the range of 500 to less than 4,000 is referred to as a low molecular weight compound.

As a polymer, any of those which have a molecular weight of 1,000 or more is generally used. Hereafter, a polymer having a molecular weight of 1,000 or more is referred to as a polymeric compound. With respect to a polymeric compound, the "molecular weight" is the weight average molecular weight in terms of the polystyrene equivalent value determined by gel permeation chromatography (GPC). Hereafter, a polymeric compound is frequently referred to simply as a "resin".

As the component (A), a resin component which exhibits changed solubility in a developing solution under action of acid may be used. Alternatively, as the component (A), a low molecular weight material which exhibits changed solubility in a developing solution under action of acid may be used.

When the resist composition of the present invention is a "negative resist composition for alkali developing process" which forms a negative pattern in an alkali developing process, for example, as the component (A), a base component that is soluble in an alkali developing solution is used, and a cross-linking agent is blended in the negative resist composition.

In the negative resist composition for alkali developing process, when acid is generated from the component (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition for alkali developing process, a resin that is soluble in an alkali developing solution (hereafter, referred to as "alkali-soluble resin") is used.

Examples of the alkali soluble resin include a resin having a structural unit derived from at least one of α-(hydroxyalkyl) acrylic acid and an alkyl ester of α-(hydroxyalkyl)acrylic acid (preferably an alkyl ester having 1 to 5 carbon atoms), as disclosed in Japanese Unexamined Patent Application, First Publication No. 2000-206694; an acrylic resin which has a sulfonamide group and may have the hydrogen atom bonded to the carbon atom on the α-position substituted with a substituent or polycycloolefin resin having a sulfoneamide group, as disclosed in U.S. Pat. No. 6,949,325; an acrylic resin which may have the hydrogen atom bonded to the carbon atom on the α-position substituted with a substituent and having a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycycloolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group, or a melamine-based cross-linking agent is preferable, as it enables formation of a resist pattern with minimal swelling. The amount of the cross-linking agent added is preferably within a range from 1 to 50 parts by weight, relative to 100 parts by weight of the alkali-soluble resin.

In the case where the resist composition of the present invention is a resist composition which forms a positive pattern in an alkali developing process and a negative pattern in a solvent developing process, it is preferable to use a base component (A0) (hereafter, referred to as "component (A0)") which exhibits increased polarity by the action of acid. By using the component (A0), since the polarity of the base component changes prior to and after exposure, an excellent development contrast can be obtained not only in an alkali developing process, but also in a solvent developing process.

More specifically, in the case of applying an alkali developing process, the component (A0) is substantially insoluble in an alkali developing solution prior to exposure, but when acid is generated from the component (B) upon exposure, the action of this acid causes an increase in the polarity of the base component, thereby increasing the solubility of the component (A0) in an alkali developing solution. Therefore, in the formation of a resist pattern, by conducting selective exposure of a resist film formed by applying the resist composition to a substrate, the exposed portions change from an insoluble state to a soluble state in an alkali developing solution, whereas the unexposed portions remain insoluble in an alkali developing solution, and hence, a positive resist pattern can be formed by alkali developing.

On the other hand, in the case of a solvent developing process, the component (A0) exhibits high solubility in an organic developing solution prior to exposure, and when acid is generated from the component (B) upon exposure, the polarity of the component (A0) is increased by the action of the generated acid, thereby decreasing the solubility of the component (A0) in an organic developing solution. Therefore, in the formation of a resist pattern, by conducting selective exposure of a resist film formed by applying the resist composition to a substrate, the exposed portions changes from an soluble state to an insoluble state in an organic developing solution, whereas the unexposed portions remain soluble in an organic developing solution. As a result, by conducting development using an organic developing solution, a contrast can be made between the exposed portions and unexposed portions, thereby enabling the formation of a negative resist pattern.

In the resist composition of the present invention, the component (A) is preferably a base component which exhibits increased polarity by the action of acid (i.e., a component (A0)). That is, the resist composition of the present invention is preferably a chemically amplified resist composition which becomes a positive type in the case of an alkali developing process, and a negative type in the case of a solvent developing process. The component (A0) may be a resin component (A1) that exhibits increased polarity under the action of acid (hereafter, frequently referred to as "component (A1)"), a low molecular weight material (A2) that exhibits increased polarity under the action of acid (hereafter, frequently referred to as "component (A2)"), or a mixture thereof

[Component (A1)]

As the component (A1), a resin component (base resin) typically used as a base component for a chemically amplified resist composition can be used alone, or two or more of such resin components can be mixed together.

In the present invention, the component (A1) preferably has a structural unit derived from an acrylate ester which may have the hydrogen atom bonded to the carbon atom on the α-position substituted with a substituent.

In the resist composition of the present invention, it is particularly desirable that the component (A1) has a structural unit (a1) derived from an acrylate ester which may have the hydrogen atom bonded to the carbon atom on the α-position substituted with a substituent and contains an acid decomposable group which exhibits increased polarity by the action of acid.

The component (A1) preferably includes, in addition to the structural unit (a1), at least one structural unit (a2) selected from the group consisting of a structural unit derived from an acrylate ester containing an $—SO_2—$ containing cyclic group and which may have the hydrogen atom bonded to the carbon atom on the α-position substituted with a substituent and a structural unit derived from an acrylate ester containing a lactone-containing cyclic group and which may have the hydrogen atom bonded to the carbon atom on the α-position substituted with a substituent.

In addition to the structural unit (a1) or in addition to the structural unit (a1) and the structural unit (a2), it is preferable that the component (A1) further include a structural unit (a3) derived from an acrylate ester containing a polar group-containing aliphatic hydrocarbon group and may have the hydrogen atom bonded to the carbon atom on the α-position substituted with a substituent.

(Structural Unit (a1))

The structural unit (a1) is a structural unit derived from an acrylate ester which may have the hydrogen atom bonded to the carbon atom on the α-position substituted with a substituent and contains an acid decomposable group which exhibits increased polarity by the action of acid.

The term "acid decomposable group" refers to a group in which at least a part of the bond within the structure thereof is cleaved by the action of acid generated from the component (B) upon exposure.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group ($—SO_3H$). Among these, a polar group containing —OH in the structure thereof (hereafter, referred to as "OH-containing polar group") is preferable, and a carboxy group or a hydroxy group is more preferable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

An "acid dissociable group" is a group in which at least the bond between the acid dissociable group and the adjacent carbon atom is cleaved by the action of acid generated from the component (B) upon exposure. It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, in the case of applying an alkali developing process, the solubility in an alkali developing solution is relatively increased. On the other hand, in the case of applying a solvent developing process, the solubility in an organic developing solution containing an organic solvent decreases.

As the acid dissociable group for the structural unit (a1), any of those which have been proposed as acid dissociable groups for a base resin of a chemically amplified resist may be used. Generally, groups that form either a cyclic or chain-like tertiary alkyl ester with the carboxyl group of the (meth) acrylic acid, and acetal-type acid dissociable groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom, thereby forming a carboxy group. As a result, the polarity of the component (A1) is increased.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable groups".

Examples of tertiary alkyl ester-type acid dissociable groups include aliphatic branched, acid dissociable groups and aliphatic cyclic group-containing acid dissociable groups.

In the present description and claims, the term "aliphatic branched" refers to a branched structure having no aromaticity.

The "aliphatic branched, acid dissociable group" is not limited to be constituted of only carbon atoms and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid dissociable groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with an alkyl group of 1 to 5 carbon atoms, a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable group, for example, a group which has a tertiary carbon atom on the ring structure of the cycloalkyl group can be used. Specific examples include groups represented by any one of general formulas (1-1) to (1-9) shown below, such as a 2-methyl-2-adamantyl group and a 2-ethyl-2-adamantyl group.

Further, as examples of aliphatic branched acid dissociable group, groups having an aliphatic cyclic group such as an adamantyl group, cyclohexyl group, cyclopentyl group, norbornyl group, tricyclodecyl group or tetracyclododecyl group, and a branched alkylene group having a tertiary carbon atom bonded thereto, as those represented by general formulas (2-1) to (2-6) shown below, can be given.

[Chemical Forumula 3]

(1-1)

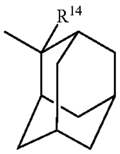

(1-2)

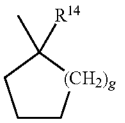

(1-3)

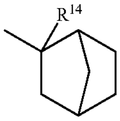

(1-4)

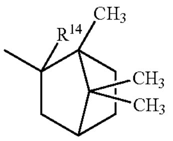

(1-5)

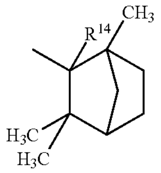

(1-6)

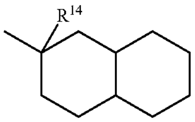

(1-7)

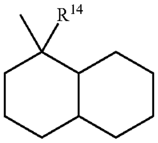

(1-8)

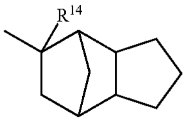

(1-9)

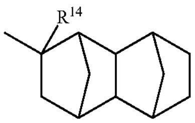

In the formulas above, $R^{14}$ represents an alkyl group; and g represents an integer of 0 to 8.

[Chemical Formula 4]

(2-1)

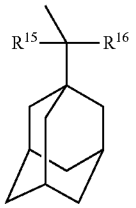

(2-2)

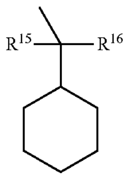

(2-3)

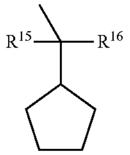

(2-4)

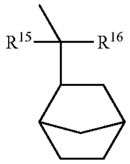

(2-5)

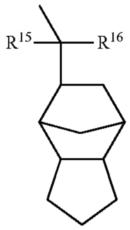

(2-6)

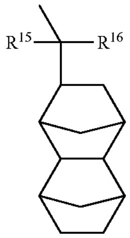

In the formulas, each of $R^{15}$ and $R^{16}$ independently represents an alkyl group (which may be linear or branched, and preferably has 1 to 5 carbon atoms).

As the alkyl group for $R^{14}$, a linear or branched alkyl group is preferable.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples of such branched alkyl groups include an isopropyl group, an isobutyl group, a tert-butyl group, an isopentyl group and a neopentyl group, and an isopropyl group or a tert-butyl group is particularly desirable.

g is preferably an integer of 0 to 3, more preferably 1 to 3, and still more preferably 1 or 2.

As the alkyl group for $R^{15}$ and $R^{16}$, the same alkyl groups as those for $R^{14}$ can be used.

In formulas (1-1) to (1-9) and (2-1) to (2-6), part of the carbon atoms constituting the ring may be replaced with an ethereal oxygen atom (—O—). Further, in formulas (1-1) to (1-9) and (2-1) to (2-6), one or more of the hydrogen atoms bonded to the carbon atoms constituting the ring may be substituted with a substituent. Examples of the substituent include an alkyl group of 1 to 5 carbon atoms, a fluorine atom and a fluorinated alkyl group.

An "acetal-type acid dissociable group" generally substitutes a hydrogen atom at the terminal of an OH-containing polar group such as a carboxy group or hydroxyl group, so as to be bonded with an oxygen atom. When acid is generated upon exposure, the generated acid acts to break the bond between the acetal-type acid dissociable group and the oxygen atom to which the acetal-type, acid dissociable group is bonded, thereby forming an OH-containing polar group such as a carboxy group or a hydroxy group. As a result, the polarity of the component (A1) is increased.

Examples of acetal-type acid dissociable groups include groups represented by general formula (p1) shown below.

[Chemical Formula 5]

(p1)

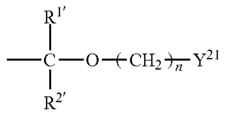

In the formula, $R^{1'}$ and $R^{2'}$ each independently represent a hydrogen atom or an alkyl group of 1 to 5 carbon atoms; n represents an integer of 0 to 3; and $Y^{21}$ represents an alkyl group of 1 to 5 carbon atoms or an aliphatic cyclic group.

In general formula (p1) above, n is preferably an integer of 0 to 2, more preferably 0 or 1, and most preferably 0.

As the alkyl group of 1 to 5 carbon atoms for $R^{1'}$ and $R^{2'}$, the same alkyl groups of 1 to 5 carbon atoms as those described above for R can be used, although a methyl group or ethyl group is preferable, and a methyl group is particularly desirable.

In the present invention, it is preferable that at least one of $R^{1'}$ and $R^{2'}$ be a hydrogen atom. That is, it is preferable that the acid dissociable group (p1) is a group represented by general formula (p1-1) shown below.

[Chemical Formula 6]

(p1-1)

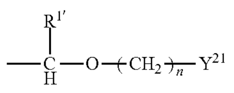

In the formula, $R^{1'}$, n and $Y^{21}$ are the same as defined above.

As the alkyl group of 1 to 5 carbon atoms for $Y^{21}$, the same alkyl groups of 1 to 5 carbon atoms as those described above can be used.

As the aliphatic cyclic group for $Y^{21}$, any of the aliphatic monocyclic/polycyclic groups which have been proposed for conventional ArF resists and the like can be appropriately selected for use. For example, the same groups described above in connection with the "aliphatic cyclic group" can be used.

Further, as the acetal-type, acid dissociable group, groups represented by general formula (p2) shown below can also be used.

[Chemical Formula 7]

(p2)

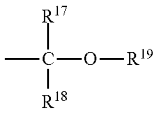

In the formula, $R^{17}$ and $R^{18}$ each independently represent a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable. It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

As the structural unit (a1), it is preferable to use at least one member selected from the group consisting of structural units represented by formula (a1-0-1) shown below and structural units represented by formula (a1-0-2) shown below.

[Chemical Formula 8]

(a1-0-1)

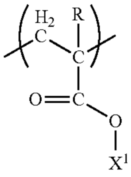

In the formula, R represents a hydrogen atom, an alkyl group of 1 to 5 carbon atoms or a halogenated alkyl group of 1 to 5 carbon atoms; and $X^1$ represents an acid dissociable group.

[Chemical Formula 9]

(a1-0-2)

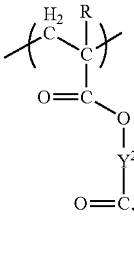

[In the formula, R represents a hydrogen atom, an alkyl group of 1 to 5 carbon atoms or a halogenated alkyl group of 1 to 5 carbon atoms; $X^2$ represents an acid dissociable group; and $Y^{22}$ represents a divalent linking group.]

In general formula (a1-0-1) above, the alkyl group of 1 to 5 carbon atoms or halogenated alkyl group of 1 to 5 carbon atoms for R are the same as the alkyl group of 1 to 5 carbon atoms or halogenated alkyl group of 1 to 5 carbon atoms which can be used as the substituent for the hydrogen atom bonded to the carbon atom on the α-position of the aforementioned acrylate ester.

$X^1$ is not particularly limited as long as it is an acid dissociable group. Examples thereof include the aforementioned tertiary alkyl ester-type acid dissociable groups and acetal-type acid dissociable groups, and tertiary alkyl ester-type acid dissociable groups are preferable.

In general formula (a1-0-2), R is the same as defined above.

$X^2$ is the same as defined for $X^1$ in general formula (a1-0-1).

As preferable examples of the divalent linking group for $Y^{22}$, a divalent hydrocarbon group which may have a substituent, and a divalent linking group containing a hetero atom can be given.

A hydrocarbon "has a substituent" means that part or all of the hydrogen atoms within the hydrocarbon group is substituted with groups or atoms other than hydrogen.

The hydrocarbon group may be either an aliphatic hydrocarbon group or an aromatic hydrocarbon group. An "aliphatic hydrocarbon group" refers to a hydrocarbon group that has no aromaticity.

The aliphatic hydrocarbon group may be saturated or unsaturated. In general, the aliphatic hydrocarbon group is preferably saturated.

As specific examples of the aliphatic hydrocarbon group for the hydrocarbon group as $Y^{22}$, a linear or branched aliphatic hydrocarbon group, and an aliphatic hydrocarbon group having a ring in the structure thereof can be given.

The linear or branched aliphatic hydrocarbon group preferably has 1 to 10 carbon atoms, more preferably 1 to 8, still more preferably 1 to 5, and most preferably 1 or 2.

As the linear aliphatic hydrocarbon group, a linear alkylene group is preferable, and specific examples include a methylene group [$—CH_2—$], an ethylene group [$—(CH_2)_2—$], a trimethylene group [$—(CH_2)_3—$], a tetramethylene group [$—(CH_2)_4—$] and a pentamethylene group [$—(CH_2)_5—$].

As the branched aliphatic hydrocarbon group, a branched alkylene group is preferable, and specific examples include alkylalkylene groups, e.g., alkylmethylene groups such as $—CH(CH_3)—$, $—CH(CH_2CH_3)—$, $—C(CH_3)_2—$, $—C(CH_3)(CH_2CH_3)—$, $—C(CH_3)(CH_2CH_2CH_3)—$, and $—C(CH_2CH_3)_2—$; alkylethylene groups such as $—CH(CH_3)CH_2—$, $—CH(CH_3)CH(CH_3)—$, $—C(CH_3)_2CH_2—$, $—CH(CH_2CH_3)CH_2—$, and $—C(CH_2CH_3)_2—CH_2—$; alkyltrimethylene groups such as $—CH(CH_3)CH_2CH_2—$, and $—CH_2CH(CH_3)CH_2—$; and alkyltetramethylene groups such as $—CH(CH_3)CH_2CH_2CH_2—$, and $—CH_2CH(CH_3)CH_2CH_2—$. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated alkyl group of 1 to 5 carbon atoms, and an oxygen atom (=O).

As examples of the hydrocarbon group containing a ring in the structure thereof, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

Examples of the aforementioned aromatic hydrocarbon group for $Y^{22}$ include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group; an aromatic hydrocarbon group in which part of the carbon atoms constituting the ring of the aforementioned divalent aromatic hydrocarbon group has been substituted with a hetero atom such as an oxygen atom, a sulfur atom or a nitrogen atom; and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

The aromatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

With respect to a "divalent linking group containing a hetero atom" for $Y^{22}$, a hetero atom is an atom other than carbon and hydrogen, and examples thereof include an oxygen atom, a nitrogen atom, a sulfur atom and a halogen atom.

When $Y^{22}$ represents a divalent linking group containing a hetero atom, examples thereof include —O—, —C(=O)—O—, —C(=O)—, —O—C(=O)—O—, —C(=O)—NH—, —NH— (H may be substituted with a substituent such as an alkyl group or an acyl group), —S—, $—S(=O)_2—$, $—S(=O)_2—O—$, "-A-O—B— (wherein O is an oxygen atom, and each of A and B independently represents a divalent hydrocarbon group which may have a substituent)" and a combination of a divalent hydrocarbon group which may have a substituent with a divalent linking group containing a hetero atom. As examples of the divalent hydrocarbon group which may have a substituent, the same groups as those described above for the hydrocarbon group which may have a substituent can be given, and a linear or branched aliphatic hydrocarbon group or an aliphatic hydrocarbon group containing a ring in the structure thereof is preferable.

When $Y^{22}$ represents a divalent linking group —NH— and the H in the formula is replaced with a substituent such as an alkyl group or an acyl group, the substituent preferably has 1 to 10 carbon atoms, more preferably 1 to 8 carbon atoms, and most preferably 1 to 5 carbon atoms.

When $Y^{22}$ is "-A-O—B—", each of A and B independently represents a divalent hydrocarbon group which may have a substituent.

The hydrocarbon group for A may be either an aliphatic hydrocarbon group, or an aromatic hydrocarbon group. An "aliphatic hydrocarbon group" refers to a hydrocarbon group that has no aromaticity.

The aliphatic hydrocarbon group for A may be either saturated or unsaturated. In general, the aliphatic hydrocarbon group is preferably saturated.

As specific examples of the aliphatic hydrocarbon group for A, a linear or branched aliphatic hydrocarbon group, and an aliphatic hydrocarbon group having a ring in the structure thereof can be given. These are the same as defined above.

Among these, as A, a linear aliphatic hydrocarbon group is preferable, more preferably a linear alkylene group, still more preferably a linear alkylene group of 2 to 5 carbon atoms, and most preferably an ethylene group.

As the hydrocarbon group for B, the same divalent hydrocarbon groups as those described above for A can be used. As B, a linear or branched aliphatic hydrocarbon group is preferable, and a methylene group or an alkylmethylene group is particularly desirable.

The alkyl group within the alkyl methylene group is preferably a linear alkyl group of 1 to 5 carbon atoms, more preferably a linear alkyl group of 1 to 3 carbon atoms, and most preferably a methyl group.

Specific examples of the structural unit (a1) include structural units represented by general formulas (a1-1) to (a1-4) shown below.

[Chemical Formula 10]

(a1-1)

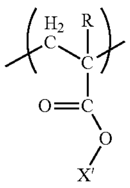

(a1-2)

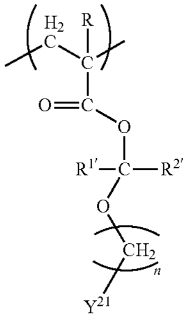

(a1-3)

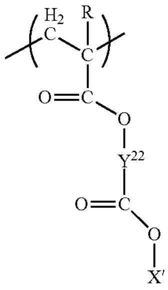

(a1-4)

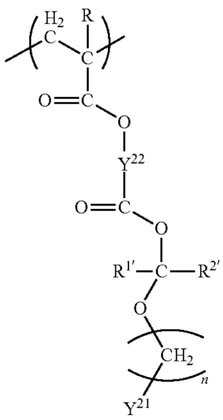

In the formulas, X' represents a tertiary alkyl ester-type acid dissociable group; $Y^{21}$ represents an alkyl group of 1 to 5 carbon atoms or an aliphatic cyclic group; n represents an integer of 0 to 3; $Y^{22}$ represents a divalent linking group; R is the same as defined above; and each of $R^{1'}$ and $R^{2'}$ independently represents a hydrogen atom or an alkyl group of 1 to 5 carbon atoms.

Examples of the tertiary alkyl ester-type acid dissociable group for X' include the same tertiary alkyl ester-type acid dissociable groups as those described above for $X^1$.

$R^{1'}$, $R^{2'}$, n and $Y^{21}$ are respectively the same as defined for $R^{1'}$, $R^{2'}$, n and $Y^{21}$ in general formula (p1) described above in connection with the "acetal-type acid dissociable group".

$Y^{22}$ is the same as defined for $Y^{22}$ in general formula (a1-0-2).

Specific examples of structural units represented by general formula (a1-1) to (a1-4) are shown below.

In the formulas shown below, $R^{\alpha}$ represents a hydrogen atom, a methyl group or a trifluoromethyl group.

[Chemical Formula 11]

(a1-1-1)

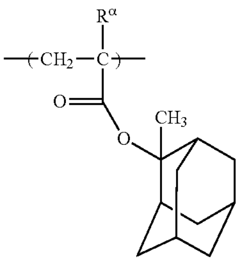

(a1-1-2)

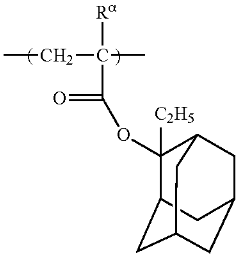

(a1-1-3)

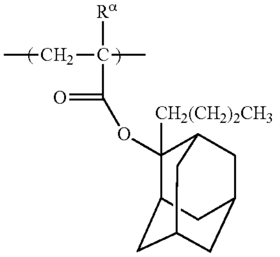

(a1-1-4)

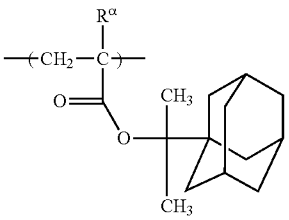

(a1-1-5)

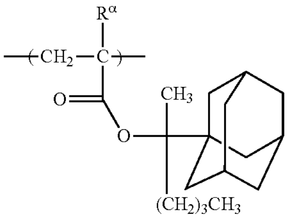

(a1-1-6)

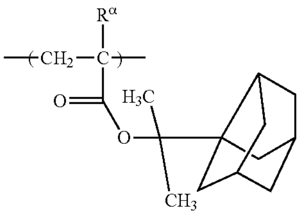

-continued
(a1-1-7)
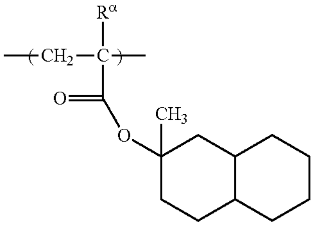
(a1-1-8)
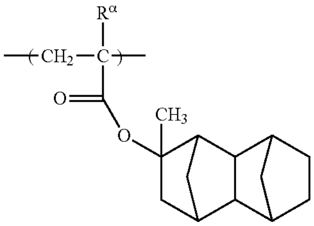
(a1-1-9)
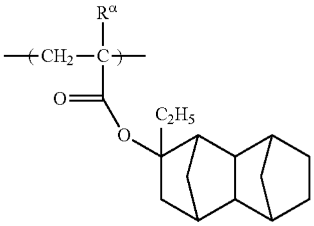
[Chemical Formula 12]
(a1-1-10)
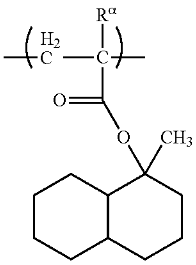
(a1-1-11)
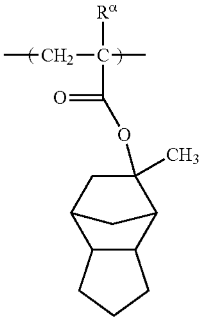
(a1-1-12)
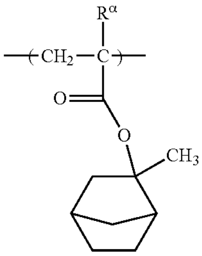
-continued
(a1-1-13)
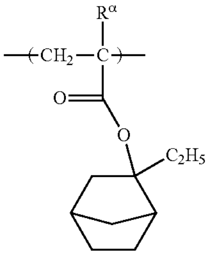
(a1-1-14)
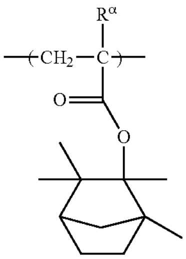
(a1-1-15)
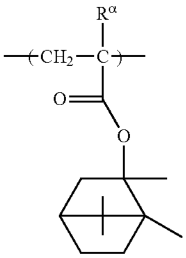
(a1-1-16)
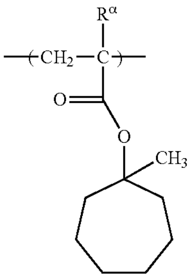
(a1-1-17)
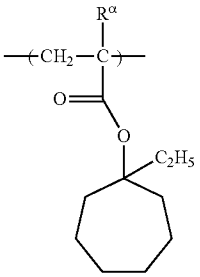
(a1-1-18)
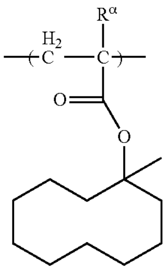

-continued
(a1-1-19)
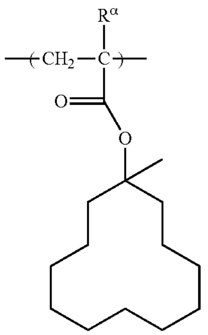
(a1-1-20)
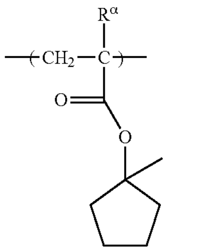
(a1-1-21)
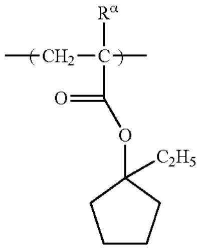
[Chemical Formula 13]
(a1-1-22)
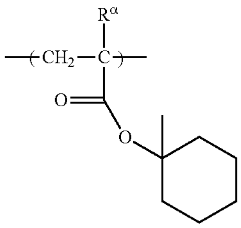
(a1-1-23)
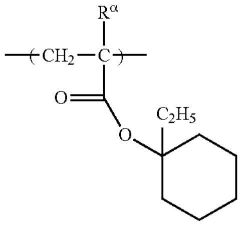
(a1-1-24)
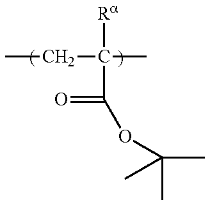
-continued
(a1-1-25)
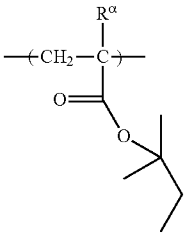
(a1-1-26)
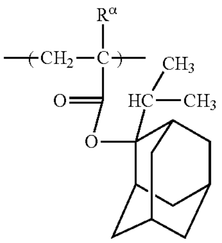
(a1-1-27)
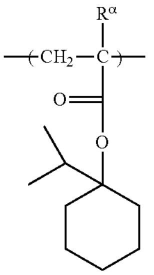
(a1-1-28)
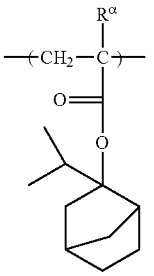
(a1-1-29)
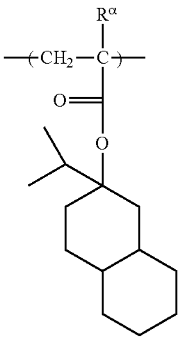

-continued
(a1-1-30)
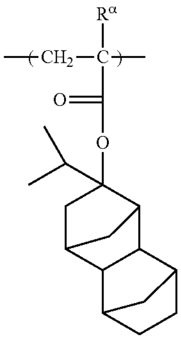
(a1-1-31)
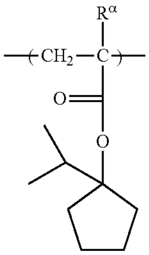
(a1-1-32)
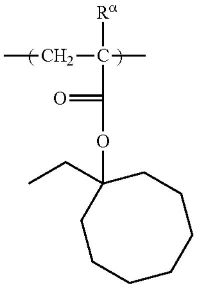
[Chemical Formula 14]
(a1-2-1)
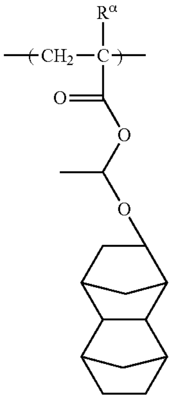
-continued
(a1-2-2)
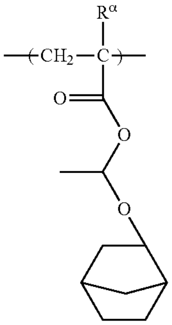
(a1-2-3)
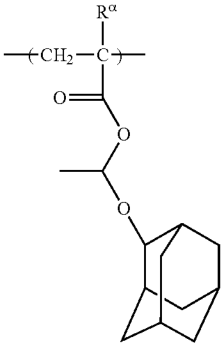
(a1-2-4)
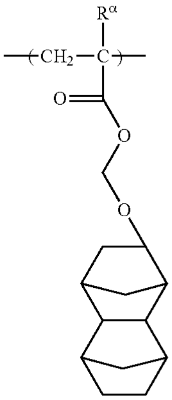
(a1-2-5)
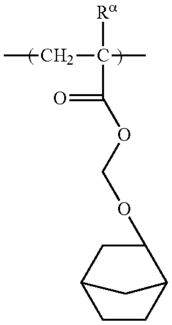

-continued
(a1-2-6)
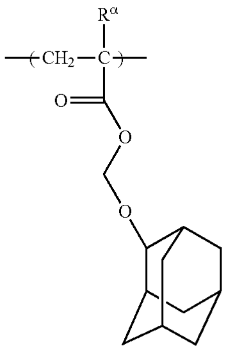
(a1-2-7)
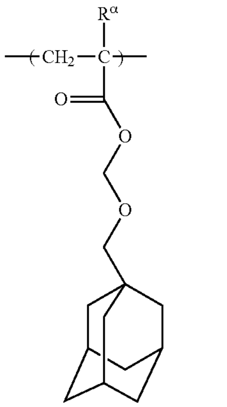
(a1-2-8)
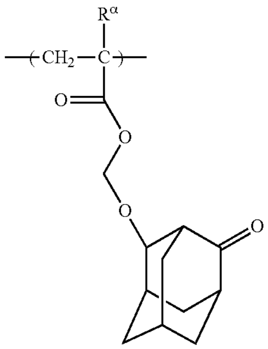
(a1-2-9)
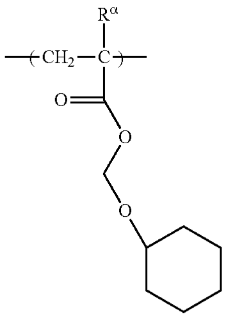
-continued
(a1-2-10)
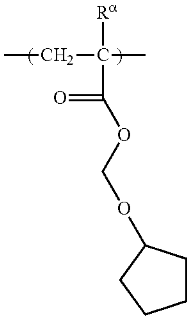
(a1-2-11)
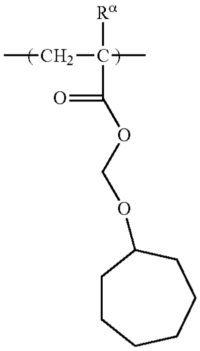
(a1-2-12)
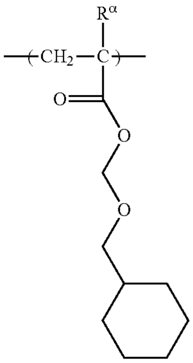
(a1-2-13)
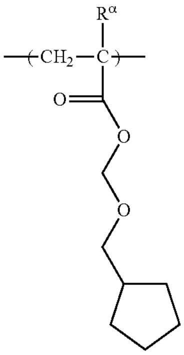

-continued
(a1-2-14)
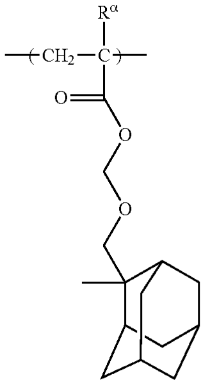
(a1-2-15)
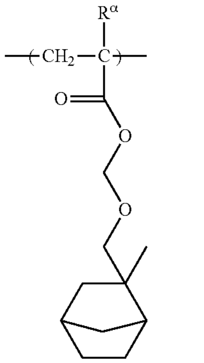
(a1-2-16)
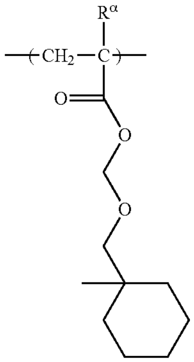
(a1-2-17)
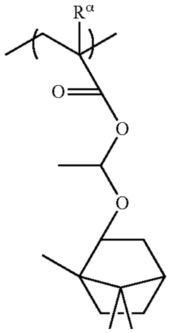
-continued
(a1-2-18)
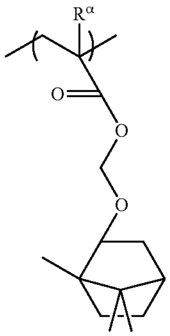
(a1-2-19)
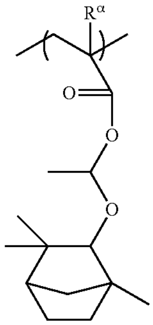
(a1-2-20)
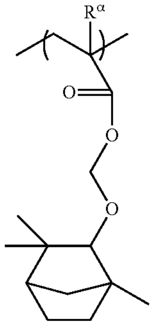
(a1-2-21)
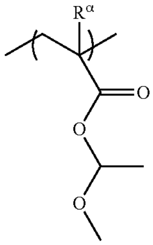
(a1-2-22)
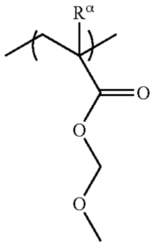

-continued
(a1-2-23)
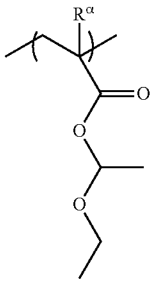
(a1-2-24)
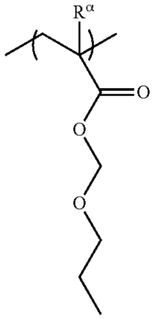
[Chemical Formula 15]
(a1-3-1)
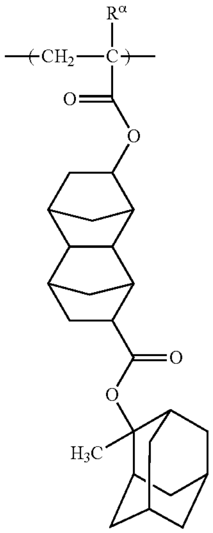
-continued
(a1-3-2)
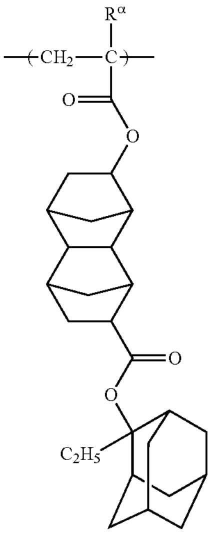
(a1-3-3)
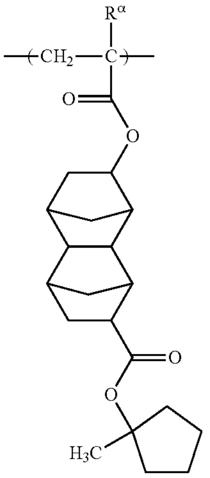
(a1-3-4)
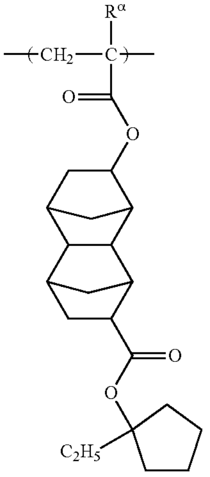

-continued
(a1-3-5)
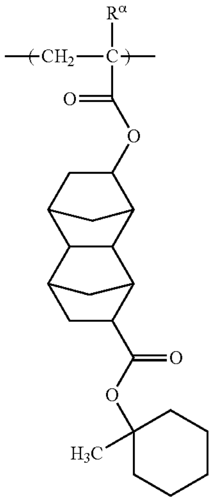
(a1-3-6)
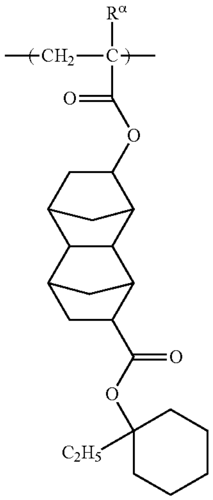
(a1-3-7)
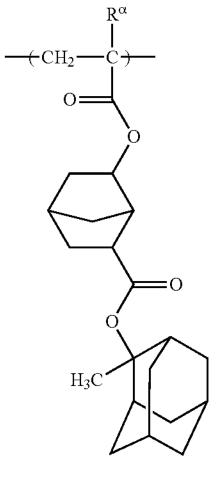
-continued
(a1-3-8)
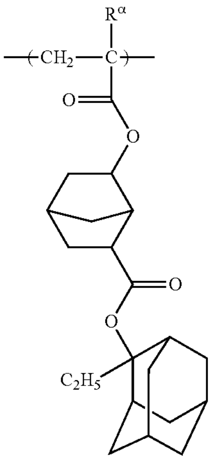
(a1-3-9)
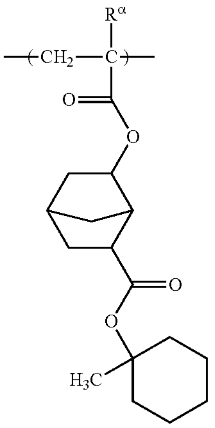
(a1-3-10)
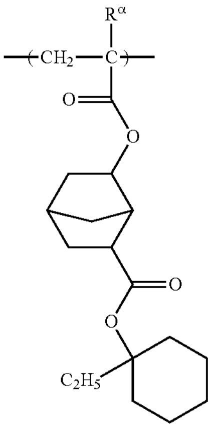

-continued
(a1-3-11)
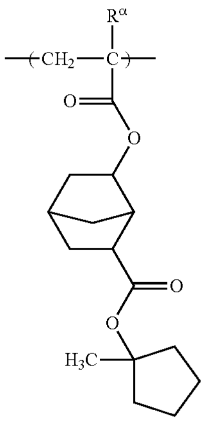
(a1-3-12)
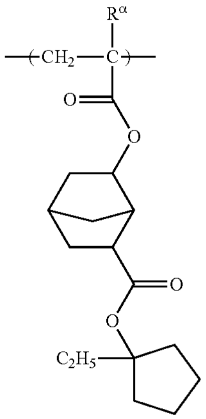
(a1-3-13)
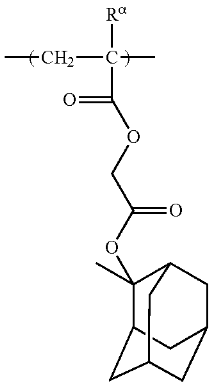
(a1-3-14)
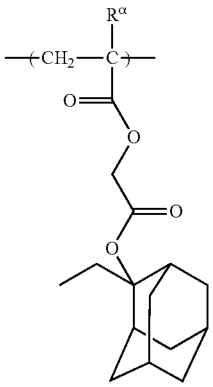
-continued
(a1-3-15)
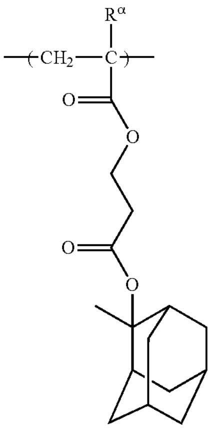
(a1-3-16)
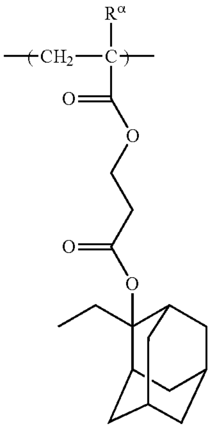
(a1-3-17)
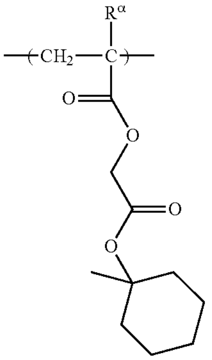
(a1-3-18)
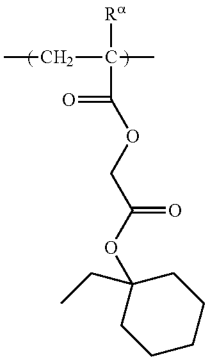

-continued
[Chemical Formula 16]
(a1-3-19)
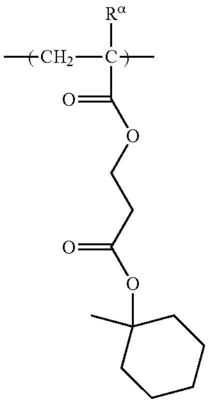
(a1-3-20)
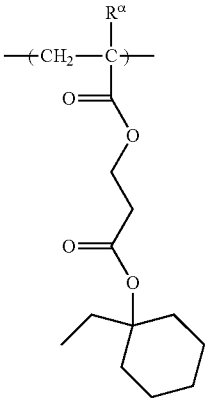
(a1-3-21)
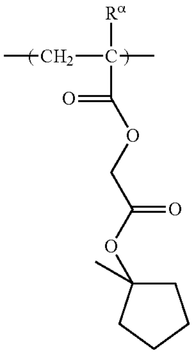
(a1-3-22)
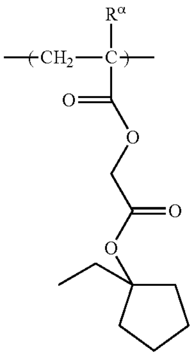
-continued
(a1-3-23)
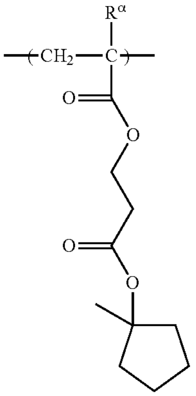
(a1-3-24)
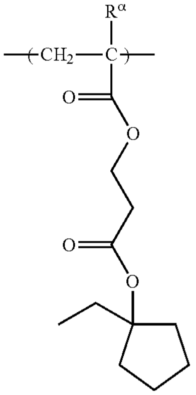
[Chemical Formula 17]
(a1-3-25)
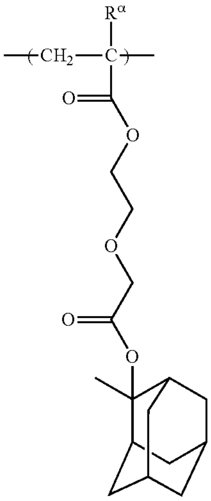

-continued
(a1-3-26)
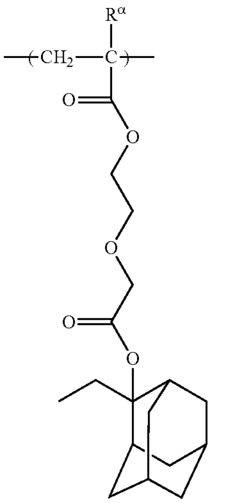
(a1-3-27)
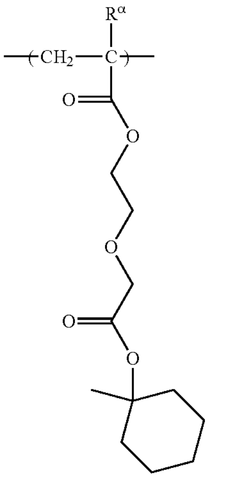
(a1-3-28)
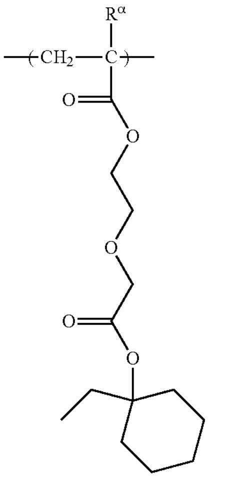
-continued
(a1-3-29)
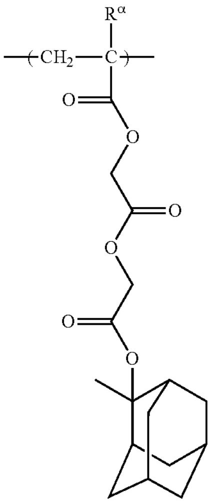
(a1-3-30)
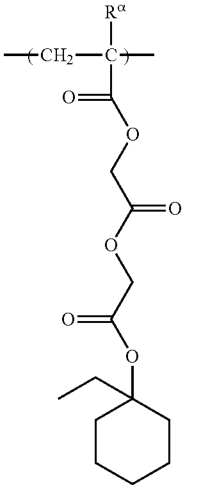
(a1-3-31)
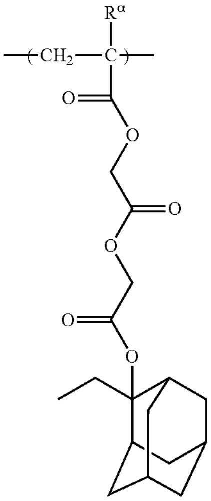

-continued
(a1-3-32)
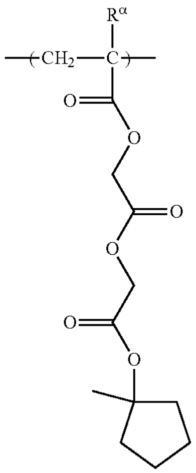
[Chemical Formula 18]
(a1-4-1)
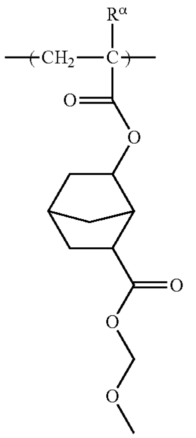
(a1-4-2)
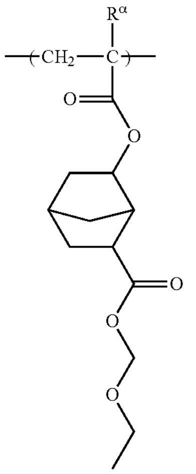
-continued
(a1-4-3)
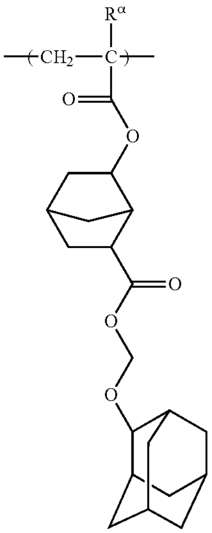
(a1-4-4)
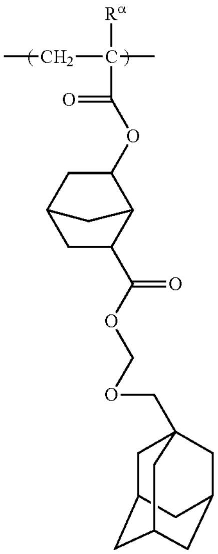
(a1-4-5)
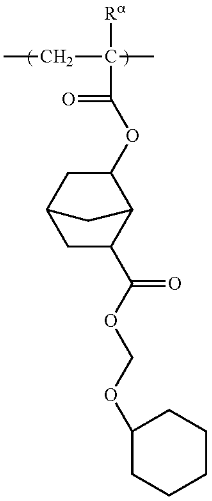

-continued
(a1-4-6)
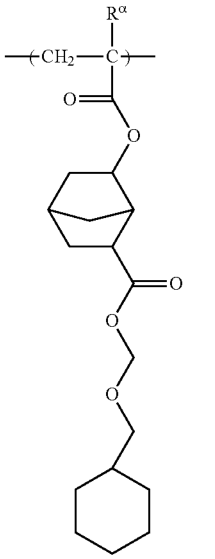
(a1-4-7)
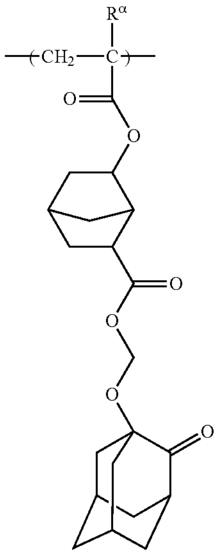
(a1-4-8)
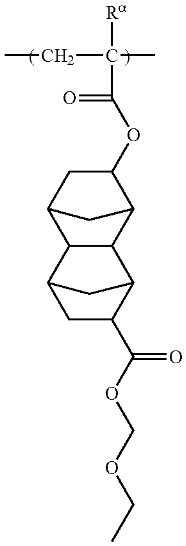
-continued
(a1-4-9)
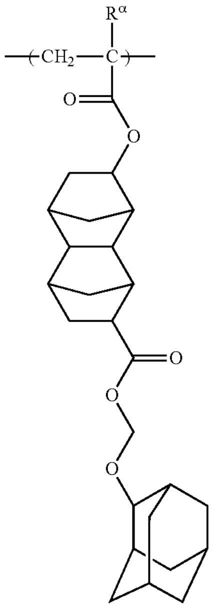
(a1-4-10)
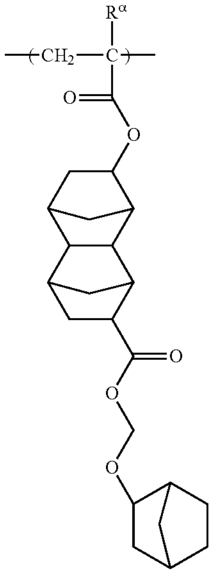

-continued
(a1-4-11)
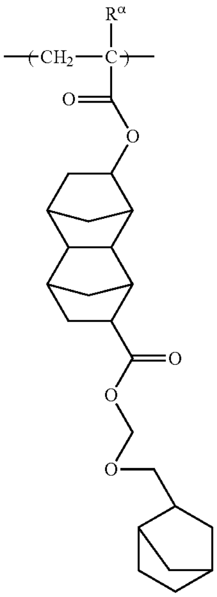
(a1-4-12)
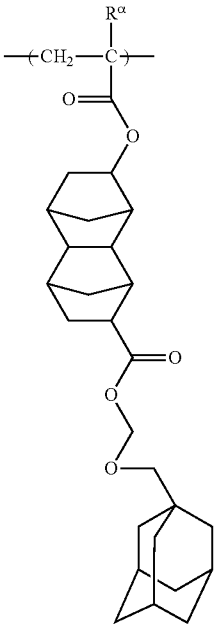
-continued
(a1-4-13)
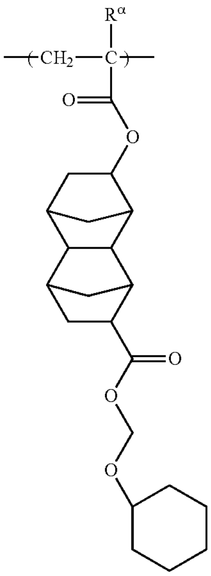
(a1-4-14)
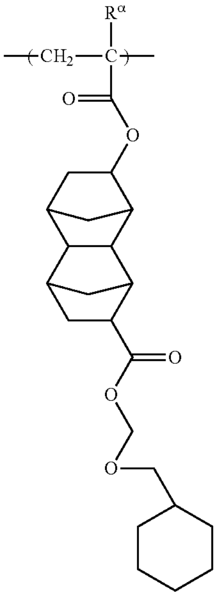

-continued (a1-4-15)

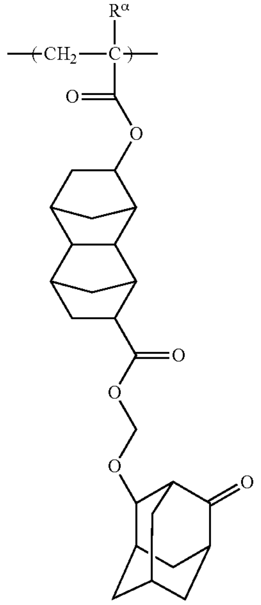

As the structural unit (a1), one type of structural unit may be used alone, or two or more types of structural units may be used in combination.

Among these, structural units represented by general formula (a1-1), (a1-2) or (a1-3) are preferable. More specifically, at least one structural unit selected from the group consisting of structural units represented by formulas (a1-1-1) to (a-1-1-4), (a1-1-20) to (a1-1-23), (a1-2-1) to (a1-2-24) and (a1-3-25) to (a1-3-28) is more preferable.

Further, as the structural unit (a1), structural units represented by general formula (a1-0-01) shown below which includes the structural units represented by formulas (a1-1-1) to (a1-1-3) and (a1-1-26), structural units represented by general formula (a1-0-02) shown below which includes the structural units represented by formulas (a1-0-16), (a1-1-17), (a1-1-20) to (a1-1-23) and (a1-1-32), structural units represented by general formula (a1-3-01) shown below which include the structural units represented by formulas (a1-3-25) and (a1-3-26), structural units represented by general formula (a1-3-02) shown below which include the structural units represented by formulas (a1-3-27) and (a1-3-28), and structural units represented by general formula (a1-3-03) shown below which include the structural units represented by formulas (a1-3-29) and (a1-3-30) are also preferable.

[Chemical Formula 19]

(a1-1-01)

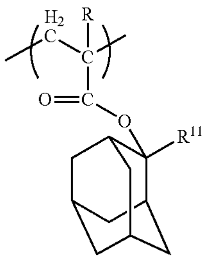

-continued (a1-1-02)

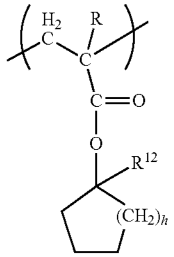

In the formulas, each R independently represents a hydrogen atom, an alkyl group of 1 to 5 carbon atoms or a halogenated alkyl group of 1 to 5 carbon atoms; $R^{11}$ represents an alkyl group of 1 to 5 carbon atoms; $R^{12}$ represents an alkyl group of 1 to 7 carbon atoms; and h represents an integer of 1 to 6.

In general formula (a1-0-01), R is the same as defined above. The alkyl group of 1 to 5 carbon atoms for $R^{11}$ is the same as defined for the alkyl group of 1 to 5 carbon atoms for R, and a methyl group, an ethyl group or an isopropyl group is preferable.

In general formula (a1-0-02), R is as defined above. The alkyl group of 1 to 5 carbon atoms for $R^{11}$ is the same as defined for the alkyl group of 1 to 5 carbon atoms for R, and a methyl group, an ethyl group or an isopropyl group is preferable. h is preferably 1 or 2, and most preferably 2.

[Chemical Formula 20]

(a1-3-01)

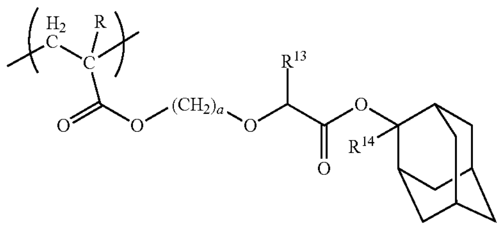

In the formula, R represents a hydrogen atom, an alkyl group of 1 to 5 carbon atoms or a halogenated alkyl group of 1 to 5 carbon atoms; $R^{14}$ is the same as defined above; $R^{13}$ represents a hydrogen atom or a methyl group; and a represents an integer of 1 to 10.

[Chemical Formula 21]

(a1-3-02)

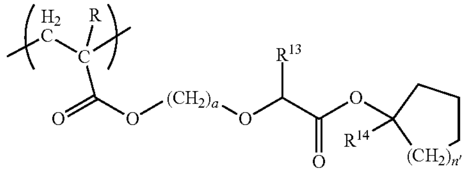

In the formula, R represents a hydrogen atom, an alkyl group of 1 to 5 carbon atoms or a halogenated alkyl group of 1 to 5 carbon atoms; $R^{14}$ is the same as defined above; $R^{13}$ represents a hydrogen atom or a methyl group; a represents an integer of 1 to 10; and n' represents an integer of 1 to 6.

[Chemical Formula 22]

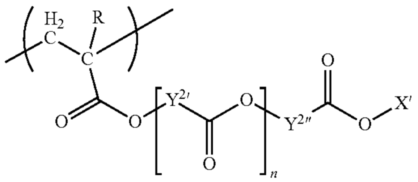

(a1-3-03)

In the formula, R is the same as defined above; each of $Y^{2'}$ and $Y^{2''}$ independently represents a divalent linking group; X' represents an acid dissociable group; and n represents an integer of 0 to 3.

In general formulas (a1-3-01) to (a1-3-03), R is the same as defined above.

$R^{13}$ is preferably a hydrogen atom.

n' is preferably 1 or 2, and most preferably 2.

a is preferably an integer of 1 to 8, more preferably 2 to 5, and most preferably 2.

As the divalent linking group for $Y^{2'}$ and $Y^{2''}$, the same groups as those described above for $Y^{22}$ in general formula (a1-3) can be used.

As $Y^{2'}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As $Y^{2''}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As the acid dissociable group for X', the same groups as those described above can be used. X' is preferably a tertiary alkyl ester-type acid dissociable group, more preferably the aforementioned group which has a tertiary carbon atom on the ring structure of a cyclic alkyl group. Among the aforementioned groups, groups represented by the aforementioned general formulas (1-1) to (1-9) are preferable. n represents an integer of 0 to 3, preferably an integer of 0 to 2, more preferably 0 or 1, and most preferably 1.

In the component (A1), as the structural unit (a1), one type of structural unit may be used, or two or more types may be used in combination.

In the component (A1), the amount of the structural unit (a1) based on the combined total of all structural units constituting the component (A1) is preferably 5 to 90 mol %, more preferably 10 to 85 mol %, and still more preferably 15 to 80 mol %. When the amount of the structural unit (a1) is at least as large as the lower limit of the above-mentioned range, a pattern can be easily formed using a resist composition prepared from the component (A1). On the other hand, when the amount of the structural unit (a1) is no more than the upper limit of the above-mentioned range, a good balance can be achieved with the other structural units.

(Structural Unit (a2))

The structural unit (a2) is at least one structural unit selected from the group consisting of a structural unit derived from an acrylate ester which may have the hydrogen atom bonded to the carbon atom on the α-position substituted with a substituent and contains an —$SO_2$— containing cyclic group (hereafter, referred to as "structural unit ($a2^S$)"), and a structural unit derived from an acrylate ester which may have the hydrogen atom bonded to the carbon atom on the α-position substituted with a substituent and contains a lactone-containing cyclic group (hereafter, referred to as "structural unit ($a2^L$)").

By virtue of the structural unit (a2) containing a —$SO_2$— containing cyclic group or a lactone-containing cyclic group, a resist composition containing the component (A1) including the structural unit (a2) is capable of improving the adhesion of a resist film to a substrate, and increasing the compatibility with the developing solution containing water (especially in the case of alkali developing process), thereby contributing to improvement of lithography properties.

Structural Unit ($a2^S$):

The structural unit ($a2^S$) is a structural unit derived from an acrylate ester which may have the hydrogen atom bonded to the carbon atom on the α-position substituted with a substituent and contains an —$SO_2$— containing cyclic group.

Here, an "—$SO_2$— containing cyclic group" refers to a cyclic group having a ring containing —$SO_2$— within the ring structure thereof, i.e., a cyclic group in which the sulfur atom (S) within —$SO_2$— forms part of the ring skeleton of the cyclic group. The ring containing —$SO_2$— within the ring skeleton thereof is counted as the first ring. A cyclic group in which the only ring structure is the ring that contains —$SO_2$— in the ring skeleton thereof is referred to as a monocyclic group, and a group containing other ring structures is described as a polycyclic group regardless of the structure of the other rings. The —$SO_2$— containing cyclic group may be either a monocyclic group or a polycyclic group.

As the —$SO_2$— containing cyclic group, a cyclic group containing —O—$SO_2$— within the ring skeleton thereof, i.e., a cyclic group containing a sultone ring in which —O—S— within the —O—$SO_2$— group forms part of the ring skeleton thereof is particularly desirable.

The —$SO_2$— containing cyclic group preferably has 3 to 30 carbon atoms, more preferably 4 to 20, still more preferably 4 to 15, and most preferably 4 to 12. Herein, the number of carbon atoms refers to the number of carbon atoms constituting the ring skeleton, excluding the number of carbon atoms within a substituent.

The —$SO_2$— containing cyclic group may be either a —$SO_2$— containing aliphatic cyclic group or a —$SO_2$— containing aromatic cyclic group. A —$SO_2$— containing aliphatic cyclic group is preferable.

Examples of the —$SO_2$— containing aliphatic cyclic group include aliphatic cyclic groups in which part of the carbon atoms constituting the ring skeleton has been substituted with a —$SO_2$— group or a —O—$SO_2$— group and has at least one hydrogen atom removed from the aliphatic hydrocarbon ring. Specific examples include an aliphatic hydrocarbon ring in which a —$CH_2$— group constituting the ring skeleton thereof has been substituted with a —$SO_2$— group and has at least one hydrogen atom removed therefrom; and an aliphatic hydrocarbon ring in which a —$CH_2$—$CH_2$— group constituting the ring skeleton has been substituted with a —O—$SO_2$— group and has at least one hydrogen atom removed therefrom.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The —$SO_2$— containing cyclic group may have a substituent. Examples of substituents include an alkyl group, an alkoxy group, a halogen atom, a halogenated alkyl group, a hydroxy group, an oxygen atom (═O), —COOR", —OC(═O)R", a hydroxyalkyl group and a cyano group.

The alkyl group for the substituent is preferably an alkyl group of 1 to 6 carbon atoms. Further, the alkyl group is preferably a linear alkyl group or a branched alkyl group. Specific examples include a methyl group, ethyl group, propyl group, isopropyl group, n-butyl group, isobutyl group, tert-butyl group, pentyl group, isopentyl group, neopentyl group and hexyl group. Among these, a methyl group or ethyl group is preferable, and a methyl group is particularly desirable.

As the alkoxy group for the substituent, an alkoxy group of 1 to 6 carbon atoms is preferable. Further, the alkoxy group is preferably a linear alkoxy group or a branched alkyl group. Specific examples of the alkoxy groups include the aforementioned alkyl groups for the substituent having an oxygen atom (—O—) bonded thereto.

Examples of the halogen atom for the substituent include a fluorine atom, a chlorine atom, a bromine atom and an iodine atom, and a fluorine atom is preferable. Examples of the halogenated alkyl group for the substituent include groups in which part or all of the hydrogen atoms within the aforementioned alkyl groups has been substituted with the aforementioned halogen atoms.

As examples of the halogenated lower alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

In the —COOR" group and the —OC(═O)R" group, R" represents a hydrogen atom or a linear, branched or cyclic alkyl group of 1 to 15 carbon atoms. When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group for the substituent preferably has 1 to 6 carbon atoms, and specific examples thereof include the aforementioned alkyl groups for the substituent in which at least one hydrogen atom has been substituted with a hydroxy group.

More specific examples of the —$SO_2$— containing cyclic group include groups represented by general formulas (3-1) to (3-4) shown below.

[Chemical Formula 23]

(3-1)

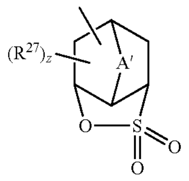

(3-2)

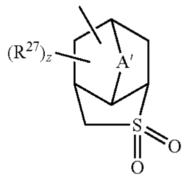

(3-3)

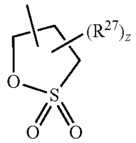

(3-4)

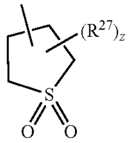

In the formulas, A' represents an oxygen atom, a sulfur atom or an alkylene group of 1 to 5 carbon atoms which may contain an oxygen atom or a sulfur atom; z represents an integer of 0 to 2; and $R^{27}$ represents an alkyl group, an alkoxy group, a halogenated alkyl group, a hydroxyl group, —COOR", —OC(═O)R", a hydroxyalkyl group or a cyano group, wherein R" represents a hydrogen atom or an alkyl group.

In general formulas (3-1) to (3-4) above, A' represents an oxygen atom (—O—), a sulfur atom (—S—) or an alkylene group of 1 to 5 carbon atoms which may contain an oxygen atom or a sulfur atom.

As the alkylene group of 1 to 5 carbon atoms for A', a linear or branched alkylene group is preferable, and examples thereof include a methylene group, an ethylene group, an n-propylene group and an isopropylene group.

Examples of alkylene groups that contain an oxygen atom or a sulfur atom include the aforementioned alkylene groups in which —O— or —S— is bonded to the terminal of the alkylene group or interposed within the alkyl group. Specific examples of such alkylene groups include —O—$CH_2$—, —S—$CH_2$— and —$CH_2$—S—$CH_2$—.

As A', an alkylene group of 1 to 5 carbon atoms or —O— is preferable, more preferably an alkylene group of 1 to 5 carbon atoms, and most preferably a methylene group.

z represents an integer of 0 to 2, and is most preferably 0.

When z is 2, the plurality of $R^{27}$ may be the same or different from each other.

As the alkyl group, alkoxy group, halogenated alkyl group, —COOR", —OC(═O)R" and hydroxyalkyl group for $R^{27}$, the same alkyl groups, alkoxy groups, halogenated alkyl groups, —COOR", —OC(═O)R" and hydroxyalkyl groups as those described above as the substituent for the —$SO_2$— containing cyclic group can be mentioned.

Specific examples of the cyclic groups represented by general formulas (3-1) to (3-4) are shown below. In the formulas shown below, "Ac" represents an acetyl group.

[Chemical Formula 24]
(3-1-1)
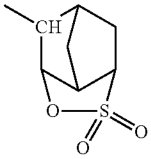
(3-1-2)
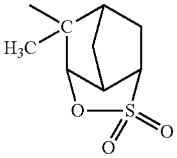
(3-1-3)
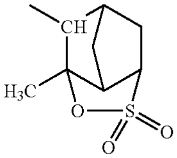
(3-1-4)
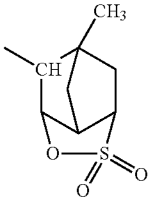
(3-1-5)
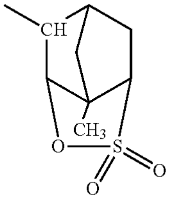
(3-1-6)
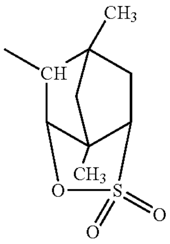
(3-1-7)
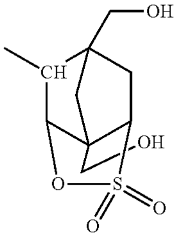
-continued
(3-1-8)
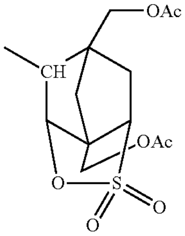
(3-1-9)
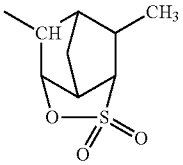
(3-1-10)
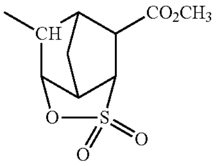
(3-1-11)
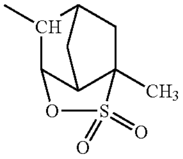
(3-1-12)
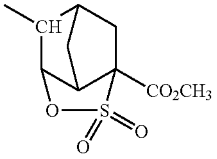
[Chemical Formula 25]
(3-1-13)
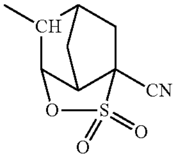
(3-1-14)
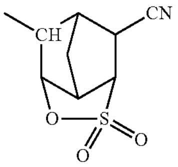
(3-1-15)
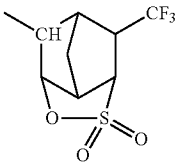

-continued
(3-1-16)
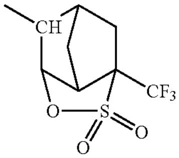
(3-1-17)
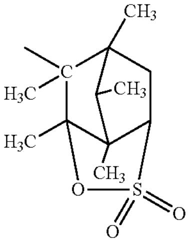
[Chemical Formula 26]
(3-1-18)
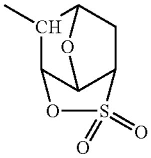
(3-1-19)
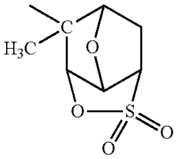
(3-1-20)
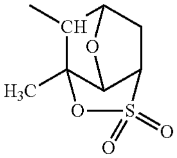
(3-1-21)
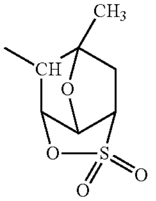
(3-1-22)
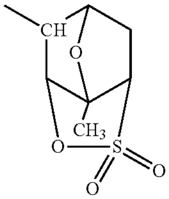
(3-1-23)
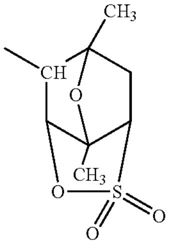
-continued
(3-1-24)
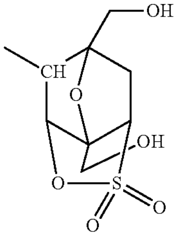
(3-1-25)
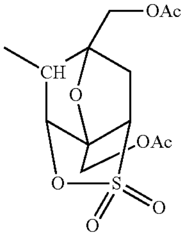
[Chemical Formula 27]
(3-1-26)
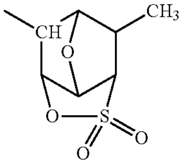
(3-1-27)
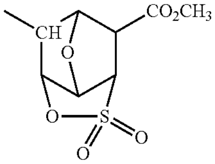
(3-1-28)
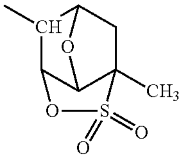
(3-1-29)
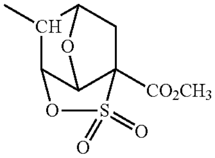
(3-1-30)
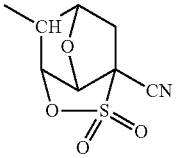
(3-1-31)
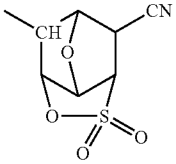

-continued (3-1-32)

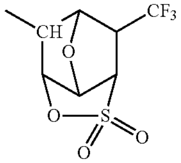

(3-1-33)

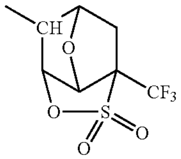

[Chemical Formula 28]

(3-2-1)

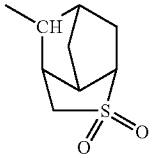

(3-2-2)

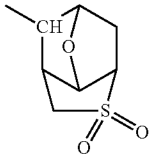

(3-3-1)

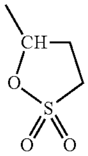

(3-4-1)

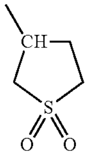

As the $—SO_2—$ containing cyclic group, a group represented by the aforementioned general formula (3-1) is preferable, at least one member selected from the group consisting of groups represented by the aforementioned chemical formulas (3-1-1), (3-1-18), (3-3-1) and (3-4-1) is more preferable, and a group represented by chemical formula (3-1-1) is most preferable.

More specific examples of the structural unit ($a2^S$) include structural units represented by general formula (a2-0) shown below.

[Chemical Formula 29]

(a2-0)

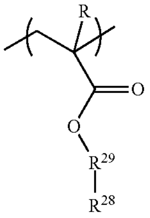

In the formula, R represents a hydrogen atom, an alkyl group of 1 to 5 carbon atoms or a halogenated alkyl group of 1 to 5 carbon atoms; $R^{28}$ represents a $—SO_2—$ containing cyclic group; and $R^{29}$ represents a single bond or a divalent linking group.

In general formula (a2-0), R is the same as defined above.

$R^{28}$ is the same as defined for the aforementioned $—SO_2—$ containing group.

$R^{29}$ may be either a single bond or a divalent linking group. In terms of the effects of the present invention, a divalent linking group is preferable.

The divalent linking group for $R^{29}$ is not particularly limited, and examples thereof include the same divalent linking groups as those described above for $Y^{22}$ in the aforementioned formula (a1-0-2). Among these, an alkylene group or a divalent linking group containing an ester bond (—C(=O)—O—) is preferable.

As the alkylene group, a linear or branched alkylene group is preferable. Specific examples include the same linear alkylene groups and branched alkylene groups as those described above for the aliphatic hydrocarbon group represented by $Y^{22}$.

As the divalent linking group containing an ester bond, a group represented by general formula: $—R^{30}—C(=O)—O—$ (in the formula, $R^{30}$ represents a divalent linking group) is particularly desirable. That is, the structural unit ($a2^S$) is preferably a structural unit represented by general formula (a1-0-1) shown below.

[Chemical Formula 30]

(a2-0-1)

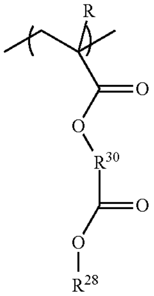

In the formula, R and $R^{28}$ are the same as defined above; and $R^{30}$ represents a divalent linking group.

$R^{30}$ is not particularly limited, and examples thereof include the same divalent linking groups as those described above for $Y^{22}$ in the aforementioned formula (a1-0-2).

As the divalent linking group for $R^{30}$, an alkylene group, a divalent alicyclic hydrocarbon group or a divalent linking group containing a hetero atom is preferable.

As the linear or branched alkylene group, the divalent alicyclic hydrocarbon group and the divalent linking group containing a hetero atom, the same linear or branched alkylene group, cyclic aliphatic hydrocarbon group and divalent linking group containing a hetero atom as those described above for $Y^{22}$ can be mentioned.

Among these, a linear or branched alkylene group, or a divalent linking group containing an oxygen atom as a hetero atom is more preferable.

As the linear alkylene group, a methylene group or an ethylene group is preferable, and a methylene group is particularly desirable.

As the branched alkylene group, an alkylmethylene group or an alkylethylene group is preferable, and $—CH(CH_3)—$, $—C(CH_3)_2—$ or $—C(CH_3)_2CH_2—$ is particularly desirable.

As the divalent linking group containing a hetero atom, a divalent linking group containing an ether bond or an ester bond is preferable, and a group represented by the aforementioned formula -A-O—B—, $-[A-C(=O)—O]_m—B—$ or -A-O—C(=O)—B— is more preferable.

Among these, a group represented by the formula -A-O—C(=O)—B— is preferable, and a group represented by the formula: $—(CH_2)_{c1}—C(=O)—O—(CH_2)_{d1}—$ is particularly desirable. c1 represents an integer of 1 to 5, and preferably 1 or 2. d1 represents an integer of 1 to 5, and preferably 1 or 2.

In particular, as the structural unit ($a2^S$), a structural unit represented by general formula (a0-1-11) or (a0-1-12) shown below is preferable, and a structural unit represented by general formula (a0-1-12) shown below is more preferable.

[Chemical Formula 31]

(a0-1-11)

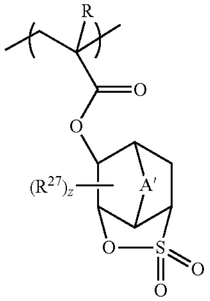

(a0-1-12)

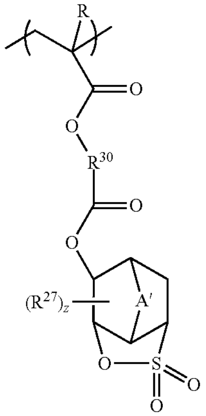

In the formulas, R, A', $R^{27}$, z and $R^{30}$ are the same as defined above.

In general formula (a0-1-11), A' is preferably a methylene group, an oxygen atom (—O—) or a sulfur atom (—S—).

As $R^{30}$, a linear or branched alkylene group or a divalent linking group containing an oxygen atom is preferable. As the linear or branched alkylene group and the divalent linking group containing an oxygen atom represented by $R^{30}$, the same linear or branched alkylene groups and the divalent linking groups containing an oxygen atom as those described above can be mentioned.

As the structural unit represented by general formula (a0-1-12), a structural unit represented by general formula (a0-1-12a) or (a0-1-12b) shown below is particularly desirable.

[Chemical Formula 32]

(a0-1-12a)

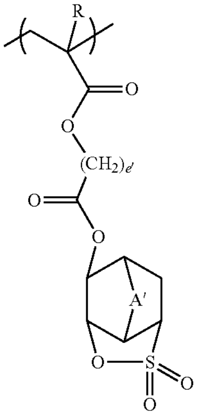

(a0-1-12b)

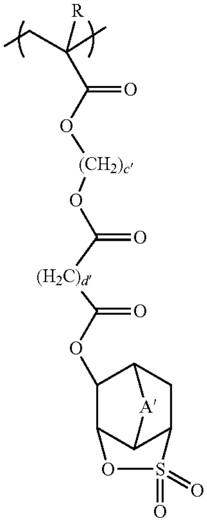

In the formulas, R and A' are the same as defined above; and each of c' to e' independently represents an integer of 1 to 3.

Structural Unit ($a2^L$):

The structural unit ($a2^L$) is a structural unit derived from an acrylate ester which may have the hydrogen atom bonded to the carbon atom on the α-position substituted with a substituent and contains a lactone-containing cyclic group.

The term "lactone-containing cyclic group" refers to a cyclic group including a ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for the structural unit ($a2^L$) is not particularly limited, and an arbitrary structural unit may be used. Specific examples of lactone-containing monocyclic groups include a group in which one hydrogen atom has been removed from a 4- to 6-membered lactone ring, such as a group in which one hydrogen atom has been removed from β-propionolatone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

Examples of the structural unit ($a2^L$) include structural units represented by the aforementioned general formula (a2-0) in which the $R^{28}$ group has been substituted with a lactone-containing cyclic group. Specific examples include structural units represented by general formulas (a2-1) to (a2-5) shown below.

[Chemical Formula 33]

(a2-1)

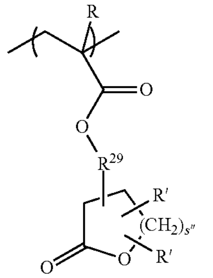

(a2-2)

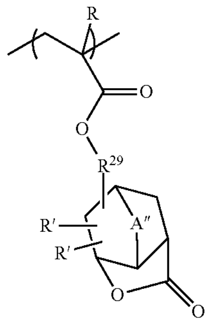

(a2-3)

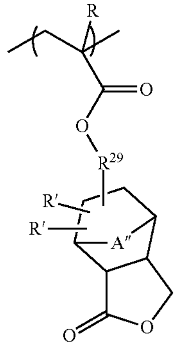

-continued (a2-4)

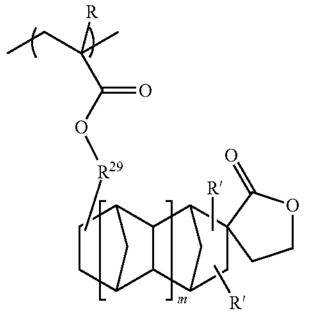

(a2-5)

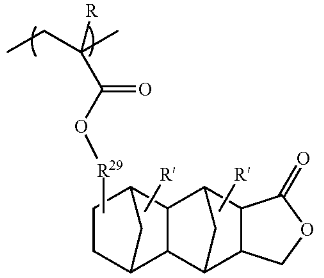

In the formulas, R represents a hydrogen atom, an alkyl group of 1 to 5 carbon atoms or a halogenated alkyl group of 1 to 5 carbon atoms; each R' independently represents a hydrogen atom, an alkyl group of 1 to 5 carbon atoms, an alkoxy group of 1 to 5 carbon atoms or —COOR", wherein R" represents a hydrogen atom or an alkyl group; $R^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as R in the structural unit (a1).

Examples of the alkyl group of 1 to 5 carbon atoms for R' include a methyl group, an ethyl group, a propyl group, an n-butyl group and a tert-butyl group.

Examples of the alkoxy group of 1 to 5 carbon atoms for R' include a methoxy group, an ethoxy group, an n-propoxy group, an iso-propoxy group, an n-butoxy group and a tert-butoxy group In terms of industrial availability, R' is preferably a hydrogen atom.

The alkyl group for R" may be any of linear, branched or cyclic.

When R" is a linear or branched alkyl group, it preferably has 1 to 10 carbon atoms, more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

As examples of A", the same groups as those described above for A' in general formula (3-1) can be given. A" is preferably an alkylene group of 1 to 5 carbon atoms, an oxygen atom (—O—) or a sulfur atom (—S—), and more preferably an alkylene group of 1 to 5 carbon atoms or —O—. As the alkylene group of 1 to 5 carbon atoms, a methylene group or a dimethylethylene group is preferable, and a methylene group is particularly desirable.

$R^{29}$ is the same as defined for $R^{29}$ in the aforementioned general formula (a2-0). In formula (a2-1), s" is preferably 1 or 2.

Specific examples of structural units represented by general formulas (a2-1) to (a2-5) are shown below. In the formulas shown below, $R^{\alpha}$ represents a hydrogen atom, a methyl group or a trifluoromethyl group.

[Chemical Formula 34]

(a2-1-1)

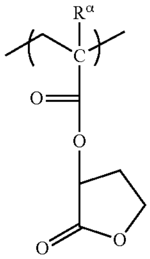

(a2-1-2)

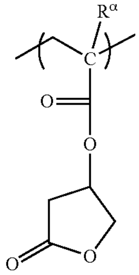

(a2-1-3)

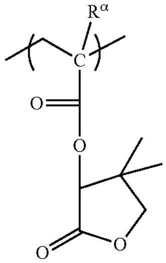

(a2-1-4)

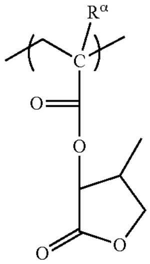

-continued (a2-1-5)

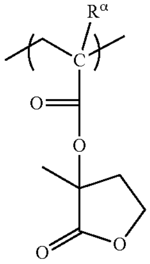

(a2-1-6)

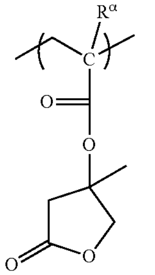

(a2-1-7)

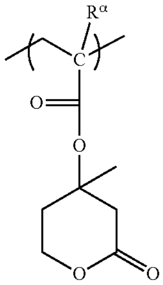

(a2-1-8)

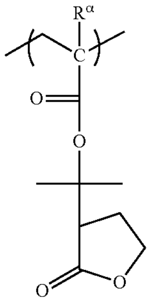

(a2-1-9)

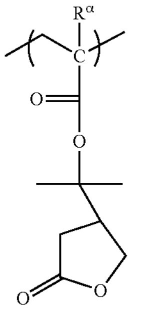

-continued
(a2-1-10)
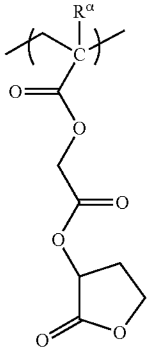
(a2-1-11)
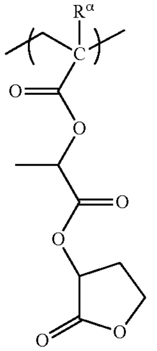
(a2-1-12)
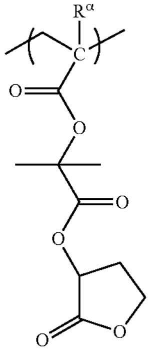
(a2-1-13)
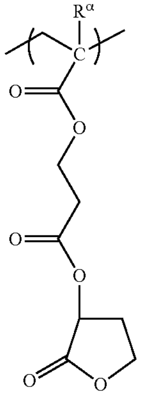
-continued
[Chemical Formula 35]
(a2-2-1)
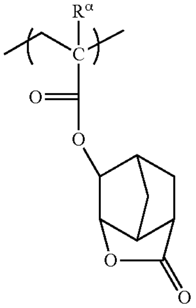
(a2-2-2)
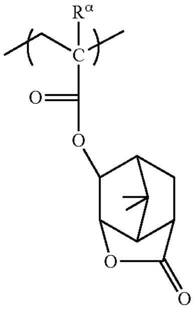
(a2-2-3)
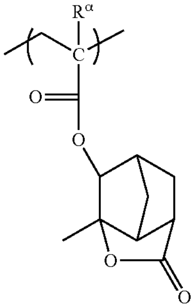
(a2-2-4)
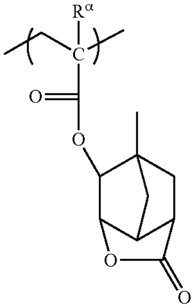
(a2-2-5)
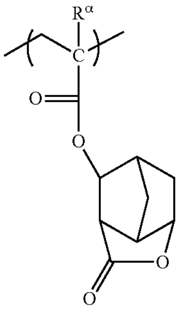

-continued
(a2-2-6)
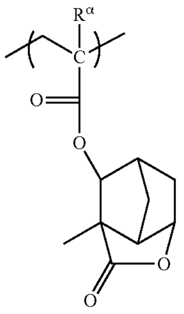
(a2-2-7)
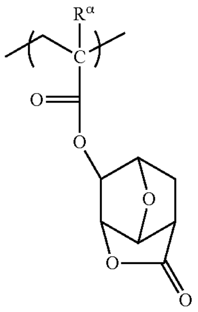
(a2-2-8)
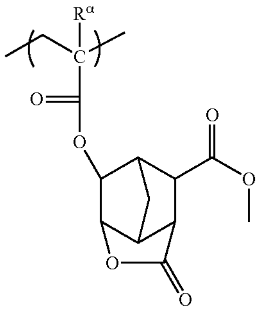
(a2-2-9)
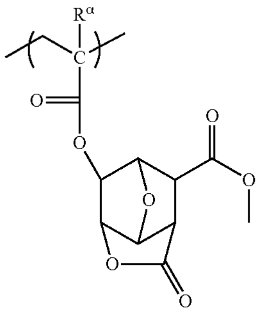
(a2-2-10)
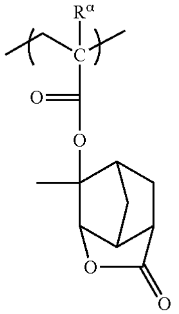
-continued
(a2-2-11)
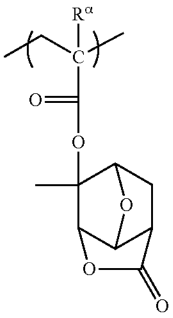
(a2-2-12)
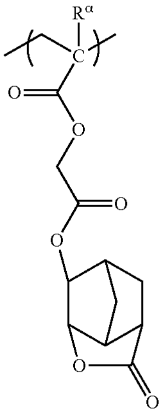
(a2-2-13)
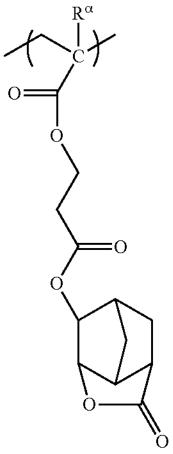
(a2-2-14)
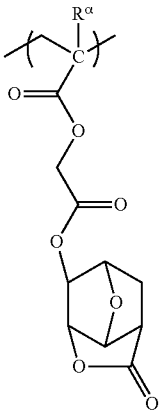

-continued
(a2-2-15)
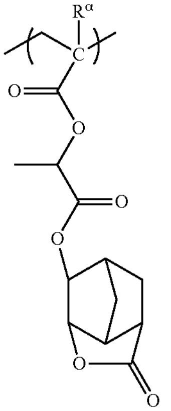
(a2-2-16)
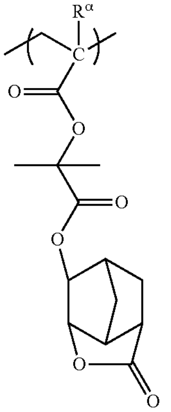
(a2-2-17)
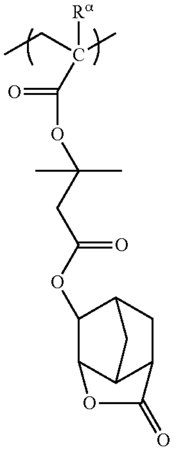
[Chemical Formula 36]
(a2-3-1)
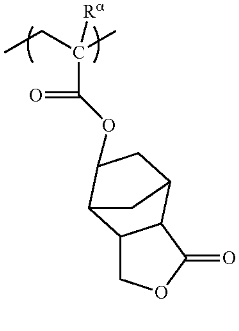
-continued
(a2-3-2)
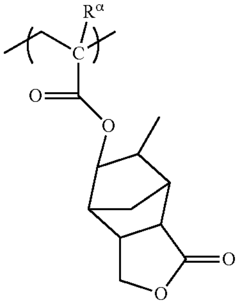
(a2-3-3)
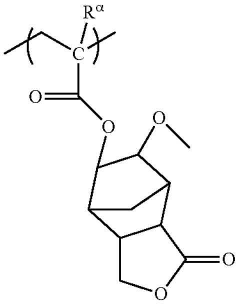
(a2-3-4)
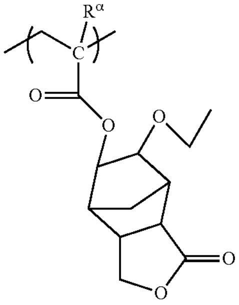
(a2-3-5)
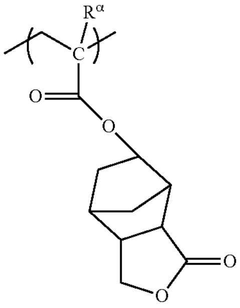
[Chemical Formula 37]
(a2-4-1)
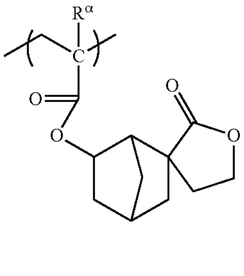

-continued
(a2-4-2)
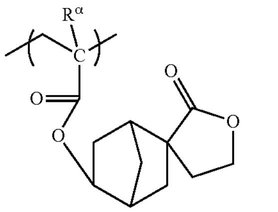
(a2-4-3)
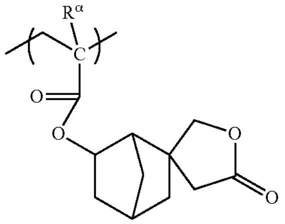
(a2-4-4)
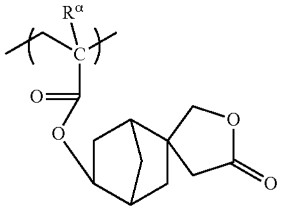
(a2-4-5)
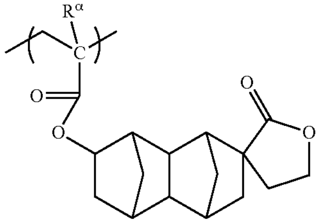
(a2-4-6)
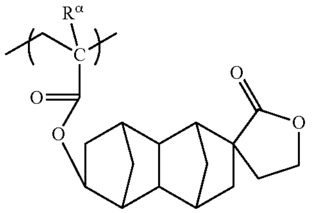
(a2-4-7)
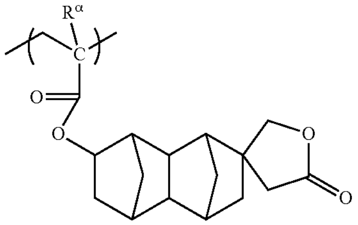
(a2-4-8)
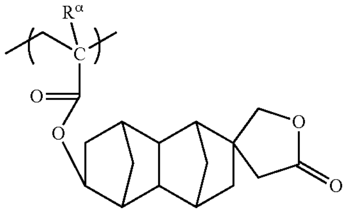
-continued
(a2-4-9)
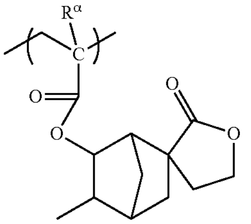
(a2-4-10)
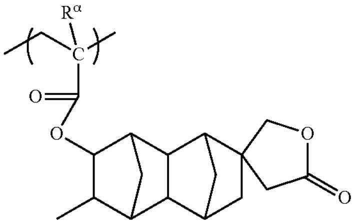
(a2-4-11)
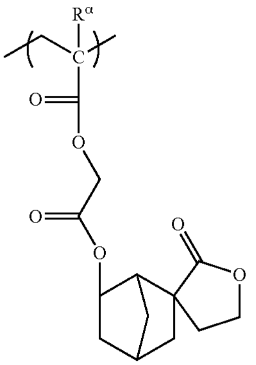
(a2-4-12)
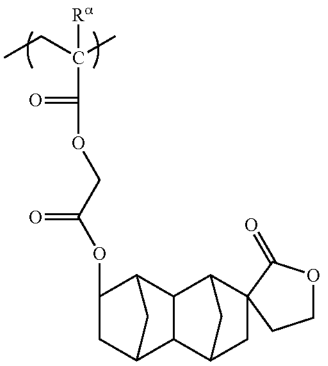
[Chemical Formula 38]
(a2-5-1)
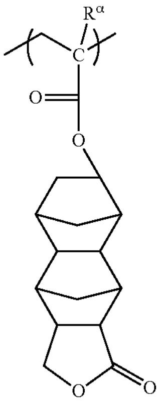

-continued (a2-5-2)

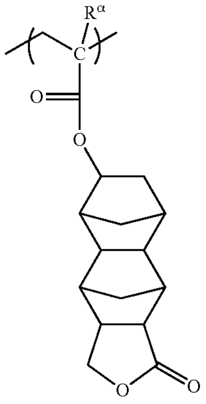

(a2-5-3)

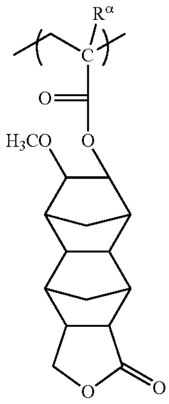

(a2-5-4)

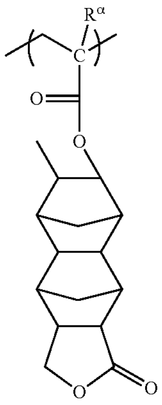

-continued (a2-5-5)

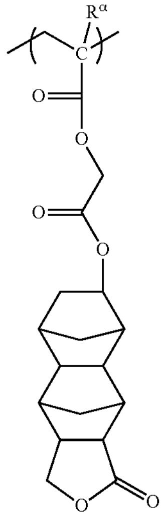

(a2-5-6)

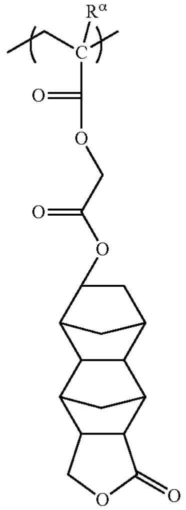

As the structural unit ($a2^L$), it is preferable to include at least one structural unit selected from the group consisting of structural units represented by the aforementioned general formulas (a2-1) to (a2-5), more preferably at least one structural unit selected from the group consisting of structural units represented by the aforementioned general formulas (a2-1) to (a2-3), and most preferably at least one structural unit selected from the group consisting of structural units represented by the aforementioned general formulas (a2-1) and (a2-3).

Specifically, it is preferable to use at least one structural unit selected from the group consisting of formulas (a2-1-1), (a2-1-2), (a2-2-1), (a2-2-7), (a2-2-12), (a2-2-14), (a2-3-1) and (a2-3-5).

In the component (A1), as the structural unit (a2), one type of structural unit may be used, or two or more types may be used in combination. For example, as the structural unit (a2), a structural unit ($a2^S$) may be used alone, or a structural unit ($a2^L$), or a combination of these structural units may be used. Further, as the structural unit ($a2^S$) or the structural unit ($a2^L$), either a single type of structural unit may be used, or two or more types may be used in combination.

When the component (A1) contains the structural unit (a2), the amount of the structural unit (a2) based on the combined total of all structural units constituting the component (A1) is preferably 1 to 80 mol %, more preferably 10 to 75 mol %, still more preferably 10 to 70 mol %, and most preferably 10 to 65 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties such as DOF and CDU and pattern shape can be improved.

(Structural Unit (a3))

The structural unit (a3) is a structural unit derived from an acrylate ester which may have the hydrogen atom bonded to the carbon atom on the α-position substituted with a substituent and contains a polar group-containing aliphatic hydrocarbon group.

When the component (A1) includes the structural unit (a3), the hydrophilicity of the component (A1) is enhanced, thereby contributing to improvement in resolution.

Examples of the polar group include a hydroxyl group, cyano group, carboxyl group, or hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups).

These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 39]

(a3-1)

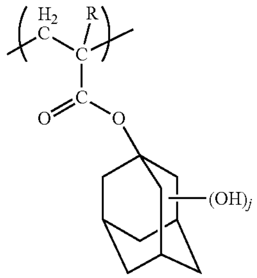

(a3-2)

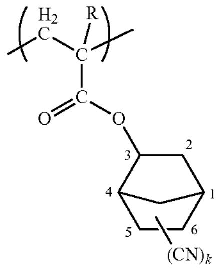

(a3-3)

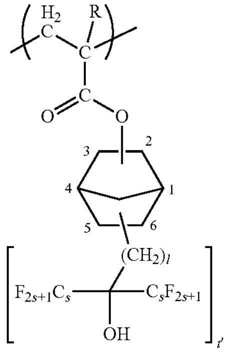

(a3-4)

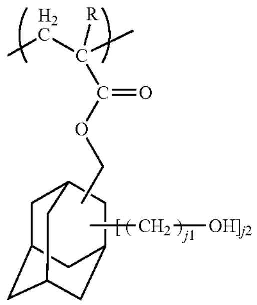

(a3-5)

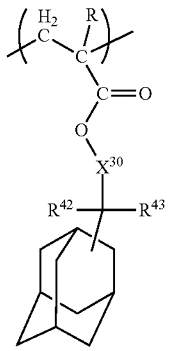

In the formulas, R is as defined above; j represents an integer of 1 to 3; k represents an integer of 1 to 3; t' represents an integer of 1 to 3; 1 represents an integer of 1 to 5; s represents an integer of 1 to 3; j1 represents an integer of 1 to 5; j2 represents an integer of 1 to 3; $X^{30}$ represents an divalent linking group; $R^{42}$ and $R^{43}$ each independently represent a hydrogen atom, an alkyl group of 1 to 10 carbon atoms, a hydroxyl group, or an alkyl group having at least one hydroxyl group as a substituent: at least one of $R^{42}$ and $R^{43}$ contains a hydroxyl group.

In general formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. 1 is preferably 1. s is preferably 1. Further, in formula (a3-3), it is preferable that a 2-norbonyl group or 3-norbonyl group be bonded to the terminal of the carboxy group of the acrylic acid. The fluorinated alkylalcohol is preferably bonded to the 5th or 6th position of the norbornyl group.

In general formula (a3-4), j1 is an integer of 0 to 5, preferably an integer of 0 to 2, more preferably 0 or 1, and most preferably 0. j2 is an integer of 1 to 3, is preferably 1 or 2, and is more preferably 1. Among these, a structural unit in which j1 is 0 or 1, j2 is 1, and a hydroxyl group is bonded to the 2nd position of the adamantyl group, is particularly preferable.

In formula (a3-5), $X^{30}$ is a divalent linking group which includes the same divalent linking group as described above for $Y^{22}$ in formula (a1-0-2). Among these, an alkylene group is preferable, and a methylene group or an ethylene group is particularly desirable.

In formula (a3-5), $R^{42}$ and $R^{43}$ each independently represent a hydrogen atom, an alkyl group of 1 to 10 carbon atoms, a hydroxyl group, or an alkyl group of 1 to 10 carbon atoms having at least one hydroxyl group as a substituent: at least one of $R^{42}$ and $R^{43}$ contains a hydroxyl group.

As the alkyl group of 1 to 10 carbon atom for $R^{42}$ and $R^{43}$, a chain-like alkyl group is preferable, and the chain-like alkyl group may be a linear or branched alkyl group.

Examples of the linear alkyl group include a methyl group, an ethyl group, a propyl group, a butyl group, a pentyl group, a hexyl group, a heptyl group, an octyl group, a nonyl group and a decyl group.

Specific examples of branched alkyl groups include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

As the alkyl group of 1 to 10 carbon atoms having at least one hydroxyl group as a substituent for $R^{42}$ and $R^{43}$, groups in which at least one hydrogen atom of the aforementioned alkyl groups for $R^{42}$ and $R^{43}$ has been substituted with a hydroxy group can be mentioned.

In the present invention, it is preferable that only one of $R^{42}$ and $R^{43}$ has a hydroxyl group, and a combination of the alkyl group and a hydroxyl group is particularly desirable.

As the structural unit (a3), one type of structural unit may be used, or two or more types may be used in combination.

When the component (A1) contains the structural unit (a3), the amount of the structural unit (a3) based on the combined total of all structural units constituting the component (A1) is preferably 1 to 50 mol %, more preferably 3 to 45 mol %, and still more preferably 5 to 40 mol %. When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

(Other Structural Units)

The component (A1) may also have a structural unit other than the above-mentioned structural units (a1) to (a3) (hereafter, referred to as "structural unit (a4)"), as long as the effects of the present invention are not impaired.

As the structural unit (a4), any other structural unit which cannot be classified as one of the above structural units (a1) to (a3) can be used without any particular limitation, and any of the multitude of conventional structural units used within resist resins for ArF excimer lasers or KrF excimer lasers (and particularly for ArF excimer lasers) can be used.

Preferable examples of the structural unit (a4) include a structural unit derived from an acrylate ester which contains a non-acid-dissociable aliphatic polycyclic group and may have the hydrogen atom bonded to the carbon atom on the α-position substituted with a substituent, a structural unit derived from a styrene monomer and a structural unit derived from a vinylnaphthalene monomer. Examples of this polycyclic group include the same groups as those described above in relation to the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 40]

(a4-1)

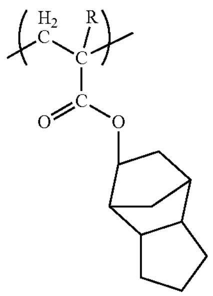

-continued (a4-2)

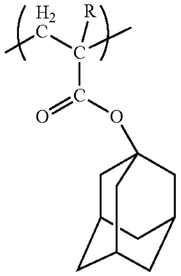

(a4-3)

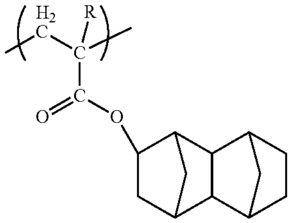

(a4-4)

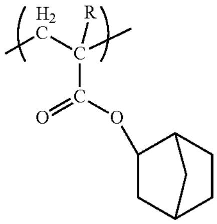

(a4-5)

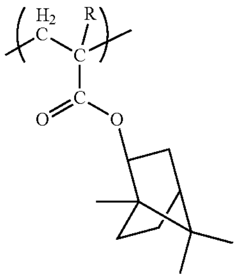

In the formulas, R is the same as defined above.

As the structural unit (a4), one type of structural unit may be used, or two or more types may be used in combination.

When the structural unit (a4) is included in the component (A1), the amount of the structural unit (a4) based on the combined total of all structural units constituting the component (A1) is preferably 1 to 20 mol %, more preferably 1 to 15 mol %, and still more preferably 1 to 10 mol %.

The component (A1) is preferably a copolymer containing the structural unit (a1).

Examples of such copolymers include a copolymer consisting of the structural units (a1) and (a2), a copolymer consisting of the structural units (a1) and (a3), and a copolymer consisting of the structural units (a1), (a2) and (a3).

In the present invention, as the component (A1), a copolymer that includes a combination of structural units represented by formula (A1-11) or (A1-12) shown below is particularly desirable. In the formula, R, $R^{11}$, $R^{29}$, s", j, e', A', $R^{12}$, and h are the same as defined above, and the plurality of R may be the same or different from each other.

[Chemical Formula 41]

(A1-11)

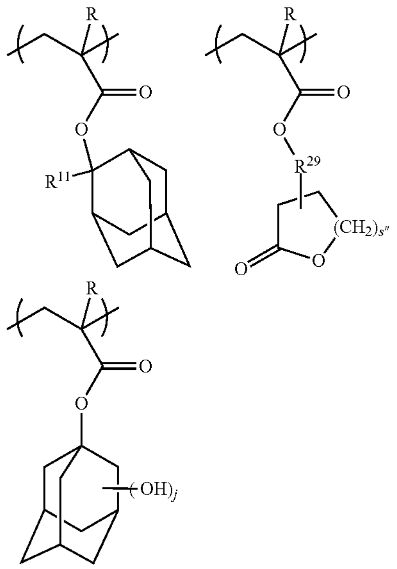

(A1-12)

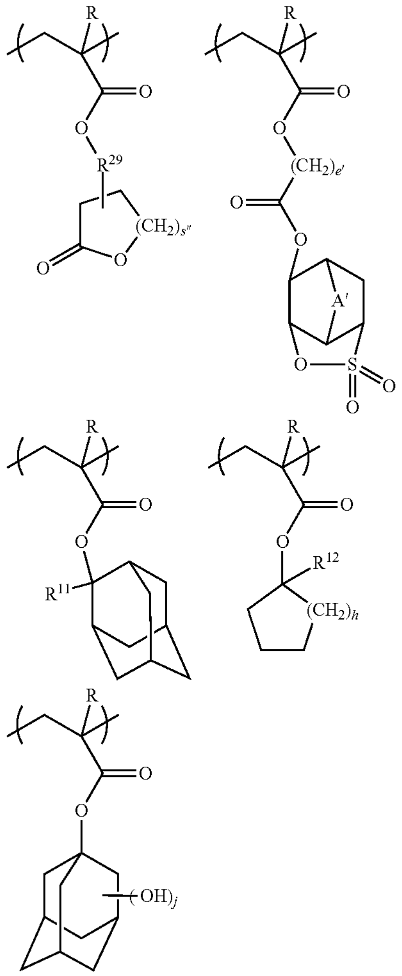

The weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,500 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (A1) is not particularly limited, but is preferably 1.0 to 5.0, more preferably 1.0 to 3.0, and most preferably 1.2 to 2.5.

Here, Mn is the number average molecular weight.

In the component (A), as the component (A1), one type may be used, or two or more types of compounds may be used in combination.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, various lithography properties are improved.

[Component (A2)]

As the component (A2), it is preferable to use a compound that has a molecular weight of at least 500 and less than 2,500, contains a hydrophilic group, and also contains an acid dissociable group described above in connection with the component (A1).

Specific examples include compounds containing a plurality of phenol skeletons in which a part of the hydrogen atoms within hydroxyl groups have been substituted with the aforementioned acid dissociable groups.

Examples of the component (A2) include low molecular weight phenolic compounds in which a portion of the hydroxyl group hydrogen atoms have been substituted with an aforementioned acid dissociable group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to say, the low molecular weight phenol compound is not limited to these examples. In particular, a phenol compound having 2 to 6 triphenylmethane skeletons is preferable in terms of resolution and LWR.

Also, there are no particular limitations on the acid dissociable group, and suitable examples include the groups described above.

As the component (A2), one type of resin may be used, or two or more types of resins may be used in combination.

In the resist composition of the present invention, as the component (A), one type may be used, or two or more types of compounds may be used in combination.

Of the examples shown above, as the component (A), it is preferable to use one containing the component (A1).

In the resist composition of the present invention, the amount of the component (A) can be appropriately adjusted depending on the thickness of the resist film to be formed, and the like.

<Component (B)>

In the resist composition of the present invention, the component (B) includes an acid generator (B1) containing a compound represented by general formula (b1-1) shown below (hereafter, this acid generator (B1) is referred to as "component (B1)").

[Chemical Formula 42]

$$X\text{-}Q^1\text{-}Y^1\text{—}SO_3^{\ominus}A^{\oplus} \quad (b1\text{-}1)$$

wherein, X represents a cyclic group of 3 to 30 carbon atoms which may have a substituent, provided that a ring skelton of the cyclic group contains an —$SO_2$— bond or an —O—$SO_2$— bond, and at least one carbon atom which is not adjacent to the —$SO_2$— bond or the —O—$SO_2$— bond has an oxygen atom as a substituent; $Q^1$ represents a divalent linking group or a single bond; $Y^1$ represents an alkylene group which may have a substituent or a fluorinated alkylene group which may have a substituent; and $A^+$ represents an organic cation.

In formula (b1-1), X represents a cyclic group of 3 to 30 carbon atoms which may have a substituent, provided that a ring skelton of the cyclic group contains an —$SO_2$-bond or an —O—$SO_2$— bond. In addition, the ring skelton of the cyclic group contains at least one carbon atom which is not adjacent to the —$SO_2$— bond or the —O—$SO_2$— bond and has an oxygen atom as a substituent.

Here, a expression "a ring skelton of a cyclic group contains an —$SO_2$— bond or an —O—$SO_2$— bond" means that —S— within —$SO_2$— or —O—S— within —O—$SO_2$— forms part of the ring skeleton. In the present invention, when a ring containing an —$SO_2$— bond or an —O—$SO_2$— bond is counted as a first ring, the cyclic group may be a monocyclic group composed of only the first ring, or a polycyclic group containing other ring structures.

The expression "at least one carbon atom which is not adjacent to the —$SO_2$— bond or the —O—$SO_2$— bond has an oxygen atom as a substituent" means that a carbon atom which forms part of the ring skeleton of the cyclic group as described above and is not adjacent to the —$SO_2$— bond or the —O—$SO_2$— bond which form part of the ring skeleton of the cyclic group is substituted with an oxygen atom. The oxygen atom as a substituent may be one oxygen atom, or 2 or more oxygen atoms. In the present invention, by virtue of a ring skelton of a cyclic group containing an oxygen atom as a substituent on a position which is not adjacent to the —$SO_2$— bond or the —O—$SO_2$— bond, polarity of the cyclic group and the anion moiety represented by formula (b1-1) becomes high, and diffusion of the acid generator can be preferably controlled.

The number of carbon atoms within the cyclic group is within a range from 3 to 30, preferably within a range from 4 to 20, more preferably from 4 to 15, and most preferably from 4 to 12. Herein, the number of carbon atoms refers to the number of carbon atoms constituting the ring skeleton, excluding the number of carbon atoms within a substituent.

The cyclic group may be either an aliphatic cyclic group or an aromatic cyclic group, and is preferably an aliphatic cyclic group.

The alicyclic hydrocarbon group may be either a monocyclic group or a polycyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic group may have a substituent. Examples of the substituent include an alkyl group of 1 to 6 carbon atoms, an alkoxy group of 1 to 6 carbon atoms, a halogenated alkyl group of 1 to 6 carbon atoms, a halogen atom, a hydroxyl group, —COOR", —OC(=O)R", a hydroxyalkyl group and a cyano group (wherein R" represents a hydrogen atom or an alkyl group).

As the alkyl group of 1 to 6 carbon atoms, alkoxy group of 1 to 6 carbon atoms, halogenated alkyl group of 1 to 6 carbon atoms, a halogen atom, —COOR", —OC(=O)R" and hydroxyalkyl group as a substituent, the same alkyl groups, alkoxy groups, halogen atoms, halogenated alkyl groups, —COOR", —OC(=O)R" and hydroxyalkyl groups as those described above as the substituent for the $—SO_2—$ containing cyclic group in the description of the structural unit (a2) can be mentioned.

Specific examples of X in the present invention include groups represented by general formulas (x1) to (x4) shown below.

[Chemical Formula 43]

(x1)

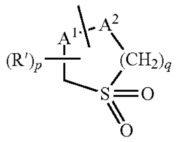

(x2)

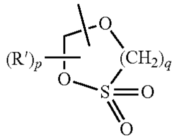

(x3)

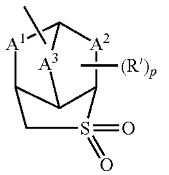

(x4)

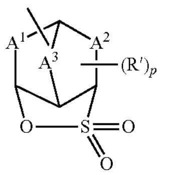

wherein, R' represents an alkyl group of 1 to 6 carbon atoms, an alkoxy group of 1 to 6 carbon atoms, a halogenated alkyl group of 1 to 6 carbon atoms, a halogen atom, a hydroxyl group, —COOR", —OC(=O)R", a hydroxyalkyl group or a cyano group, wherein R" represents a hydrogen atom or an alkyl group; $A^1$ to $A^3$ each independently represents $—CH_2—$ or —O—, provided that in formula (x1), at least one of $A^1$ and $A^2$ represents —O—, and in formulas (x3) and (x4), at least one of $A^1$ to $A^3$ represents —O—; p represents an integer of 0 to 4; and q represents an integer of 1 or 2.

In formulas (x1) to (x4), R' represents an alkyl group of 1 to 6 carbon atoms, an alkoxy group of 1 to 6 carbon atoms, a halogenated alkyl group of 1 to 6 carbon atoms, a halogen atom, a hydroxyl group, —COOR", —OC(=O)R", a hydroxyalkyl group or a cyano group which are the same as the substituent of the cyclic group as described above. In formulas (x1) to (x4), p is an integer of 0 to 4, preferably an integer of 0 to 2, more preferably 0 or 1, and most preferably 0.

In formula (x1) to (x4), $A^1$ to $A^3$ each independently represents $—CH_2—$ or —O—, provided that in formula (x1), at least one of $A^1$ and $A^2$ represents —O—, and in formulas (x3) and (x4), at least one of $A^1$ to $A^3$ represents —O—.

In formulas (x1) and (x2), q represents an integer of 1 or 2, and preferably an integer of 1.

As the group represented by formula (x4), a group represented by general formula (x4') shown below is preferable.

[Chemical Formula 44]

(x4')

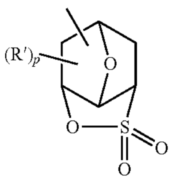

In the formula, R', R", and p are the same as defined in the aforementioned formula (x4).

Specific examples of cyclic groups represented by formulas (x1) to (x4) are shown below. In the following formulas, "Ac" represents an acetyl group.

[Chemical Formula 45]

(x1-1)

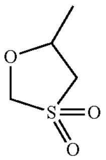

(x1-2)

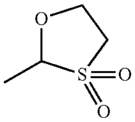

(x1-3)

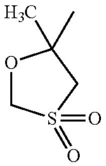

-continued
(x1-4)
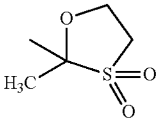
(x1-5)
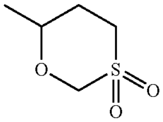
(x1-6)
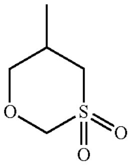
(x1-7)
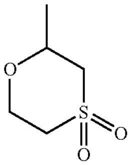
(x1-8)
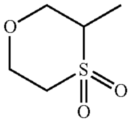
(x1-6)
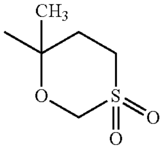
(x1-7)
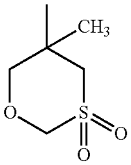
(x1-8)
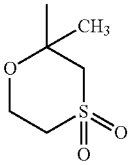
(x1-9)
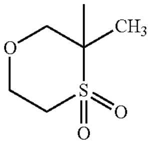
[Chemical Formula 46]
(x2-1)
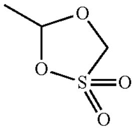
-continued
(x2-2)
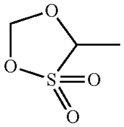
(x2-3)
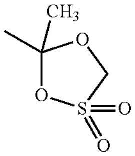
(x2-4)
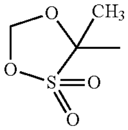
(x2-5)
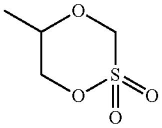
(x2-6)
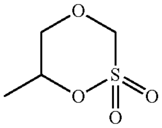
(x2-7)
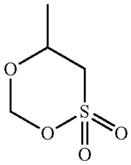
(x2-8)
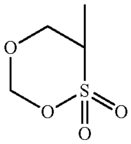
(x2-6)
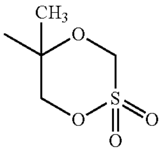
(x2-7)
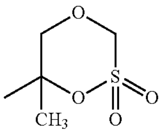
(x2-8)
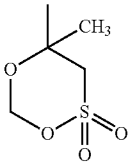

-continued
(x2-9)
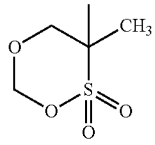
[Chemical Formula 47]
(x3-1)
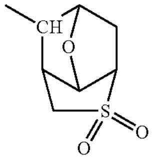
(x3-2)
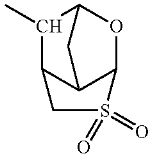
(x3-3)
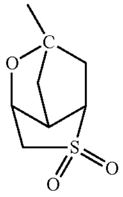
(x3-4)
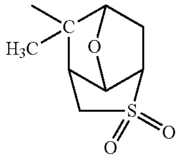
(x3-5)
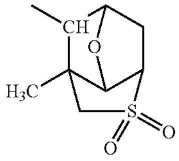
(x3-6)
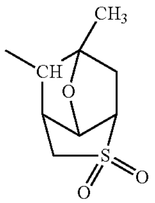
(x3-7)
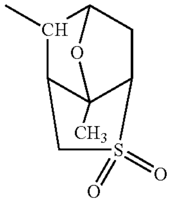
-continued
(x3-8)
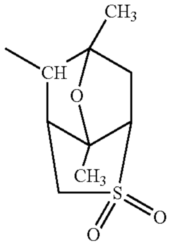
(x3-9)
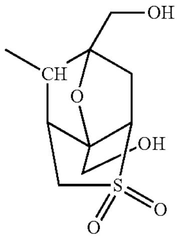
(x3-10)
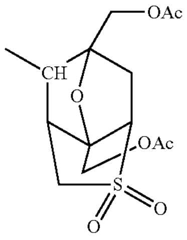
[Chemical Formula 48]
(x3-11)
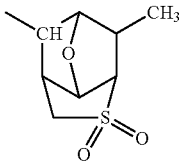
(x3-12)
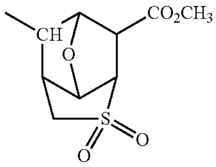
(x3-13)
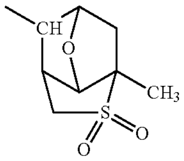
(x3-14)
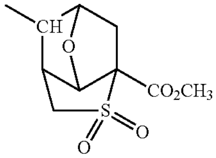

-continued
(x3-15)
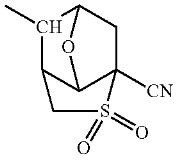
(x3-16)
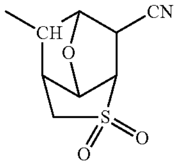
(x3-17)
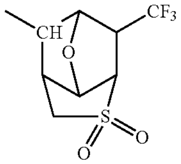
(x3-18)
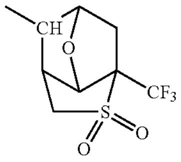
[Chemical Formula 49]
(x4-1)
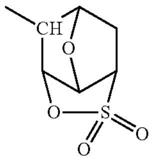
(x4-2)
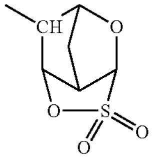
(x4-3)
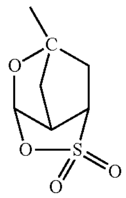
(x4-4)
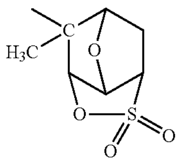
(x4-5)
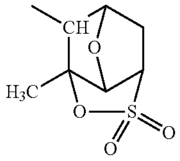
-continued
(x4-6)
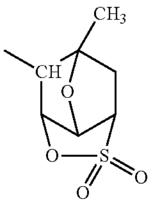
(x4-7)
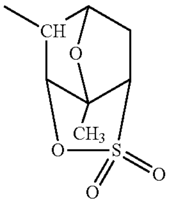
(x4-8)
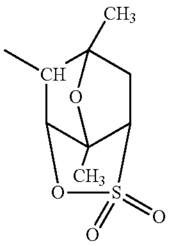
(x4-9)
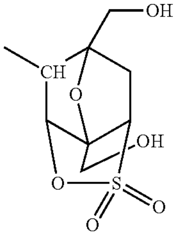
(x4-10)
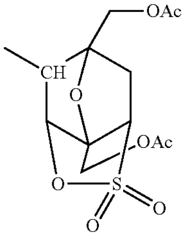
[Chemical Formula 50]
(x4-11)
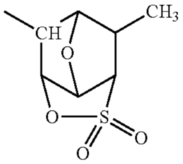
(x4-12)
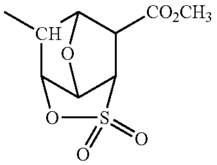

-continued (x4-13)

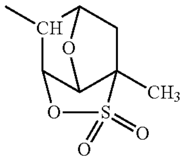

(x4-14)

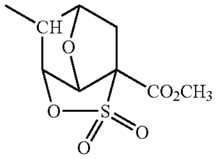

(x4-15)

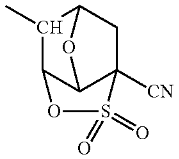

(x4-16)

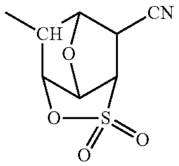

(x4-17)

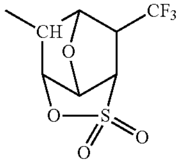

(x4-18)

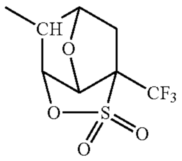

As a cyclic group for X, a group represented by the aforementioned formula (x4) is preferable, and a group represented by formula (x-4-1) is particularly desirable.

In general formula (b1-1), $Q^1$ represents a divalent linking group or a single bond.

As preferable examples of the divalent linking group for $Q^1$, a divalent hydrocarbon group which may have a substituent, and a divalent linking group containing a hetero atom can be given. Examples of the divalent liking group which may have a substituent and the linking group containing a hetero atom include the same groups as those described above for $Y^{22}$ in the aforementioned formula (a1-0-2).

Among these, as $Q^1$ in the present invention, a single bond or a divalent linking group containing a hetero atom is preferable, a divalent linking group containing an oxygen atom (—O—) or an ester bond (—C(=O)—O—) is more preferable, and a group represented by formula "$-A^0-O-[C(=O)]_{u1}-$" is particularly preferable. In the formula, $A^0$ represents a single bond or an alkylene group of 1 to 3 carbon atoms, and preferably a single bond or methylene group. In formula (b1-1), u1 represents 0 or 1, and preferably 1.

In formula (b1-1), $Y^1$ represents an alkylene group which may have a substituent or a fluorinated alkylene group which may have a substituent.

There are no particular limitations on the number of carbon atoms of the alkylene group or the fluorinated alkylene group, although the number of carbon atoms is preferably 1 to 4.

Specific examples of $Y^1$ include $-CF_2-$, $-CF_2CF_2-$, $-CF_2CF_2CF_2-$, $-CF(CF_3)CF_2-$, $-CF(CF_2CF_3)-$, $-C(CF_3)_2-$, $-CF_2CF_2CF_2CF_2-$, $-CF(CF_3)CF_2CF_2-$, $-CF_2CF(CF_3)CF_2-$, $-CF(CF_3)CF(CF_3)-$, $-C(CF_3)_2CF_2-$, $-CF(CF_2CF_3)CF_2-$, $-CF(CF_2CF_2CF_3)-$, $-C(CF_3)(CF_2CF_3)-$; $-CHF-$, $-CH_2CF_2-$, $-CH_2CH_2CF_2-$, $-CH_2CF_2CF_2-$, $-CH(CF_3)CH_2-$, $-CH(CF_2CF_3)-$, $-C(CH_3)(CF_3)-$, $-CH_2CH_2CH_2CF_2-$, $-CH_2CH_2CF_2CF_2-$, $-CH(CF_3)CH_2CH_2-$, $-CH_2CH(CF_3)CH_2-$, $-CH(CF_3)CH(CF_3)-$, $-C(CF_3)_2CH_2-$; $-CH_2-$, $-CH_2CH_2-$, $-CH_2CH_2CH_2-$, $-CH(CH_3)CH_2-$, $-CH(CH_2CH_3)-$, $-C(CH_3)_2-$, $-CH_2CH_2CH_2CH_2-$, $-CH(CH_3)CH_2CH_2-$, $-CH_2CH(CH_3)CH_2-$, $-CH(CH_3)CH(CH_3)-$, $-C(CH_3)_2CH_2-$, $-CH(CH_2CH_3)CH_2-$, $-CH(CH_2CH_2CH_3)-$, $-C(CH_3)(CH_2CH_3)-$.

As $Y^1$, a fluorinated alkylene group is preferable, and a fluorinated alkylene group in which the carbon atom bonded to the adjacent sulfur atom is fluorinated is particularly desirable. Examples of such fluorinated alkylene groups include $-CF_2-$, $-CF_2CF_2-$, $-CF_2CF_2CF_2-$, $-CF(CF_3)CF_2-$, $-CF_2CF_2CF_2CF_2-$, $-CF(CF_3)CF_2CF_2-$, $-CF_2CF(CF_3)CF_2-$, $-CF(CF_3)CF(CF_3)-$, $-C(CF_3)_2CF_2-$, $-CF(CF_2CF_3)CF_2-$; $-CH_2CF_2-$, $-CH_2CH_2CF_2-$, $-CH_2CF_2CF_2-$; $-CH_2CH_2CH_2CF_2-$, $-CH_2CH_2CF_2CF_2-$, $-CH_2CF_2CF_2CF_2-$.

Of these, $-CF_2-$, $-CF_2CF_2-$, $-CF_2CF_2CF_2-$, or $CH_2CF_2CF_2-$ are preferable, $-CF_2-$, $-CF_2CF_2-$ or $-CF_2CF_2CF_2-$ are more preferable, and $-CF_2-$ is particularly desirable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with groups other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxyl group.

As the anion moiety in the component (B1), an anion moiety represented by formula (b1-10) shown below is desirable. In formula (b1-10), p1 represents an integer of 1 to 3, preferably 1 or 2, and most preferably 1. p2 represents an integer of 1 to 3, preferably 1 or 2, and most preferably 1.

[Chemical Formula 51]

(b1-10)

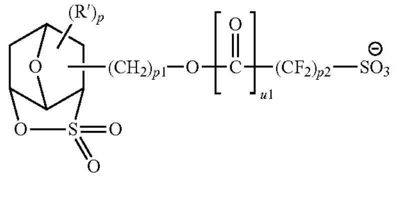

In the formula, R', p, and u1 is the same as defined above; p1 represents an integer of 1 to 3; p2 represents an integer of 1 to 3;

In formula (b1-1), $A^+$ represents an organic cation.

The organic cation for $A^+$ is not particularly limited, and an organic cation conventionally known as the cation moiety of a photo-decomposable base used as a quencher for a resist composition or the cation moiety of an onium salt acid generator for a resist composition can be used.

As the organic cation for $A^+$, for example, a cation moiety represented by general formula (c-1) or (c-2) shown below can be used.

[Chemical Formula 52]

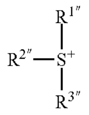

(c-1)

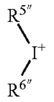

(c-2)

In the formulas, each of $R^{1}$" to $R^{3}$", $R^{5}$" and $R^{6}$" independently represents an aryl group or an alkyl group, provided that, in formula (c-1), two of $R^{1}$" to $R^{3}$" may be mutually bonded to form a ring with the sulfur atom.

In formula (c-1), $R^{1}$" to $R^{3}$" each independently represents an aryl group or an alkyl group. In formula (c-1), two of $R^{1}$" to $R^{3}$" may be bonded to each other to form a ring with the sulfur atom.

Further, among $R^{1}$" to $R^{3}$", it is preferable that at least one group represent an aryl group. Among $R^{1}$" to $R^{3}$", it is more preferable that two or more groups are aryl groups, and it is particularly desirable that all of $R^{1}$" to $R^{3}$" are aryl groups.

The aryl group for $R^{1}$" to $R^{3}$" is not particularly limited. For example, an aryl group having 6 to 20 carbon atoms may be used in which part or all of the hydrogen atoms of the aryl group may or may not be substituted with alkyl groups, alkoxy groups, halogen atoms or hydroxyl groups.

The aryl group is preferably an aryl group having 6 to 10 carbon atoms because it can be synthesized at a low cost. Specific examples thereof include a phenyl group and a naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

The halogen atom, with which hydrogen atoms of the aryl group may be substituted, is preferably a fluorine atom.

The alkyl group for $R^{1}$" to $R^{3}$" is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decyl group, and a methyl group is most preferable because it is excellent in resolution and can be synthesized at a low cost.

When two of $R^{1}$" to $R^{3}$" in formula (c-1) are bonded to each other to form a ring with the sulfur atom, it is preferable that the two of $R^{1}$" to $R^{3}$" form a 3- to 10-membered ring including the sulfur atom, and it is particularly desirable that the two of $R^{1}$" to $R^{3}$" form a 5- to 7-membered ring including the sulfur atom.

When two of $R^{1}$" to $R^{3}$" in formula (c-1) are bonded to each other to form a ring with the sulfur atom, the remaining one of $R^{1}$" to $R^{3}$" is preferably an aryl group. As examples of the aryl group, the same aryl groups as those described above for $R^{1}$" to $R^{3}$" can be used.

As preferable examples of the cation moiety represented by general formula (c-1), those represented by formulas (I-1-1) to (I-1-32) shown below can be given.

[Chemical Formula 53]

(I-1-1)

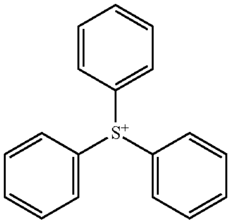

(I-1-2)

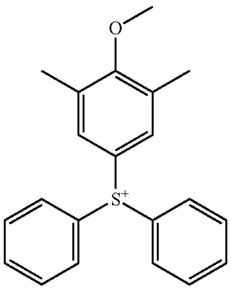

(I-1-3)

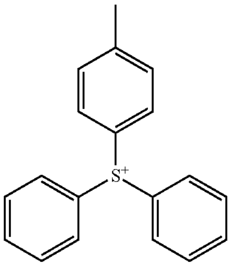

(I-1-4)

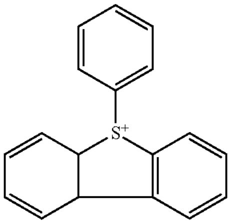

-continued
(I-1-5)
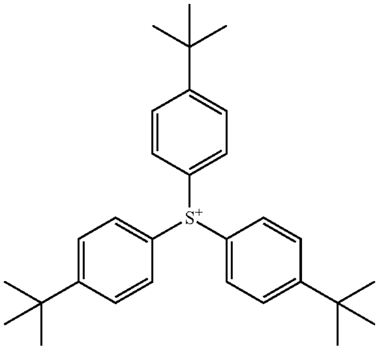
(I-1-6)
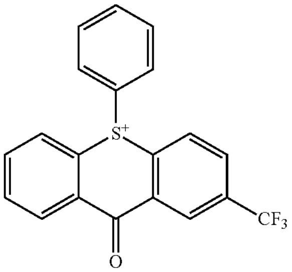
(I-1-7)
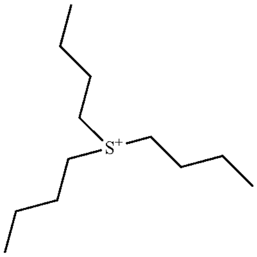
[Chemical Formula 54]
(I-1-8)
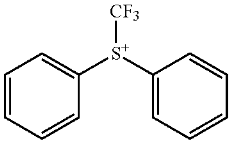
(I-1-9)
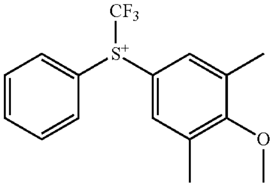
(I-1-10)
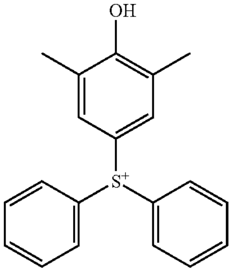
-continued
(I-1-11)
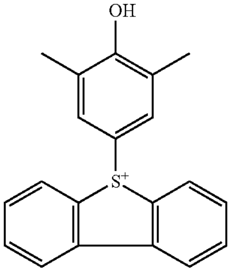
(I-1-12)
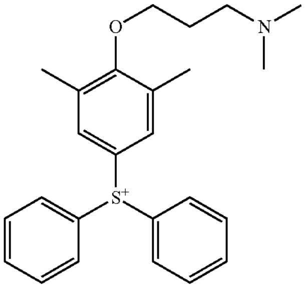
(I-1-13)
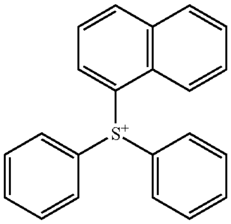
(I-1-14)
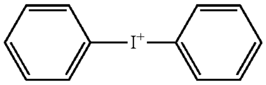
(I-1-15)
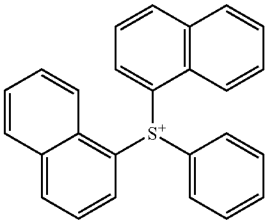
[Chemcial Formula 55]
(I-1-16)
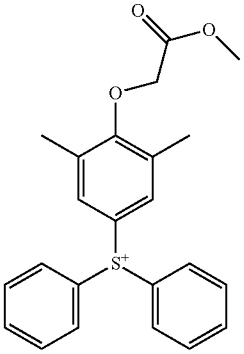

-continued
(I-1-17)
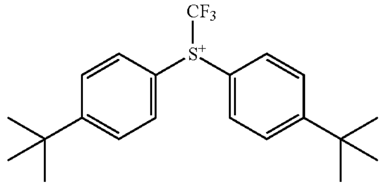
(I-1-18)
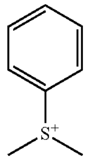
(I-1-19)
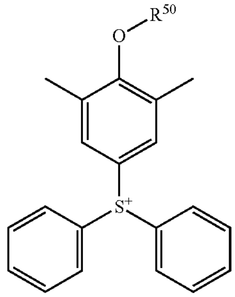
(I-1-20)
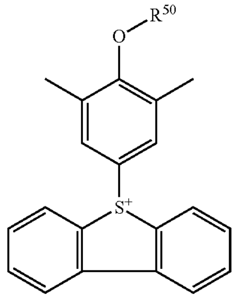
(I-1-21)
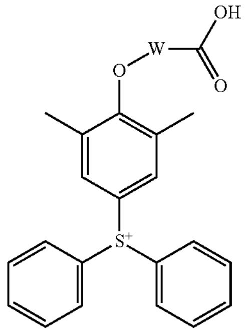
(I-1-22)
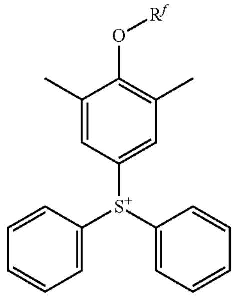
-continued
[Chemical Formula 56]
(I-1-23)
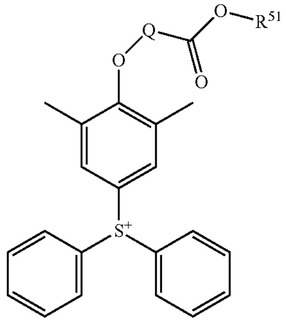
(I-1-24)
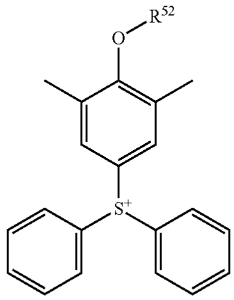
(I-1-25)
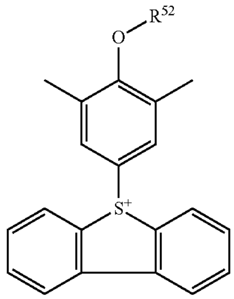
(I-1-26)
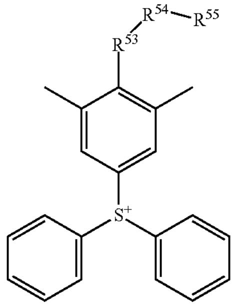
(I-1-27)
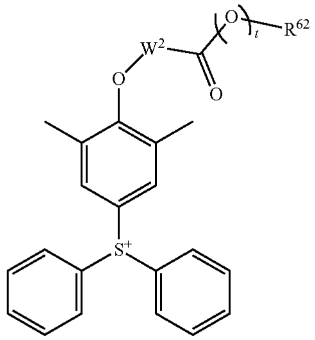

-continued

[Chemical Formula 57]

(I-1-28)

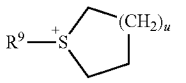

(I-1-29)

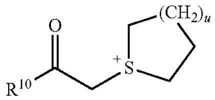

(I-1-30)

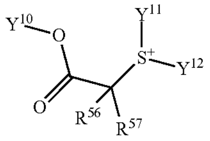

(I-1-31)

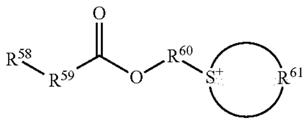

(I-1-32)

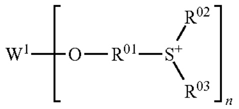

In formulas (I1-1-19) and (I-1-20), $R^{50}$ represents a group containing an acid dissociable, dissolution inhibiting group, and is preferably a group represented by the aforementioned formula (p1), (p1-1), or (p2), or a group in which a group represented by the aforementioned formula (1-1) to (1-9) or (2-1) to (2-6) is bonded to the oxygen atom of —$R^{91}$—C(═O)—O—. $R^{91}$ represents a single bond or a linear or branched alkylene group, and the alkylene group preferably has 1 to 5 carbon atoms.

In formula (I-1-21), W represents a divalent linking group, and examples thereof include the same divalent linking groups as those described above for $Y^{22}$ in the aforementioned formula (a1-0-2). Among these, a linear or branched alkylene group, a divalent aliphatic cyclic group or a divalent linking group containing a hetero atom is preferable, a linear or branched alkylene group is more preferable, and a linear alkylene group is still more preferable.

In formula (I-1-22), $R^f$ represents a fluorinated alkyl group, i.e., a group in which an unsubstituted alkyl group has part or all of the hydrogen atoms substituted with fluorine atoms. The unsubstituted alkyl group is preferably a linear or branched alkyl group, and more preferably a linear alkyl group.

In formula (I-1-23), Q represents a divalent linking group, and $R^{51}$ represents an organic group having a carbonyl group, an ester bond or a sulfonyl group.

Examples of the divalent linking group for Q include the same divalent linking groups as those described above for W. As Q, an alkylene group or a divalent linking group containing an ester bond is preferable, and an alkylene group or —$R^{92}$—C(═O)—O—$R^{93}$— [each of $R^{92}$ and $R^{93}$ independently represents an alkylene group] is more preferable.

The organic group having a carbonyl group, an ester bond or a sulfonyl group for $R^{51}$ may be either an aromatic hydrocarbon group or a aliphatic hydrocarbon group. Examples of the aromatic hydrocarbon group and the aliphatic hydrocarbon group include the same groups as those described below for $X^{01}$. Among these, as the organic group having a carbonyl group, an ester bond or a sulfonyl group for $R^{51}$, an aliphatic hydrocarbon group is preferable, a bulky aliphatic hydrocarbon group is more preferable, and a cyclic saturated hydrocarbon group is still more preferable. Preferable examples of $R^{51}$ include a group represented by any one of the aforementioned formulas (L1) to (L6) and (S1) to (S4), and a monocyclic or polycyclic group in which the hydrogen atoms bonded thereto have been substituted with an oxygen atom (═O).

In formulas (I-1-24) and (I-1-25), $R^{52}$ represents an alkyl group of 4 to 10 carbon atoms which is not an acid dissociable group. As $R^{52}$, a linear or branched alkyl group is preferable, and a linear alkyl group is more preferable.

In formula (I-1-26), $R^{53}$ represents a divalent group having a base dissociable portion, $R^{54}$ represents a divalent linking group, and $R^{55}$ represents a group having an acid dissociable group.

The base dissociable portion within $R^{53}$ refers to a portion which is dissociable by the action of an alkali developing solution (e.g., a 2.38% by weight aqueous solution of tetramethylammonium hydroxide (TMAH) at 23° C.). By the dissociation of the base dissociable portion, the solubility in an alkali developing solution is increased. The alkali developing solution may be any one of those generally used in the fields of lithography. It is preferable that the base dissociable portion is dissociated the action of a 2.38% by weight aqueous solution of tetramethylammonium hydroxide at 23° C.

The $R^{53}$ group may be either a group constituted of only a base dissociable portion, or a group in which a base dissociable portion is boned to a group or atom which is not base dissociable.

The base dissociable portion within the $R^{53}$ group is most preferably an ester group.

Examples of the group or atom which is not base dissociable for $R^{53}$ include the divalent linking groups described above for $Y^{22}$ in general formula (a1-0-2) for the structural unit (a1) and combinations of the linking groups (provided that groups which are base dissociable are excluded). The "combination of the linking groups" refer to a divalent linking group constituted of divalent linking groups bonded together. As such a "combination of linking groups", a combination of an alkylene group with a divalent linking group containing a hetero atom is preferable. However, it is preferable that the hetero atom is not adjacent to the atom within the base dissociable portion which has its bond cleaved by the action of a base.

The alkylene group is the same as defined for the linear or branched alkylene group for A in $Y^{22}$.

The hetero atom is most preferably an oxygen atom.

Among the above examples, $R^{53}$ is preferably a group in which a base dissociable portion is boned to a group or atom which is not base dissociable.

$R^{54}$ represents a divalent linking group, and examples thereof include the same divalent linking groups as those described above for $Y^{22}$.

Among these, an alkylene group or a divalent aliphatic cyclic group is preferable, and an alkylene group is particularly desirable.

$R^{55}$ represents a group having an acid dissociable group.

The acid dissociable group is an organic group which can be dissociated by the action of an acid. The acid dissociable group is not particularly limited, and any group which has been proposed as an acid dissociable, dissolution inhibiting group of a base resin for a chemically amplified resist can be used. Specific examples include the same acid dissociable, dissolution inhibiting groups as those described for the structural unit (a1), such as a cyclic or chain-like tertiary alkyl ester-type acid dissociable group or an acetal-type acid dissociable group (e.g., an alkoxyalkyl group). Among these, a tertiary alkyl ester-type acid dissociable group is particularly desirable.

The group having an acid dissociable group may be either the acid dissociable group itself, or a group in which an acid dissociable group is bonded to a group or atom which is not acid dissociable (a group or atom which remains bonded to the acid generator even after the dissociation of the acid dissociable group). Examples of the group or atom which is not acid dissociable include the same divalent linking groups as those described above for $Y^{22}$.

In formula (I-1-27), $W^2$ represents a single bond or a divalent linking group, t represents 0 or 1, and $R^{62}$ represents a group which is not dissociable by acid (hereafter, referred to as "acid non-dissociable group").

Examples of the divalent linking group for $W^2$ include the same divalent linking groups as those described above for $Y^{22}$. Among these, as $W^2$, a single bond is preferable.

t is preferably 0.

The acid non-dissociable group for $R^{622}$ is not particularly limited as long as it is a group which is not dissociable by acid. The acid non-dissociable group is preferably an acid non-dissociable hydrocarbon group which may have a substituent, more preferably a cyclic hydrocarbon group which may have a substituent, and still more preferably a group in which one hydrogen atom has been removed from adamantane.

In formulas (I-1-28) and (I-1-29), each of $R^9$ and $R^{19}$ independently represents a phenyl group or naphthyl group which may have a substituent, an alkyl group of 1 to 5 carbon atoms, an alkoxy group or a hydroxy group; and u represents an integer of 1 to 3, most preferably 1 or 2.

In formula (I-1-30), $Y^{10}$ represents a cyclic hydrocarbon group of 5 or more carbon atoms which may have a substituent, and is an acid dissociable group which may be dissociated by the action of an acid; each of $R^{56}$ and $R^{57}$ independently represents a hydrogen atom, an alkyl group or an aryl group, provided that $R^{56}$ and $R^{57}$ may be mutually bonded to form a ring; each of $Y^{11}$ and $Y^{12}$ independently represents an alkyl group or an aryl group, provided that $Y^{11}$ and $Y^{12}$ may be mutually bonded to form a ring.

$Y^{10}$ represents a cyclic hydrocarbon group of 5 or more carbon atoms which may have a substituent, and is an acid dissociable group which may be dissociated by the action of an acid. By virtue of the $Y^{10}$ group being a cyclic hydrocarbon group of 5 or more carbon atoms which may have a substituent, and is an acid dissociable group which may be dissociated by the action of an acid, various lithography properties such as resolution, LWR, exposure latitude (EL margin) and resist pattern are improved.

Examples of $Y^{10}$ include groups which form a cyclic tertiary alkyl ester with $—C(R^{56})(R^{57})—C(=O)—O—$.

A "tertiary alkyl ester" refers to a structure in which a tertiary carbon atom within a cyclic hydrocarbon group of 5 or more carbon atoms is bonded to the terminal oxygen atom of $—C(R^{56})(R^{57})—C(=O)—O—$. In this tertiary alkyl ester, the action of acid causes cleavage of the bond between the oxygen atom and the tertiary carbon atom.

The cyclic hydrocarbon group may have a substituent, and the carbon atom(s) within the substituent is not included in the number of carbon atoms of the "carbon atom of 5 or more carbon atoms".

Examples of the "aliphatic cyclic group" include monocyclic groups or polycyclic groups which have no aromaticity, and polycyclic groups are preferable.

The "aliphatic cyclic group" may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

As such aliphatic cyclic groups, groups in which two or more hydrogen atoms have been removed from a monocycloalkane or a polycycloalkane such as a bicycloalkane, tricycloalkane or tetracycloalkane which may or may not be substituted with an alkyl group of 1 to 5 carbon atoms, a fluorine atom or a fluorinated alkyl group, may be used. Specific examples include groups in which two or more hydrogen atoms have been removed from a monocycloalkane such as cyclopentane and cyclohexane; and groups in which two or more hydrogen atoms have been removed from a polycycloalkane such as adamantane, norbornane, isobornane, tricyclodecane or tetracyclododecane.

Each of $R^{56}$ and $R^{57}$ independently represents a hydrogen atom, an alkyl group or an aryl group.

Examples of the alkyl group or aryl group for $R^{56}$ and $R^{57}$ include the same alkyl groups and aryl groups as those described above for $R^{1}$" to $R^{3}$". Further, $R^{56}$ and $R^{57}$ may be mutually bonded to form a ring, like in the case of the aforementioned $R^{1}$" to $R^{3}$".

Among the above-mentioned examples, it is particularly desirable that both $R^{56}$ and $R^{57}$ represent a hydrogen atom.

Each of and $Y^{12}$ independently represents an alkyl group or an aryl group.

Examples of the alkyl group or aryl group for $Y^{11}$ and $Y^{12}$ include the same alkyl groups and aryl groups as those described above for $R^{1}$" to $R^{3}$".

It is particularly desirable that each of $Y^{11}$ and $Y^{12}$ represents a phenyl group or a naphthyl group. Further, $Y^{11}$ and $Y^{12}$ may be mutually bonded to form a ring, like in the case of the aforementioned $R^{1}$" to $R^{3}$".

In formula (I-1-31), $R^{58}$ represents an aliphatic cyclic group; $R^{59}$ represents a single bond or an alkylene group which may have a substituent; $R^{60}$ represents an arylene group which may have a substituent; and $R^{61}$ represents an alkylene group of 4 or 5 carbon atoms which may have a substituent.

The aliphatic cyclic group for $R^{58}$ may be either a monocyclic group or a polycyclic group, but is preferably a polycyclic group, more preferably a group in which one or more hydrogen atoms have been removed from a polycycloalkane, and most preferably a group in which one or more hydrogen atoms have been removed from adamantane.

The alkylene group for $R^{59}$ which may have a substituent is preferably a linear or branched alkylene group. As $R^{59}$, a single bond or an alkylene group of 1 to 3 carbon atoms is preferable.

The arylene group for $R^{60}$ preferably has 6 to 20 carbon atoms, more preferably 6 to 14 carbon atoms, and still more preferably 6 to 10 carbon atoms. Examples of the arylene group include a phenylene group, a biphenylene group, a fluorenylene group, a naphthylene group, an anthrylene group and a phenanthrene group. In terms of synthesis at low cost, a phenylene group or a naphthylene group is preferable.

In formula (I-1-32), $R^{01}$ represents an arylene group or an alkylene group; each of $R^{02}$ and $R^{03}$ independently represents an aryl group or an alkyl group, provided that $R^{02}$ and $R^{03}$ may be mutually bonded to form a ring with the sulfur atom, and at least one of $R^{01}$ to $R^{03}$ represents an arylene group or an aryl group; $W^1$ represents a linking group having a valency of n; and n represents 2 or 3.

The arylene group for $R^{01}$ is not particularly limited, and examples thereof include arylene groups of 6 to 20 carbon atoms in which part or all of the hydrogen atoms may be substituted. The alkylene group for $R^{01}$ is not particularly limited, and examples thereof include linear, branched or cyclic alkylene groups of 1 to 10 carbon atoms.

The aryl group for $R^{02}$ and $R^{03}$ is not particularly limited, and examples thereof include aryl groups of 6 to 20 carbon atoms in which part or all of the hydrogen atoms may be substituted. The alkyl group for $R^{02}$ and $R^{03}$ is not particularly limited, and examples thereof include linear, branched or cyclic alkyl groups of 1 to 10 carbon atoms.

Examples of the divalent linking group for $W^1$ include the same divalent linking groups as those described above for $Y^{22}$. The divalent linking group may be linear, branched or cyclic, but is preferably cyclic. Among these, an arylene group having two carbonyl groups, each bonded to the terminal thereof is preferable.

The trivalent linking group for $W^1$ is preferably an arylene group combined with three carbonyl groups.

In formula (c-2), $R^{5''}$ and $R^{6''}$ each independently represent an aryl group or alkyl group. At least one of $R^{5''}$ and $R^{6''}$ represents an aryl group. It is preferable that both of $R^{5''}$ and $R^{6''}$ represent an aryl group.

As the aryl group for $R^{5''}$ and $R^{6''}$, the same aryl groups as those described above for $R^{1''}$ to $R^{3''}$ can be used.

As the alkyl group for $R^{5''}$ and $R^{6''}$, the same alkyl groups as those described above for $R^{1''}$ to $R^{3''}$ can be used.

It is particularly desirable that both of $R^{5''}$ and $R^{6''}$ represents a phenyl group.

Further, as examples of the organic cation for $A^+$, organic cations represented by general formula (c-3) shown below can also be given.

[Chemical Formula 58]

(c-3)

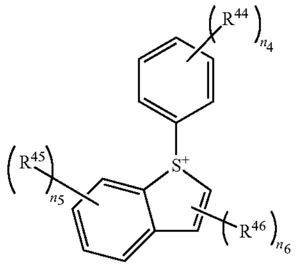

In the formula, each of $R^{44}$ to $R^{46}$ independently represents an alkyl group, an acetyl group, an alkoxy group, a carboxy group, a hydroxyl group or a hydroxyalkyl group; each of $n_4$ and $n_5$ independently represents an integer of 0 to 3; and $n_6$ represents an integer of 0 to 2.

With respect to $R^{44}$ to $R^{46}$, the alkyl group is preferably an alkyl group of 1 to 5 carbon atoms, more preferably a linear or branched alkyl group, and most preferably a methyl group, an ethyl group, a propyl group, an isopropyl group, an n-butyl group or a tert-butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

If there are two or more of an individual $R^{41}$ to $R^{46}$ group, as indicated by the corresponding value of $n_1$ to $n_6$, then the two or more of the individual $R^{41}$ to $R^{46}$ group may be the same or different from each other.

$n_4$ is preferably 0 to 2, and more preferably 0 or 1.

$n_5$ is preferably 0 or 1, and more preferably 0.

$n_6$ is preferably 0 or 1, and more preferably 0.

In the present invention, as the organic cation for $A^+$, an organic cation represented by the aforementioned formula (c-1) to (c-3) is preferable, and an organic cation represented by the aforementioned formula (c-1) is more preferable.

As the component (B1), one type of acid generator may be used alone, or two or more types may be used in combination.

In the resist composition of the present invention, the amount of the component (B1) within the component (B) is preferably 40% by weight or more, still more preferably 60% by weight or more, and may be even 100% by weight.

[Component (B2)]

In the resist composition of the present invention, if desired, the component (B) may further include an acid-generator component which cannot be classified as the component (B1) (hereafter, referred to as "component (B2)"), in addition to the component (B1).

The component (B2) is not particularly limited as long it does not fall under the definition of the component (B1), and any of the known acid generators used in conventional chemically amplified resist compositions can be used. Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As an onium salt acid generator, a compound represented by general formula (b-1) or (b-2) shown below can be used.

[Chemical Formula 59]

(b-1)

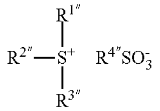

(b-2)

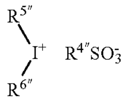

In the formulas above, $R^{1''}$ to $R^{3''}$, $R^{5''}$ and $R^{6''}$ each independently represent an aryl group or alkyl group, wherein two of $R^{1''}$ to $R^{3''}$ may be bonded to each other to form a ring with the sulfur atom; and $R^{4''}$ represents an alkyl group, a halogenated alkyl group, an aryl group or an alkenyl group which may have a substituent, with the provision that at least one of $R^{1''}$ to $R^{3''}$ represents an aryl group, and at least one of $R^{5''}$ and $R^{6''}$ represents an aryl group.

In general formula (b-1), $R^{1''}$ to $R^{3''}$ are the same as defined for $R^{5''}$ to $R^{6''}$ in general formula (b-2).

In formulas (b-1) and (b-2), $R^{4''}$ represents an alkyl group, a halogenated alkyl group, an aryl group or an alkenyl group which may have a substituent.

The alkyl group for $R^{4''}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms.

As an example of the halogenated alkyl group for $R^{4''}$, a group in which part of or all of the hydrogen atoms of the aforementioned linear, branched or cyclic alkyl group have been substituted with halogen atoms can be given. Examples of the aforementioned halogen atom include a fluorine atom, a chlorine atom, a bromine atom and an iodine atom, and a fluorine atom is preferable.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%.

Higher halogenation ratio is preferable because the acid strength increases.

The aryl group for $R^{4''}$ is preferably an aryl group of 6 to 20 carbon atoms.

The alkenyl group for $R^{4''}$ is preferably an alkenyl group of 2 to 10 carbon atoms.

With respect to $R^{4''}$, the expression "may have a substituent" means that part of or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4''}$ may have one substituent, or two or more substituents.

Examples of the substituent include a halogen atom, a hetero atom, an alkyl group, and a group represented by the formula $X^{01}$-$Q^{01}$- (in the formula, $Q^{01}$ represents a divalent linking group containing an oxygen atom; and $X^{01}$ represents a hydrocarbon group of 3 to 30 carbon atoms which may have a substituent).

Examples of halogen atoms and alkyl groups as substituents for $R^{4''}$ include the same halogen atoms and alkyl groups as those described above with respect to the halogenated alkyl group for $R^{4''}$.

Examples of hetero atoms include an oxygen atom, a nitrogen atom, and a sulfur atom.

In the group represented by formula $X^{01}$-$Q^{01}$-, $Q^{01}$ represents a divalent linking group containing an oxygen atom.

$Q^{01}$ may contain an atom other than an oxygen atom. Examples of atoms other than oxygen include a carbon atom, a hydrogen atom, a sulfur atom and a nitrogen atom. Examples of divalent linkage groups containing an oxygen atom include non-hydrocarbon, oxygen atom-containing linkage groups such as an oxygen atom (an ether bond; —O—), an ester bond (—C(=O)—O—), an amido bond (—C(=O)—NH—), a carbonyl group (—C(=O)—) and a carbonate group (—O—C(=O)—O—); and a combination of any of the aforementioned non-hydrocarbon, oxygen atom-containing linkage groups with an alkylene group.

Specific examples of the combinations of the aforementioned non-hydrocarbon, oxygen atom-containing linkage groups with anlkylene groups include —$R^{91}$—O—, —$R^{92}$—O—C(=O)— and —C(=O)—O—$R^{93}$—O—C(=O)— (in the formulas, $R^{91}$ to $R^{93}$ each independently represent an alkylene group.)

The alkylene group for $R^{91}$ to $R^{93}$ is preferably a linear or branched alkylene group, and preferably has 1 to 12 carbon atoms, more preferably 1 to 5, and most preferably 1 to 3.

Specific examples of the alkylene group include a methylene group [—$CH_2$—]; alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$— and —$C(CH_2CH_3)_2$—; an ethylene group [—$CH_2CH_2$-]; alkylethylene groups such as —$CH(CH_3)CH_2$—, —$CH(CH_3)CH(CH_3)$—, —$C(CH_3)_2CH_2$— and —$CH(CH_2CH_3)CH_2$—; a trimethylene group (n-propylene group) [—$CH_2CH_2CH_2$-]; alkyltrimethylene groups such as —$CH(CH_3)CH_2CH_2$— and —$CH_2CH(CH_3)CH_2$—; a tetramethylene group [—$CH_2CH_2CH_2CH_2$-]; alkyltetramethylene groups such as —$CH(CH_3)CH_2CH_2CH_2$— and —$CH_2CH(CH_3)CH_2CH_2$—; and a pentamethylene group [—$CH_2CH_2CH_2CH_2CH_2$—].

$Q^1$ is preferably a divalent linking group containing an ester linkage or ether linkage, and more preferably a group of —$R^{91}$—O—, —$R^{92}$—O—C(=O)— or —C(=O)—O—$R^{93}$—O—C(=O)—.

In the group represented by the formula $X^{01}$-$Q^{01}$-, the hydrocarbon group for $X^{01}$ may be either an aromatic hydrocarbon group or an aliphatic hydrocarbon group.

The aromatic hydrocarbon group is a hydrocarbon group having an aromatic ring. The aromatic hydrocarbon group preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and most preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned heteroatom can be used.

In the latter example, as the substituent for the aromatic hydrocarbon group, an alkyl group, an alkoxy group, a halogen atom, a halogenated alkyl group, a hydroxyl group, an oxygen atom (=O) or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Example of the halogenated alkyl group as the substituent for the aromatic hydrocarbon group includes a group in which part or all of the hydrogen atoms within the aforementioned alkyl group have been substituted with the aforementioned halogen atoms.

The aliphatic hydrocarbon group for $X^{01}$ may be either a saturated aliphatic hydrocarbon group, or an unsaturated aliphatic hydrocarbon group. Further, the aliphatic hydrocarbon group may be linear, branched or cyclic.

In the aliphatic hydrocarbon group for $X^{01}$, part of the carbon atoms constituting the aliphatic hydrocarbon group may be substituted with a substituent group containing a hetero atom, or part or all of the hydrogen atoms constituting the aliphatic hydrocarbon group may be substituted with a substituent group containing a hetero atom.

As the "hetero atom" for $X^{01}$, there is no particular limitation as long as it is an atom other than carbon and hydrogen. Examples of hetero atoms include a halogen atom, an oxygen atom, a sulfur atom and a nitrogen atom. Examples of the halogen atom include a fluorine atom, a chlorine atom, an iodine atom and a bromine atom.

The substituent group containing a hetero atom may consist of a hetero atom, or may be a group containing a group or atom other than a hetero atom.

Specific examples of the substituent group for substituting a part of the carbon atoms include —O—, —C(=O)—O—, —C(=O)—, —O—C(=O)—O—, —C(=O)—NH—, —NH— (the H may be substituted with a substituent such as an alkyl group or an acyl group), —S—, $—S(=O)_2—$ and $—S(=O)_2—O—$. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (=O) and a cyano group.

The aforementioned alkoxy group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5, still more preferably 2 to 4, and most preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12.

As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, $—S(=O)_2—$ or $—S(=O)_2—O—$. Specific examples of such aliphatic cyclic groups include groups represented by formulas (L1) to (L6) and (S1) to (S4) shown below, provided that those which fall under the definition of X in formula (b1-1) are excluded.

[Chemical Formula 60]

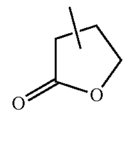

(L1)

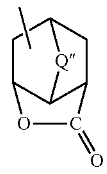

(L2)

-continued (L3)

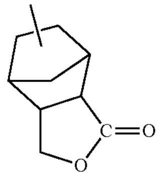

(L4)

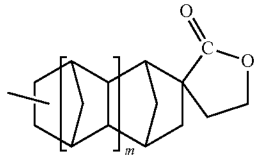

(L5)

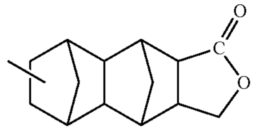

(L6)

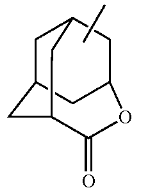

(S1)

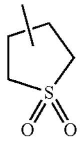

(S2)

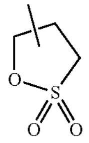

(S3)

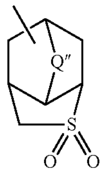

(S4)

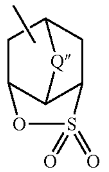

In the formulas, Q" represents an alkylene group of 1 to 5 carbon atoms, —O—, —S—, —O—$R^{94}$— or —S—$R^{95}$— ($R^{94}$ and $R^{95}$ each independently represent an alkylene group of 1 to 5 carbon atoms); and m represents 0 or 1.

As the alkylene group for Q", $R^{94}$ and $R^{95}$, the same alkylene groups as those described above for $R^{91}$ to $R^{93}$ can be used.

In these aliphatic cyclic groups, part of the hydrogen atoms bonded to the carbon atoms constituting the ring structure may be substituted with a substituent. Examples of substituents include an alkyl group, an alkoxy group, a halogen atom, a halogenated alkyl group, a hydroxyl group and an oxygen atom (═O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting part or all of the hydrogen atoms can be used.

In the present invention, as $X^{01}$, a cyclic group which may have a substituent is preferable.

The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by the aforementioned formulas (L2) to (L6), (S3) and (S4) are preferable.

In the present invention, $R^{4"}$ preferably has $X^{01}$-$Q^{01}$- as a substituent. In this case, $R^{4"}$ is preferably a group represented by formula $X^{01}$-$Q^{01}$-$Y^{01}$- [wherein $Q^{01}$ and $X^{01}$ are the same as defined above; and $Y^{01}$ represents an alkylene group of 1 to 4 carbon atoms which may have a substituent, or a fluorinated alkylene group of 1 to 4 carbon atoms which may have a substituent].

In the group represented by the formula $X^{01}$-$Q^{01}$-$Y^{01}$, $Y^{01}$ is the same as defined for $Y^1$ in formula (b1-1).

Specific examples of suitable onium salt acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts is replaced by an alkyl sulfonate such as methanesulfonate, n-propanesulfonate, n-butanesulfonate, n-octanesulfonate, 1-adamantanesulfonate, or 2-norbornanesulfonate, d-camphor-10-sulfonate, benzenesulfonate, perfluorobenzenesulfonate, or p-toluenesulfonate.

Furthermore, onium salts in which the anion moiety of these onium salts are replaced by an anion moiety represented by any one of formulas (b1) to (b8) shown below can be used.

[Chemical Formula 61]

(b1)

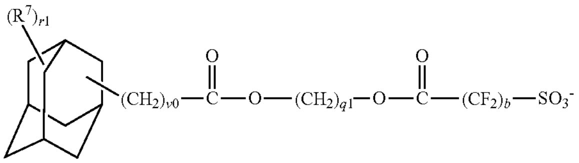

(b2)

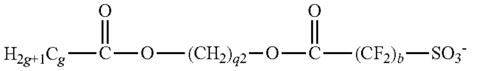

(b3)

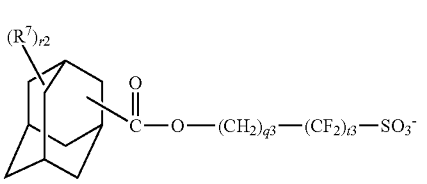

(b4)

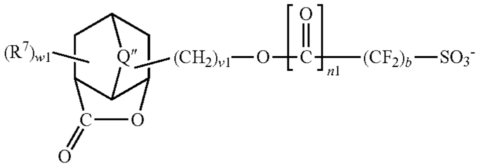

(b5)

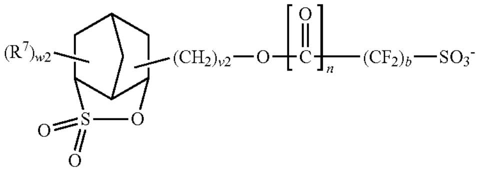

-continued (b6)

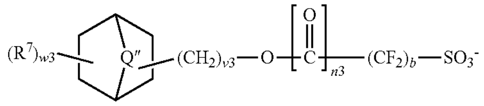

(b7)

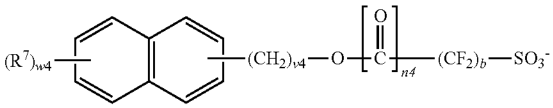

(b8)

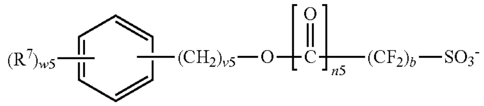

In the formulas, b represents an integer of 1 to 3; each of q1 and q2 independently represents an integer of 1 to 5; q3 represents an integer of 1 to 12; t3 represents an integer of 1 to 3; each of r1 and r2 independently represents an integer of 0 to 3; g represents an integer of 1 to 20; $R^7$ represents a substituent; each of n1 to n5 independently represents 0 or 1; each of v0 to v5 independently represents an integer of 0 to 3; each of w1 to w5 independently represents an integer of 0 to 3; and Q" is the same as defined above.

As the substituent for $R^7$, the same groups as those which the aforementioned aliphatic hydrocarbon group or aromatic hydrocarbon group for $X^{01}$ may have as a substituent can be used.

If there are two or more of the $R^7$ group, as indicated by the values r1, r2, and w1 to w5, then the two or more of the $R^7$ groups may be the same or different from each other.

Further, onium salt-based acid generators in which the anion moiety in general formula (b-1) or (b-2) is replaced by an anion moiety represented by general formula (b-3) or (b-4) shown below (the cation moiety is the same as (b-1) or (b-2)) may be used.

[Chemical Formula 62]

(b-3)

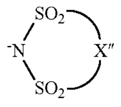

(b-4)

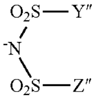

In the formulas, X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved.

The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Furthermore, as an onium salt-based acid generator, a sulfonium salt having a cation moiety represented by general formula (c-3) shown above may be used.

The anion moiety of the sulfonium salt having a cation moiety represented by the aforementioned general formula (c-3) is not particularly limited as long it does not fall under the definition of the anion moiety in the aforementioned general formula (b1-1), and the same anion moieties for onium salt-based acid generators which have been proposed may be used. Examples of such anion moieties include fluorinated alkylsulfonic acid ions such as anion moieties ($R^{4}$"$SO_3^-$) for onium salt-based acid generators represented by general formula (b-1) or (b-2) shown above; and anion moieties represented by general formula (b-3) or (b-4) shown above.

In the present description, an oximesulfonate-based acid generator is a compound having at least one group represented by general formula (B-1) shown below, and has a feature of generating acid by irradiation. Such oximesulfonate acid generators are widely used for a chemically amplified resist composition, and can be appropriately selected.

[Chemical Formula 63]

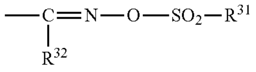

(B-1)

In the formula, $R^{31}$ and $R^{32}$ each independently represent an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. As the alkyl group or aryl group for $R^{32}$, the same alkyl groups or aryl groups as those described above for $R^{31}$ can be used.

As $R^{32}$, a cyano group, an alkyl group of 1 to 8 carbon atoms having no substituent or a fluorinated alkyl group of 1 to 8 carbon atoms is particularly desirable.

Preferable examples of the oxime sulfonate-based acid generator include compounds represented by general formula (B-2) or (B-3) shown below.

[Chemical Formula 64]

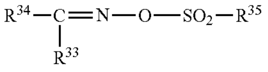

(B-2)

In the formula, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 65]

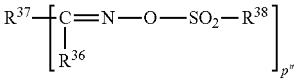

(B-3)

In the formula, $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenantryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Furthermore, as preferable examples, the following can be used.

[Chemical Formula 66]

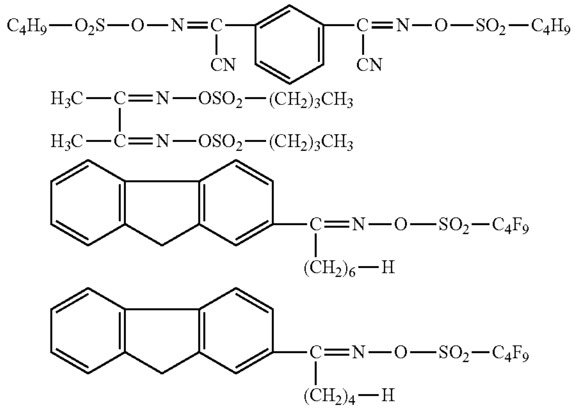

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used. Furthermore, as poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl) hexane, 1,10-bis(phenylsulfonyldiazomethylsulfonyl) decane, 1,2-bis(cyclohexylsulfonyldiazomethylsulfonyl) ethane, 1,3-bis(cyclohexylsulfonyldiazomethylsulfonyl)

propane, 1,6-bis(cyclohexylsulfonyldiazomethylsulfonyl)hexane, and 1,10-bis(cyclohexylsulfonyldiazomethylsulfonyl)decane, may be mentioned.

As the component (B2), one type of acid generator may be used, or two or more types may be used in combination.

As the component (B), one type of acid generator may be used, or two or more types may be used in combination.

In the resist composition of the present invention, the amount of the component (B) relative to 100 parts by weight of the component (A) is preferably 1 to 70 parts by weight, more preferably 3 to 60 parts by weight, and most preferably 5 to 50 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Component—Component (D)>

The resist composition of the present invention may contain a basic-compound component (D) (hereafter referred to as the component (D)) as an optional component. In the present invention, the component (D) functions as an acid diffusion control agent, i.e., a quencher which traps the acid generated from the component (B) upon exposure. In the present invention, a "basic compound" refers to a compound which is basic relative to the component (B).

In the present invention, the component (D) may be a basic compound (D1) (hereafter, referred to as "component (D1)") which has a cation moiety and an anion moiety, or a basic compound (D2) (hereafter, referred to as "component (D2)") which does not fall under the definition of component (C1).

[Component (D1)]

In the present invention, it is preferable that the component (D1) include at least one member selected from the group consisting of a compound (d1-1) represented by general formula (d1-1) shown below (hereafter, referred to as "component (d1-1)"), a compound (d1-2) represented by general formula (d1-2) shown below (hereafter, referred to as "component (d1-2)") and a compound (d1-3) represented by general formula (d1-3) shown below (hereafter, referred to as "component (d1-3)").

[Chemical Formula 67]

(d1-1)

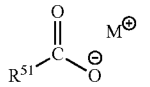

(d1-2)

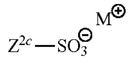

(d1-3)

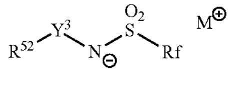

In the formulas, $R^{51}$ represents a hydrocarbon group which may have a substituent; $Z^{2c}$ represents a hydrocarbon group of 1 to 30 carbon atoms which may have a substituent (provided that the carbon adjacent to S has no fluorine atom as a substituent); $R^{52}$ represents an organic group; $Y^3$ represents a linear, branched or cyclic alkylene group or an arylene group; Rf represents a hydrocarbon group containing a fluorine atom; and each $M^+$ independently represents a sulfonium or iodonium cation having no aromaticity.

[Component (d1-1)]

Anion Moiety

In formula (d1-1), $R^{51}$ represents a hydrocarbon group which may have a substituent.

The hydrocarbon group for $R^{51}$ which may have a substituent may be either an aliphatic hydrocarbon group or an aromatic hydrocarbon group, and the same aliphatic hydrocarbon groups and aromatic hydrocarbon groups as those described above for the aforementioned $X^{01}$ in the component (B) can be used.

Among these, as the hydrocarbon group for $R^{51}$ which may have a substituent, an aromatic hydrocarbon group which may have a substituent or an aliphatic cyclic group which may have a substituent is preferable, and a phenyl group or a naphthyl group which may have a substituent, or a group in which one or more hydrogen atoms have been removed from a polycycloalkane such as adamantane, norbornane, isobornane, tricyclodecane or tetracyclododecane is more preferable.

As the hydrocarbon group for $R^{51}$ which may have a substituent, a linear, branched or alicyclic alkyl group or a fluorinated alkyl group is also preferable.

The linear, branched, or alicyclic alkyl group for $R^{51}$ preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group, a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group, and an alicyclic alkyl group such as a norbornyl group or an adamantyl group.

The fluorinated alkyl group for $R^{51}$ may be either chain-like or cyclic, but is preferably linear or branched.

The fluorinated alkyl group preferably has 1 to 11 carbon atoms, more preferably 1 to 8, and still more preferably 1 to 4. Specific examples include a group in which part or all of the hydrogen atoms constituting a linear alkyl group (such as a methyl group, an ethyl group, a propyl group, a butyl group, a pentyl group, a hexyl group, a heptyl group, an octyl group, a nonyl group or a decyl group) have been substituted with fluorine atom(s), and a group in which part or all of the hydrogen atoms constituting a branched alkyl group (such as a 1-methylethyl group, a 1-methylpropyl group, a 2-methylpropyl group, a 1-methylbutyl group, a 2-methylbutyl group or a 3-methylbutyl group) have been substituted with fluorine atom(s).

The fluorinated alkyl group for $R^{51}$ may contain an atom other than fluorine. Examples of the atom other than fluorine include an oxygen atom, a carbon atom, a hydrogen atom, an oxygen atom, a sulfur atom and a nitrogen atom.

Among these, as the fluorinated alkyl group for $R^{51}$, a group in which part or all of the hydrogen atoms constituting a linear alkyl group have been substituted with fluorine atom(s) is preferable, and a group in which all of the hydrogen atoms constituting a linear alkyl group have been substituted with fluorine atoms (i.e., a perfluoroalkyl group) is more preferable.

Specific examples of preferable anion moieties for the component (d1-1) are shown below.

[Chemical Formula 68]

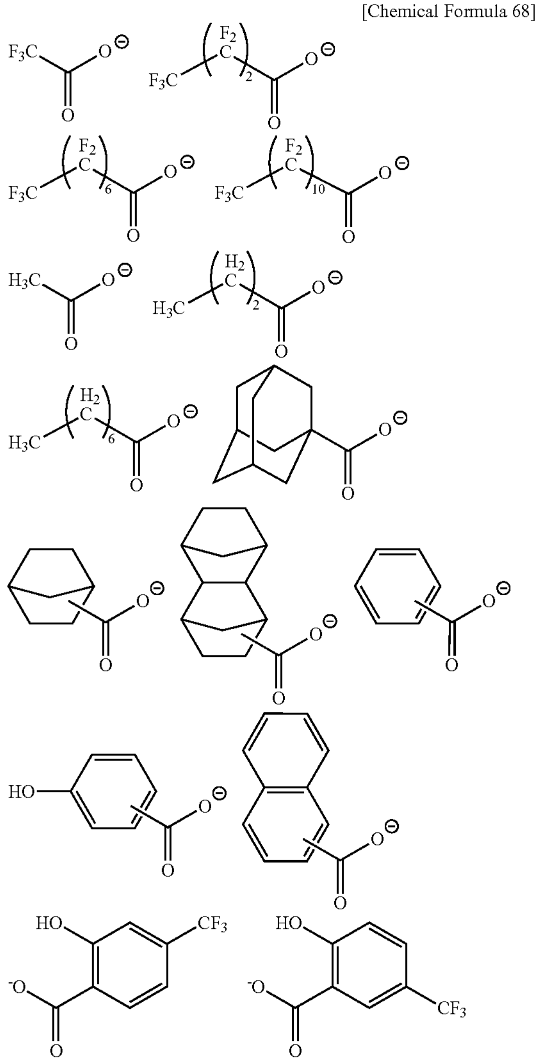

Cation Moiety

In formula (d1-1), $M^+$ represents an organic cation.

The organic cation for $M^+$ is not particularly limited, and examples thereof include the same cation moieties as those described above in the aforementioned formula (b-1) or (b-2).

As the component (d1-1), one type of compound may be used, or two or more types of compounds may be used in combination.

[Component (d1-2)]

Anion Moiety

In formula (d1-2), $Z^{2c}$ represents a hydrocarbon group of 1 to 30 carbon atoms which may have a substituent.

The hydrocarbon group for $Z^{2c}$ which may have a substituent may be either an aliphatic hydrocarbon group or an aromatic hydrocarbon group, and the same aliphatic hydrocarbon groups and aromatic hydrocarbon groups as those described above for the aforementioned $X^{01}$ in the component (B) can be used.

Among these, as the hydrocarbon group for $Z^{2c}$ which may have a substituent, an aliphatic cyclic group which may have a substituent is preferable, and a group in which one or more hydrogen atoms have been removed from adamantane, norbornane, isobornane, tricyclodecane, tetracyclododecane or camphor (which may have a substituent) is more preferable.

The hydrocarbon group for $Z^{2c}$ may have a substituent, and the same substituents as those described above for $X^{01}$ in the aforementioned component (B) can be used. However, in $Z^{2c}$, the carbon adjacent to the S atom within $SO_3^-$ has no fluorine atom as a substituent. By virtue of $SO_3^-$ having no fluorine atom adjacent thereto, the anion of the component (d1-2) becomes an appropriately weak acid anion, thereby improving the quenching ability of the component (D).

Specific examples of preferable anion moieties for the component (d1-2) are shown below.

[Chemical Formula 69]

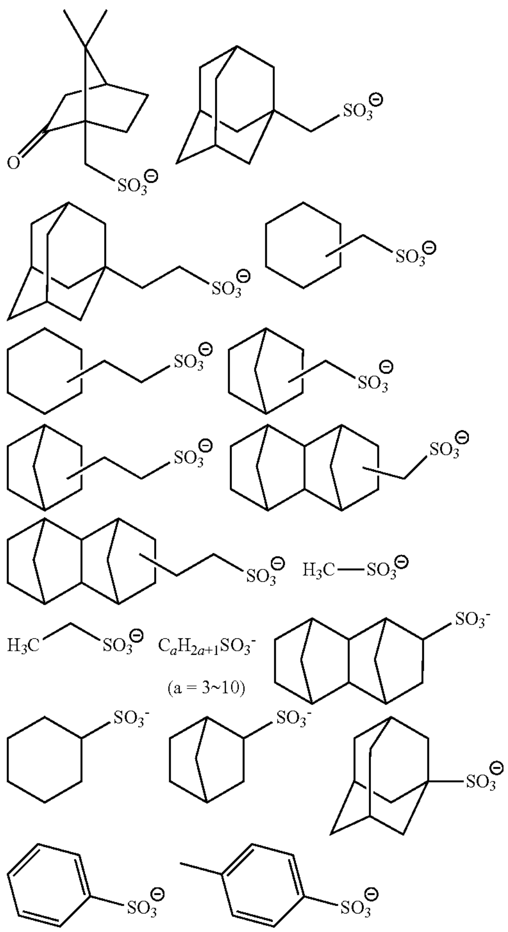

Cation Moiety

In formula (d1-2), $M^+$ is the same as defined for $M^+$ in the aforementioned formula (d1-1).

As the component (d1-2), one type of compound may be used, or two or more types of compounds may be used in combination.

[Component (d1-3)]

Anion Moiety

In formula (d1-3), $R^{52}$ represents an organic group. The organic group for $R^{52}$ is not particularly limited, and examples thereof include an alkyl group, an alkoxy group, $—O—C(=O)—C(R^{C2})=CH_2$ ($R^{C2}$ represents a hydrogen atom, an alkyl group of 1 to 5 carbon atoms or a halogenated alkyl group of 1 to 5 carbon atoms) and $—O—C(=O)—R^{C3}$ ($R^{C3}$ represents a hydrocarbon group).

The alkyl group for $R^{52}$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $R^{52}$ may be substituted with a hydroxy group, a cyano group or the like.

The alkoxy group for $R^{52}$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are particularly desirable.

When $R^{52}$ is —O—C(=O)—C($R^{C2}$)=$CH_2$, $R^{C2}$ represents a hydrogen atom, an alkyl group of 1 to 5 carbon atoms or a halogenated alkyl group of 1 to 5 carbon atoms.

The alkyl group of 1 to 5 carbon atoms for $R^{C2}$ is preferably a linear or branched alkyl group of 1 to 5 carbon atoms, and specific examples thereof include a methyl group, an ethyl group, a propyl group, an isopropyl group, an n-butyl group, an isobutyl group, a tert-butyl group, a pentyl group, an isopentyl group and a neopentyl group.

The halogenated alkyl group for $R^{C2}$ is a group in which part or all of the hydrogen atoms of the aforementioned alkyl group of 1 to 5 carbon atoms has been substituted with halogen atoms. Examples of the halogen atom include a fluorine atom, a chlorine atom, a bromine atom and an iodine atom, and a fluorine atom is particularly desirable.

As $R^{C2}$, a hydrogen atom, an alkyl group of 1 to 3 carbon atoms or a fluorinated alkyl group of 1 to 3 carbon atoms is preferable, and a hydrogen atom or a methyl group is particularly desirable in terms of industrial availability.

When $R^{52}$ is —O—C(=O)—$R^{c3}$, $R^{C3}$ represents a hydrocarbon group.

The hydrocarbon group for $R^{C3}$ may be either an aromatic hydrocarbon group or an aliphatic hydrocarbon group. Specific examples of the hydrocarbon group for $R^{c3}$ include the same hydrocarbon groups as those described for $X^{01}$ in the component (B).

Among these, as the hydrocarbon group for $R^{C3}$, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $R^{C3}$ is an alicyclic group, the resist composition can be satisfactorily dissolved in an organic solvent, thereby improving the lithography properties. Alternatively, when $R^{C3}$ is an aromatic group, the resist composition exhibits an excellent photoabsorption efficiency in a lithography process using EUV or the like as the exposure source, thereby resulting in the improvement of the sensitivity and the lithography properties.

Among these, as $R^{52}$, —O—C(=O)—C($R^{c2'}$)=$CH^2$ ($R^{C2'}$ represents a hydrogen atom or a methyl group) or —O—C(=O)—$R^{c3'}$ ($R^{C3'}$ represents an aliphatic cyclic group) is preferable.

In formula (d1-3), $Y^3$ represents a linear, branched or cyclic alkylene group or an arylene group.

Examples of the linear, branched or cyclic alkylene group or the arylene group for $Y^3$ include the "linear or branched aliphatic hydrocarbon group", "cyclic aliphatic hydrocarbon group" and "aromatic hydrocarbon group" described above as the divalent linking group for $Y^{22}$ in the aforementioned formula (a1-0-2).

Among these, as $Y^3$, an alkylene group is preferable, a linear or branched alkylene group is more preferable, and a methylene group or an ethylene group is still more preferable.

In formula (d1-3), Rf represents a hydrocarbon group containing a fluorine atom.

The hydrocarbon group containing a fluorine atom for Rf is preferably a fluorinated alkyl group, and more preferably the same fluorinated alkyl groups as those described above for $R^{51}$.

Specific examples of preferable anion moieties for the component (d1-3) are shown below.

[Chemical Formula 70]

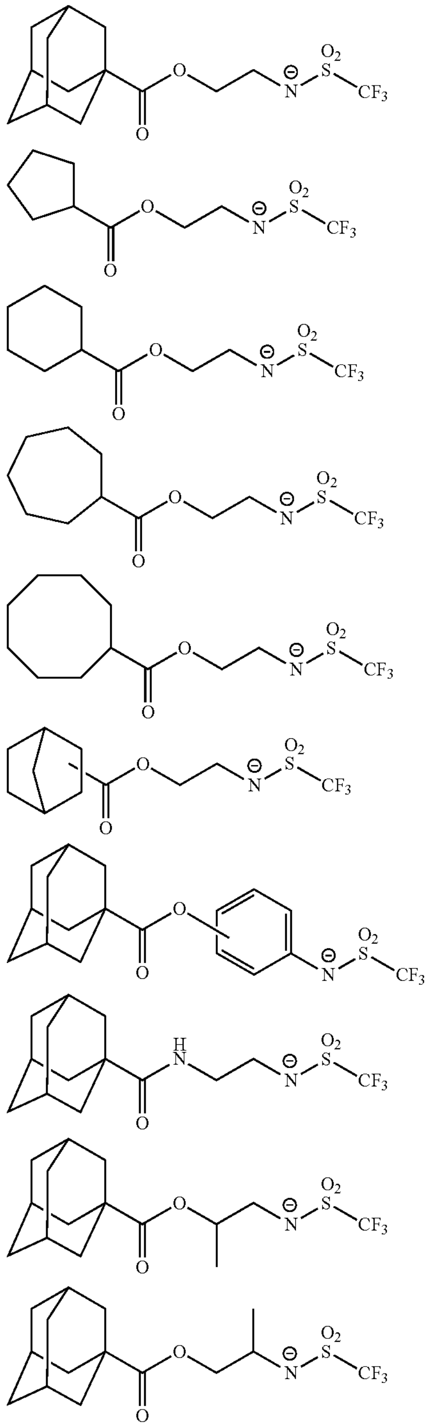

-continued

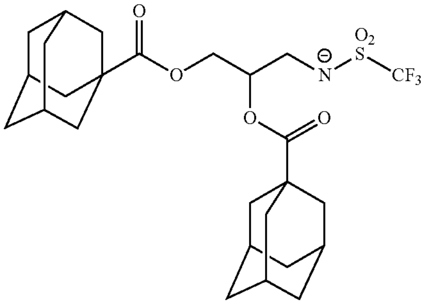

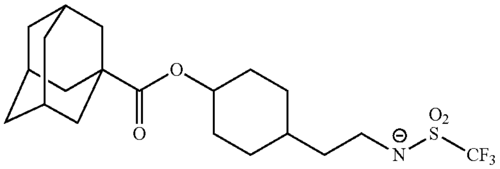

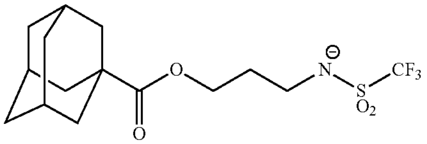

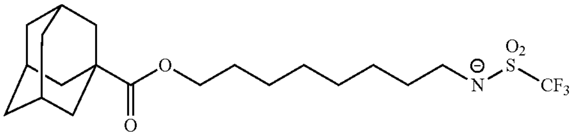

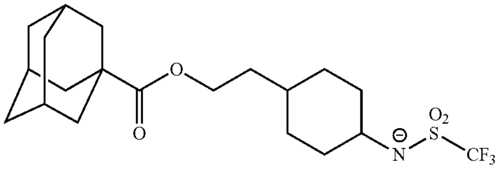

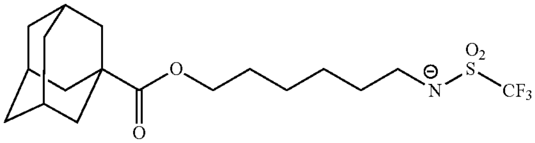

[Chemical Formula 71]

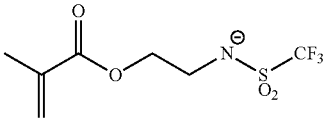

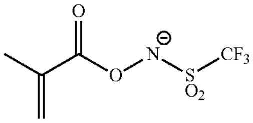

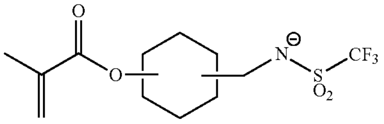

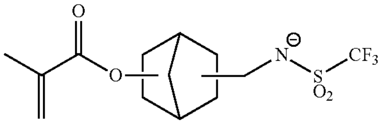

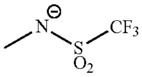
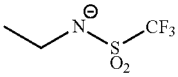

-continued

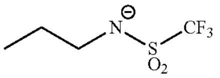
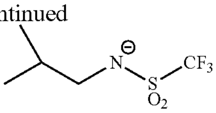

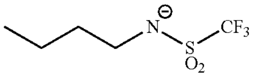

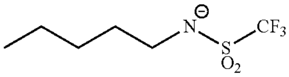

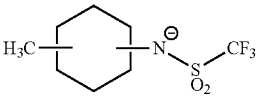

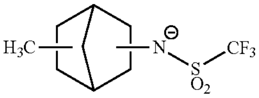

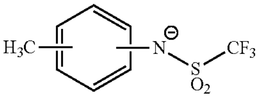

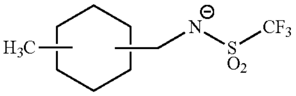

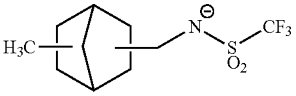

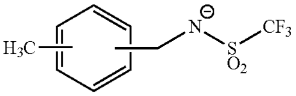

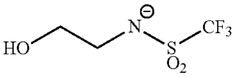

Cation Moiety

In formula (d1-3), $M^+$ is the same as defined for $M^+$ in the aforementioned formula (d1-1).

As the component (d1-3), one type of compound may be used, or two or more types of compounds may be used in combination.

The component (D1) may contain one of the aforementioned components (d1-1) to (d1-3), or at least two of the aforementioned components (d1-1) to (d1-3).

The total amount of the components (d1-1) to (d1-3) relative to 100 parts by weight of the component (A) is preferably within a range from 0.5 to 10.0 parts by weight, more preferably from 0.5 to 8.0 parts by weight, and still more preferably from 1.0 to 5.0 parts by weight. When the amount is at least as large as the lower limit of the above-mentioned range, a resist pattern having excellent lithography properties and pattern shape can be formed. On the other hand, when the amount of the component (C1) is no more than the upper limit of the above-mentioned range, sensitivity can be maintained at a satisfactory level, and throughput becomes excellent.

(Production Method of Component (D1))

In the present invention, the production methods of the components (d1-1) and (d1-2) are not particularly limited, and the components (d1-1) and (d1-2) can be produced by conventional methods.

The production method of the compound (d1-3) of the present invention is not particularly limited. For example, in the case where $R^{52}$ in formula (d1-3) is a group having an oxygen atom on the terminal thereof which is bonded to $Y^3$, the compound (d1-3) represented by general formula (d1-3)

can be produced by reacting a compound (i-1) represented by general formula (i-1) shown below with a compound (i-2) represented by general formula (i-2) shown below to obtain a compound (i-3) represented by general formula (i-3), and reacting the compound (i-3) with a compound $Z^-M^+$ (i-4) having the desired cation $M^+$, thereby obtaining the compound (d1-3) represented by general formula (d1-3).

[Chemical Formula 72]

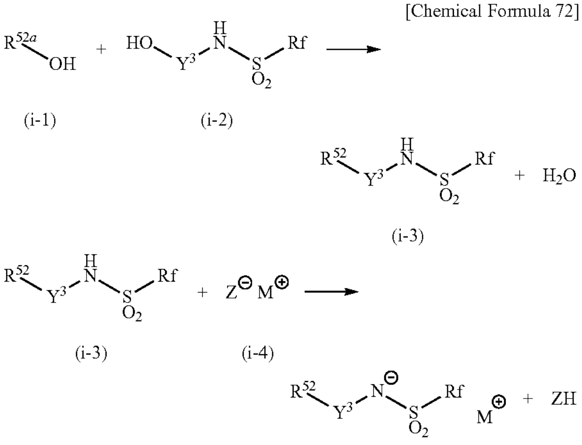

(i-1) (i-2) (i-3) (i-3) (i-4) (d1-3)

In the formulas, $R^{52}$, $Y^3$, Rf and $M^+$ are respectively the same as defined for $R^{52}$, $Y^3$, Rf and $M^+$ in the aforementioned general formula (d1-3); $R^{52a}$ represents a group in which the terminal oxygen atom has been removed from $R^{52}$; and $Z^-$ represents a counteranion.

Firstly, the compound (i-1) is reacted with the compound (i-2), to thereby obtain the compound (i-3).

In formula (i-1), $R^{52}$ is the same as defined above, and $R^{52a}$ represents a group in which the terminal oxygen atom has been removed from $R^{52}$. In formula (i-2), $Y^3$ and Rf are the same as defined above.

As the compound (i-1) and the compound (i-2), commercially available compounds may be used, or the compounds may be synthesized.

The method for reacting the compound (i-1) with the compound (i-2) to obtain the compound (i-3) is not particularly limited, but can be performed, for example, by reacting the compound (i-1) with the compound (i-2) in an organic solvent in the presence of an appropriate acidic catalyst, followed by washing and recovering the reaction mixture.

The acidic catalyst used in the above reaction is not particularly limited, and examples thereof include toluenesulfonic acid and the like. The amount of the acidic catalyst is preferably 0.05 to 5 moles, per 1 mole of the compound (i-2).

As the organic solvent used in the above reaction, any organic solvent which is capable of dissolving the raw materials, i.e., the compound (i-1) and the compound (i-2) can be used, and specific examples thereof include toluene and the like. The amount of the organic solvent is preferably 0.5 to 100 parts by weight, more preferably 0.5 to 20 parts by weight, relative to the amount of the compound (i-1). As the solvent, one type may be used alone, or two or more types may be used in combination. In general, the amount of the compound (i-2) used in the above reaction is preferably 0.5 to 5 moles per 1 mole of the compound (i-1), and more preferably 0.8 to 4 moles per 1 mole of the compound (i-1).

The reaction time depends on the reactivity of the compounds (i-1) and (i-2), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

Next, the obtained compound (i-3) is reacted with the compound (i-4), thereby obtaining the compound (d1-3).

In formula (i-4), $M^+$ is the same as defined above, and Z represents a counteranion.

The method for reacting the compound (i-3) with the compound (i-4) to obtain the compound (d1-3) is not particularly limited, but can be performed, for example, by dissolving the compound (i-3) in an organic solvent and water in the presence of an appropriate alkali metal hydroxide, followed by addition of the compound (i-4) and stirring.

The alkali metal hydroxide used in the above reaction is not particularly limited, and examples thereof include sodium hydroxide, potassium hydroxide and the like. The amount of the alkali metal hydroxide is preferably 0.3 to 3 moles, per 1 mole of the compound (i-3).

Examples of the organic solvent used in the above reaction include dichloromethane, chloroform, ethyl acetate and the like. The amount of the organic solvent is preferably 0.5 to 100 parts by weight, and more preferably 0.5 to 20 parts by weight, relative to the weight of the compound (i-3). As the solvent, one type may be used alone, or two or more types may be used in combination.

In general, the amount of the compound (i-4) used in the above reaction is preferably 0.5 to 5 moles per 1 mole of the compound (1-3), and more preferably 0.8 to 4 moles per 1 mole of the compound (i-1).

The reaction time depends on the reactivity of the compounds (i-3) and (i-4), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

After the reaction, the compound (d1-3) within the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

The structure of the compound (d1-3) obtained in the above-described manner can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

[Component (D2)]

The component (D2) is not particularly limited, as long as it is a compound which is basic relative to the component (B), so as to functions as an acid diffusion inhibitor, and does not fall under the definition of the component (D1). As the component (D2), any of the conventionally known compounds may be selected for use. Among these, an aliphatic amine, particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris {2-(2-methoxyethoxy)ethyl}amine, tris {2-(2-methoxyethoxymethoxy)ethyl}amine, tris {2-(1-methoxyethoxy)ethyl}amine, tris {2-(1-ethoxyethoxy)ethyl}amine, tris {2-(1-ethoxypropoxy)ethyl}amine, tris [2-{2-(2-hydroxyethoxy)ethoxy}ethyl]amine and triethanolamine triacetate, and triethanolamine triacetate is preferable.

Further, as the component (D2), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonylpyrrolidine.

As the component (D2), one type of compound may be used alone, or two or more types may be used in combination.

The component (D2) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

As the component (D), one type of resin may be used, or two or more types of resins may be used in combination.

When the resist composition of the present invention contains the component (D), the amount of the component (D) relative to 100 parts by weight of the component (A) is preferably within a range from 0.1 to 15 parts by weight, more preferably from 0.3 to 12 parts by weight, and still more preferably from 0.5 to 10 parts by weight. When the amount of the component (D) is at least as large as the lower limit of the above-mentioned range, various lithography properties (such as roughness) of the positive resist composition are improved. Further, a resist pattern having an excellent shape can be obtained. On the other hand, when the amount of the component (D) is no more than the upper limit of the above-mentioned range, sensitivity can be maintained at a satisfactory level, and throughput becomes excellent.

<Optional Component—Component (E)>

Furthermore, in the resist composition, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added as an optional component.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenyl phosphonate, diphenyl phosphonate and dibenzyl phosphonate.

Examples of phosphinic acid derivatives include phosphinic acid esters and phenylphosphinic acid.

As the component (E), one type may be used alone, or two or more types may be used in combination.

As the component (E), an organic carboxylic acid is preferred, and salicylic acid is particularly desirable.

The component (E) is typically used in an amount within a range from 0.01 to 5.0 parts by weight, relative to 100 parts by weight of the component (A).

<Component (S)>

The resist composition can be produced by dissolving the materials for the resist composition in an organic solvent (hereafter, referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples of the component (S) include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

The component (S) can be used individually, or in combination as a mixed solvent.

Among these, γ-butyrolactone, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3. Further, as the component (S), a mixed solvent of at least one of PGMEA and EL with γ-butyrolactone is also preferable. The mixing ratio (former:latter) of such a mixed solvent is preferably from 70:30 to 95:5.

Furthermore, as the component (S), a mixed solvent of PGMEA and cyclohexanone, or a mixed solvent of PGMEA, PGME and cyclohexanone is also preferable. The mixing ratio of the former mixed solvent is preferably PGMEA: cyclohexanone=95-5:10-90, and the mixing ratio of the latter mixed solvent is preferably PGMEA:PGME:cyclohexanone=35-55:25-45:10-30.

The component (B1) used in the resist composition of the present invention described above is a novel component essentially unknown in the art.

In the resist composition according to the present invention, by using a component (B1) as a component (B), various lithography properties such as LWR, EL margin, and MEF and resist pattern shape are improved.

In the present invention, the reasons why the above-mentioned effects can be achieved have not been elucidated yet. However, one of the reasons is presumed that by virtue of the component (B1) having a cyclic group containing $—SO_2—$ bond or $—O—SO_2$-bond, polarity of the component (B1) becomes high, thereby the component (B1) can be uniformly distributed in the resist composition. In addition, because the cyclic group has a bulky structure, diffusion of acid generated from the component (B1) which is uniformly distributed in the film can be suppressed, thereby improving the lithography properties and the pattern shape of the formed resist pattern.

In addition, by virtue of the group represented by formula (b1-1) of the present invention having a carbon atom which is not adjacent to the $—SO_2—$ bond or the $—O—SO_2$-bond and has an oxygen atom as a substituent, polarity becomes high compared to the group in which a carbon atom that is not adjacent to the $—SO_2—$ bond or the $—O—SO_2—$ bond does not have an oxygen atom as a substituent. Therefore, it is presumed that the aforementioned effects are increased.

<<Method of Forming a Resist Pattern>>

Using the resist composition as described above, for example, a resist pattern can be formed by a method as described below.

Firstly, a resist composition of the present invention is applied to a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an ArF exposure apparatus, an electron lithography system or the like, the resist film is selectively exposed to an ArF excimer laser beam or an electron beam (EB) through a desired mask pattern, followed by post exposure bake (PEB) under temperature conditions of 80 to 150° C. for 40 to 120 seconds, preferably 60 to 90 seconds. Subsequently, the resist film is subjected to a developing process.

In the case of an alkali developing process, an alkali developing solution such as a 0.1 to 10% by weight aqueous solution of tetramethylammonium hydroxide (TMAH) is used to perform an alkali developing treatment.

Alternatively, in the case of a solvent developing process, an organic solvent is used to perform a developing treatment. As the organic solvent, any of the conventional organic solvents can be used which are capable of dissolving the component (A) (prior to exposure). Specific examples of the organic solvent include polar solvents such as ketone solvents, ester solvents, alcohol solvents, amide solvents and ether solvents, and hydrocarbon solvents. Among these, ester solvents are preferable. As an ester solvent, butyl acetate is preferable.

As described above, when the resist composition of the present invention is used as a negative resist composition in a solvent developing process which is particularly desirable in the formation of a contact hole pattern, the shape of the contact hole pattern can be effectively prevented from becoming reverse-tapered. Therefore, the resist composition of the present invention is preferably used in a solvent developing process.

After the developing treatment, it is preferable to conduct a rinse treatment. In the case of an alkali developing process, it is preferable to conduct a water rinse using pure water. In the case of after an alkali developing process, it is preferable to perform a rinse treatment using a rinse liquid containing an organic solvent.

Thereafter, drying is conducted. If desired, bake treatment (post bake) can be conducted following the developing. In this manner, a resist pattern that is faithful to the mask pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) can be used.

The wavelength to be used for exposure is not particularly limited and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays.

The resist composition of the present invention is effective to KrF excimer laser, ArF excimer laser, EB and EUV, and particularly effective to ArF excimer laser.

The exposure of the resist film can be either a general exposure (dry exposure) conducted in air or an inert gas such as nitrogen, or immersion exposure (immersion lithography).

In immersion lithography, exposure (immersion exposure) is conducted in a state where the region between the lens and the resist layer formed on a wafer (which was conventionally filled with air or an inert gas such as nitrogen) is filled with a solvent (a immersion medium) that has a larger refractive index than the refractive index of air.

More specifically, in immersion lithography, the region between the resist film formed in the above-described manner and lens at the lowermost portion of the exposure apparatus is filled with a solvent (a immersion medium) that has a larger refractive index than the refractive index of air, and in this state, the resist film is subjected to exposure (immersion exposure) through a desired mask pattern.

The immersion medium preferably exhibits a refractive index larger than the refractive index of air but smaller than the refractive index of the resist film to be subjected to immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds. Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

<<Compound>>

The compound according to a third aspect of the present invention is a compound represented by general formula (b1-1) shown below. The compound represented by following formula (b1-1) is the same as the component (B1) included in the component (B) of the resist composition according to the first aspect of the present invention.

[Chemical Formula 73]

$$X\text{-}Q^1\text{-}Y^1\text{—}SO_3^{\ominus}A^{\oplus} \quad (b1\text{-}1)$$

wherein, X represents a cyclic group of 3 to 30 carbon atoms which may have a substituent, provided that a ring skelton of the cyclic group contains an —$SO_2$— bond or an —O—$SO_2$— bond, and at least one carbon atom which is not adjacent to the —$SO_2$— bond or the —O—$SO_2$— bond has an oxygen atom as a substituent; $Q^1$ represents a divalent linking group or a single bond; $Y^1$ represents an alkylene group which may have a substituent or a fluorinated alkylene group which may have a substituent; and $A^+$ represents an organic cation.

(Production Method of Compound)

The production method of the compound (b1-1) of the present invention is not particularly limited. For example, in the case where $Q^1$ is a divalent linking group having an oxygen atom on the terminal thereof which is bonded to X, the compound (b1-1) represented by general formula (b1-1) can be produced by reacting a compound (i-1) represented by general formula (i-1) shown below with a compound (i-2) represented by general formula (i-2) shown below to obtain a compound (i-3) represented by general formula (i-3), then reacting the obtained compound (i-3) with a compound $A^+X^-$ (i-4) having the desired cation $A^+$.

[Chemical Formula 74]

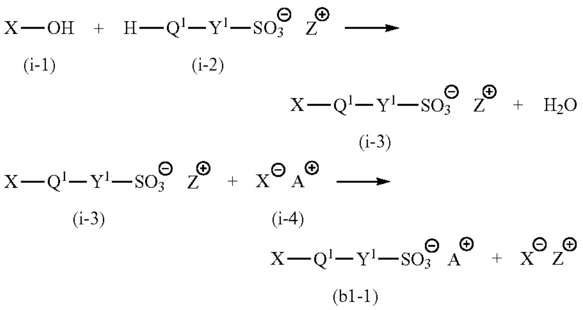

In formula, each of X, $Q^1$, $Y^1$, $A^+$ is the same as defined above. $Z^+$ represents an alkali metal ion, or an ammonium ion which may have a substituent; and $X^-$ represents an counteranion.

In formulas (i-1) and (i-2), X, $Q^1$, and $Y^1$ are the same as defined above, and $Z^+$ represents an alkali metal ion, an amine salt, or an ammonium salt.

Examples of alkali metal ions include a sodium ion, a lithium ion and a potassium ion, and a sodium ion or a lithium ion is preferable.

As an example of the ammonium ion which may have a substituent, a group represented by general formula (0-1) shown below can be given.

[Chemical Formula 75]

(0-1)

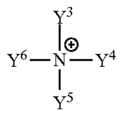

In the formula, each of $Y^3$ to $Y^6$ independently represents a hydrogen atom or a hydrocarbon group which may have a substituent, provided that at least one of $Y^3$ to $Y^6$ represents the hydrocarbon group; and at least two of $Y^3$ to $Y^6$ may be mutually bonded to form a ring.

In formula (0-1), each of $Y^3$ to $Y^6$ independently represents a hydrogen atom or a hydrocarbon group which may have a substituent, provided that at least one of $Y^3$ to $Y^6$ represents the hydrocarbon group.

As the hydrocarbon group for $Y^3$ to $Y^6$, the same groups as those described above for $X^0$ can be mentioned.

The hydrocarbon group may be either an aliphatic hydrocarbon group or an aromatic hydrocarbon group. When the hydrocarbon group is an aliphatic hydrocarbon group, it is particularly desirable that the hydrocarbon group is an alkyl group of 1 to 12 carbon atoms which may have a substituent.

At least one of $Y^3$ to $Y^6$ is a hydrocarbon group, and it is preferable that two or three groups are hydrocarbon groups.

At least two of $Y^3$ to $Y^6$ may be mutually bonded to form a ring. For example, two of $Y^3$ to $Y^6$ may be bonded to form a ring, three of $Y^3$ to $Y^6$ may be bonded to form a ring, or two of $Y^3$ to $Y^6$ may be bonded to form a ring, and the remaining two may be bonded to form another ring.

The ring which is formed by at least two of $Y^3$ to $Y^6$ bonded together with the nitrogen atom (i.e., the hetero ring containing nitrogen as a hetero atom) may be either an aliphatic hetero ring, or an aromatic hetero ring. Further, the hetero ring may be either a monocyclic group or a polycyclic group.

Specific examples of the ammonium ion represented by general formula (0-1) include ammonium ions derived from an amine.

Here, an "ammonium ion derived from an amine" refers to an amine having a hydrogen atom bonded to the nitrogen atom to become a cation, and a tertiary ammonium ion in which a substituent has been bonded to the nitrogen atom of an amine.

The amine from which the ammonium ion is derived may be either an aliphatic amine or an aromatic amine.

As the aliphatic amine, an amine in which at least one hydrogen atom of ammonia ($NH_3$) has been substituted with an alkyl group or hydroxyalkyl group of no more than 12 carbon atoms (i.e., alkylamines or alkylalcoholamines), or a cyclic amine is particularly desirable.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of aromatic amines include aniline, pyridine, 4-dimethylaminopyridine (DMAP), pyrrole, indole, pyrazole, and imidazole.

Examples of the tertiary ammonium ion include a tetramethylammonium ion, a tetraethylammonium ion and a tetrabutylammonium ion.

As the ammonium ion represented by general formula (0-1), a group in which at least one of $Y^3$ to $Y^6$ is an alkyl group and at least one is a hydrogen atom is particularly desirable.

Especially, a group in which three of $Y^3$ to $Y^6$ are alkyl groups, and the remaining one is a hydrogen atom (i.e., a trialkylammonium ion), or a group in which two of $Y^3$ to $Y^6$ are alkyl groups, and the remaining two are hydrogen atoms (i.e., dialkylammonium ion) is preferable.

It is preferable that each of the alkyl groups within the trialkylammonium ion or the dialkylammonium ion independently has 1 to 10 carbon atoms, more preferably 1 to 8, and most preferably 1 to 5. Specific examples include a methyl group, an ethyl group, a propyl group, a butyl group, a pentyl group, a hexyl group, a heptyl group, an octyl group, a nonyl group and a decyl group. Among these, an ethyl group is particularly desirable.

As the compound (i-1) and the compound (i-2), commercially available compounds may be used, or the compounds may be synthesized.

The method for reacting the compound (i-1) with the compound (i-2) to obtain the compound (i-3) is not particularly limited, but can be performed, for example, by dissolving the compound (i-1) and the compound (i-2) in an organic solvent, followed by stirring in the presence of an appropriate acidic catalyst and performing a dehydration/condensation reaction of the compound (i-1) with the compound (i-2), and followed by washing and recovering the reaction mixture.

As the organic solvent, any organic solvent capable of dissolving the compounds (i-1) and (i-2) as raw materials can be used, and specific examples include aprotic organic solvents such as dichloroethane, benzene, toluene, ethylbenzene, chlorobenzene, acetonitrile, N,N-dimethylformamide. The amount of the organic solvent relative to the compound (i-1) is preferably within a range from 0.5 to 100 parts by weight, and more preferably from 0.5 to 20 parts by weight. As the solvent, one type may be used alone, or two or more types may be used in combination.

Examples of the acidic catalyst include an organic acid such as p-toluenesulfonic acid, and an organic acid such as sulfuric acid or hydrochloric acid.

These acidic catalysts may be used individually or in a combination of two or more.

The reaction time depends on the reactivity of the compounds (i-1) and (i-2), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

In general, the amount of the compound (i-2) used in the above reaction is preferably 0.5 to 5 moles per 1 mole of the compound (i-1), and more preferably 0.8 to 4 moles per 1 mole of the compound (i-1).

As the compound (i-4), commercially available compounds may be used, or the compounds may be synthesized. In the compound (i-4), $X^-$ is preferably a non-nucleophilic ion, and examples thereof include a halogen ion such as a bromine ion or a chlorine ion; an ion capable of forming an acid exhibiting a lower acidity than the compound (i-3); a p-toluenesulfonate acid ion, a methanesulfonate acid ion, benzenesulfonate acid ion, $BF_4^-$, $AsF_6^-$, $SbF_6^-$, $PF_6^-$ and $ClO_4^-$.

The method for reacting the compound (i-3) which can be obtained by aforementioned method with the compound (i-4) to obtain the compound (b0) is not particularly limited, but can be performed, for example, by adding the compound (i-3) and the compound (i-4) to an appropriate organic solvent and pure water, followed by stirring and reacting, then washing and recovering the reaction mixture.

Here, examples of organic solvents include dichloromethane, chloroform, and ethyl acetate. The amount of the organic solvent relative to the compound (i-3) is preferably within a range from 0.5 to 100 parts by weight, and more preferably from 0.5 to 20 parts by weight. As the solvent, one type may be used alone, or two or more types may be used in combination.

The reaction time depends on the reactivity of the compounds (i-3) and (i-4), the reaction temperature or the like. However, in general, the reaction time is preferably 0.5 to 50 hours, and more preferably 1 to 20 hours.

The reaction temperature in the above reaction is preferably 20 to 200° C., and more preferably 20 to 150° C.

In general, the amount of the compound (i-3) used in the above reaction is preferably 0.5 to 5 moles per 1 mole of the compound (i-4), and more preferably 0.8 to 4 moles per 1 mole of the compound (i-4).

After the reaction, the compound (b1-1) within the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

The structure of the compound obtained in the above-described manner can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

The compound of the present invention described above is a novel compound useful as an acid generator for a resist composition, and can be blended in a resist composition as an acid generator.

<<Acid Generator>>

The acid generator according to a fourth aspect of the present invention is an acid generator including the compound (b1-1).

The acid generator is useful for a chemically amplified resist composition, for example, the acid-generator component (B) of the resist composition according to the first aspect of the present invention.

EXAMPLES

As follows is a description of examples of the present invention, although the scope of the present invention is by no way limited by these examples.

In the NMR analysis of the present examples, the chemical shift standard for $^1$H-NMR was tetramethylsilane (TMS), and the chemical shift standard for $^{19}$F-NMR was trichlorofluoromethane (the peak of hexafluorobenzene was regarded as −162.2 ppm).

Synthesis Example 1

Production of Compound (3)

A mixture containing 5 g of a compound (1), 6.5 g of a compound (2), 0.05 g of p-toluenesulfonic acid monohydrate and 50 g of toluene was prepared, and reflux was conducted under normal pressure for 30 hours. The mixture was cooled to room temperature to obtain a slurry, and the slurry was filtered, followed by dispersing and washing with 50 g of t-butylmethylether 3 times, thereby obtaining 6.0 g of the compound (3).

The obtained compound (3) was analyzed by NMR, and the structure thereof was identified by the following results.

$^1$H-NMR (DMSO, 400 MHz): δ (ppm)=5.76 (d, 1H,CH), 4.87-5.05 (m, 3H, CH), 4.23 (m, 1H, CH), 2.28-2.40 (m, 2H, oxosultone).

$^{19}$F-NMR (DMSO, 376 MHz): δ (ppm)=−106.7.

From the results, it was confirmed that the compound (3) had a structure as shown below.

[Chemical Formula 76]

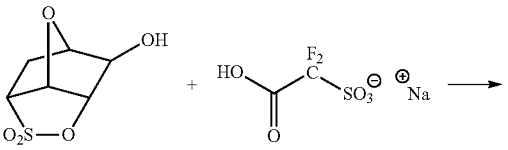

Compound (1) Compound (2)

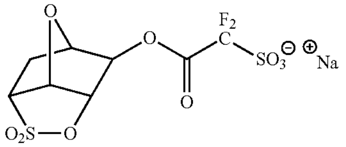

Compound (3)

Synthesis Example 2

Production of Compound (B)-1

A mixture containing 8.55 g of a compound (4), 9.63 g of a compound (3), 75 g of dichloromethane and 75 g of pure water was stirred for 1 hour. Then, the organic solvent phase was collected by liquid separation, followed by washing with 75 g of 1% by weight aqueous solution of hydrochloric acid, and washing with 75 g of pure water 4 times, then the organic solvent phase was concentrated and dried under reduced pressure.

The obtained compound (B)-1 was analyzed by NMR, and the structure thereof was identified by the following results.

$^1$H-NMR (DMSO, 400 MHz): δ (ppm)=7.53-7.95 (m, 14H, ArH), 5.76 (d, 1H, CH), 4.87-5.05 (m, 3H, CH), 4.23 (m, 1H, CH), 2.28-2.40 (m, 8H, $CH_3$+oxosultone)

$^{19}$F-NMR (DMSO, 376 MHz): δ (ppm)=−106.7.

From the results, it was confirmed that the compound (B)-1 had a structure as shown above.

[Chemical Formula 77]

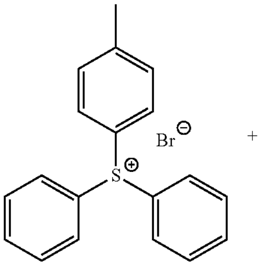

Compound (4)

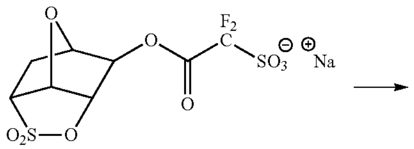

Compound (3)

-continued

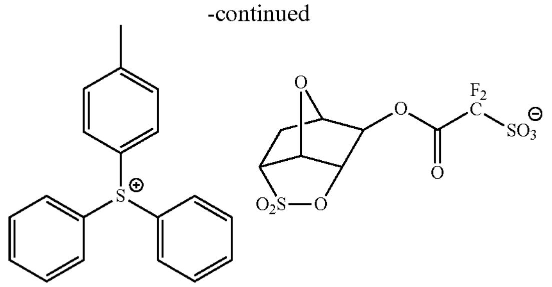

Compound (B)-1

Synthesis Examples 3 to 47

Synthesis of Compounds (B)-2 to (B)-46

The same procedure as in Synthesis Example 2 was performed, except that the compound (4) (cation) was replaced by each of cations shown in Tables 1 to 15 (equimolar amount). In this manner, compounds (B)-2 to (B)-46 shown in Tables 1 to 15 were obtained.

Each of the obtained compounds was analyzed by NMR. The results are shown in Tables 1 to 15.

TABLE 1

| Compound | NMR | Cation | Product |
|---|---|---|---|
| (B)-2 | 1H-NMR (DMSO, 400 MHz): δ (ppm) = 7.75-7.86 (m, 10H, ArH), 7.61 (s, 2H, ArH), 5.76 (d, 1H, CH), 4.87-5.05 (m, 3H, CH), 4.62 (s, 2H, CH2), 4.23 (m, 1H, CH), 2.28-2.40 (m, 8H, CH3 + oxosultone), 1.49-1.97 (m, 17H, Adamantane)<br>19F-NMR (DMSO, 376 MHz): δ (ppm) = −106.7 | 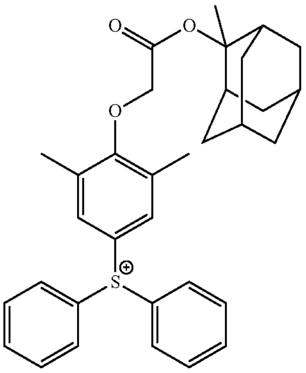 [SMILES: Cc1cc([S+](c2ccccc2)c2ccccc2)cc(C)c1OCC(=O)OC1(C)C2CC3CC(C2)CC1C3] | 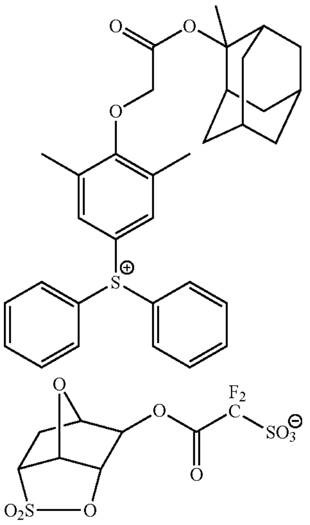 |
| (B)-3 | 1H-NMR (DMSO, 400 MHz): δ (ppm) = 7.76-7.82 (m, 10H, ArH), 7.59 (s, 2H, ArH), 5.76 (d, 1H, CH), 4.87-5.05 (m, 3H, CH), 4.55 (s, 2H, CH2), 4.23 (m, 1H, CH), 2.29-2.40 (m, 8H, CH3 + oxosultone), 1.90-1.93 (m, 4H, CH2, cyclopentyl), 1.48-1.75 (m, 6H, cyclopentyl), 0.77-0.81 (t, 3H, CH3)<br>1 9F-NMR (DMSO, 376 MHz): δ (ppm) = −106.7 | 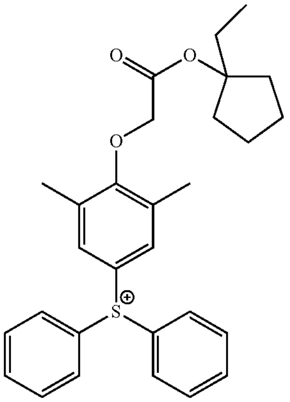 [SMILES: CCC1(OC(=O)COc2c(C)cc([S+](c3ccccc3)c3ccccc3)cc2C)CCCC1] | 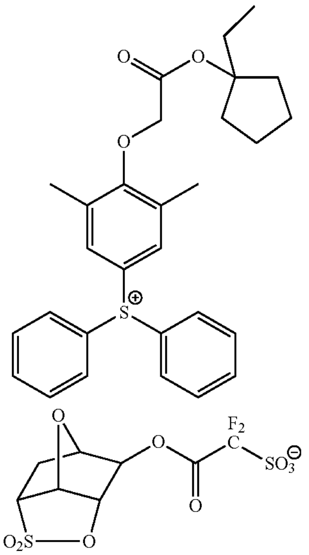 |

TABLE 1-continued
| Compound | NMR | Cation | Product |
|---|---|---|---|
| (B)-4 | 1H-NMR (DMSO, 400 MHz): δ (ppm) = 7.80-7.92 (m, 10H, ArH), 7.67 (s, 2H, ArH), 5.76 (d, 1H, CH), 4.87-5.05 (m, 3H, CH), 4.66 (s, 2H, CH2), 4.23 (m, 1H, CH), 2.28-2.40 (m, 8H, ArCH3 + oxosultone), 1.41-2.29 (m, 4H, Cyclohexyl + CH2), 1.14-1.57 (m, 8H, cyclohexyl), 0.84 (t, 3H, CH3)<br>19F-NMR (DMSO, 376 MHz): δ (ppm) = −106.7 | 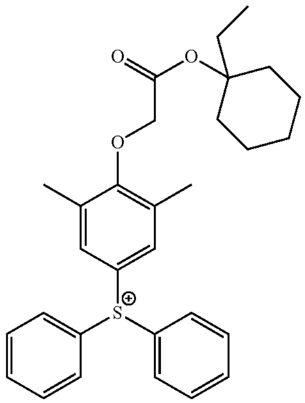 [SMILES: CCC1(OC(=O)COc2c(C)cc([S+](c3ccccc3)c3ccccc3)cc2C)CCCCC1] | 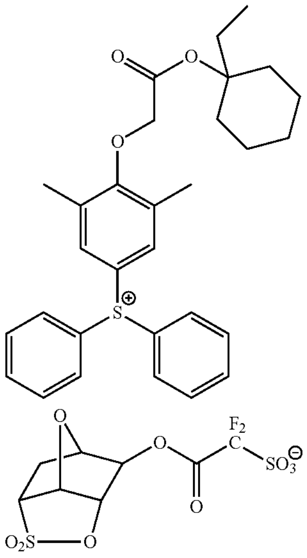 |
TABLE 2
| Compound | NMR | Cation | Product |
|---|---|---|---|
| (B)-5 | 1H-NMR (DMSO, 400 MHz): δ (ppm) = 7.76-7.82 (m, 10H, ArH), 7.59 (s, 2H, ArH), 5.76 (d, 1H, CH), 4.87-5.05 (m, 3H, CH), 4.55 (s, 2H, CH2), 4.23 (m, 1H, CH), 2.28-2.40 (m, 8H, CH3 + oxosultone), 1.90-2.08 (m, 2H, cyclopentyl), 1.48-1.75 (m, 9H, CH3, cyclopentyl)<br>19F-NMR (DMSO, 376 MHz): δ (ppm) = −106.7 | 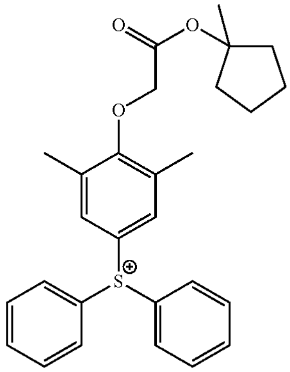 [SMILES: Cc1cc([S+](c2ccccc2)c2ccccc2)cc(C)c1OCC(=O)OC1(C)CCCC1] | 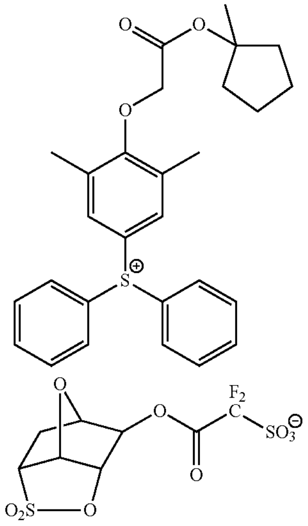 |

TABLE 2-continued
| Compound | NMR | Cation | Product |
|---|---|---|---|
| (B)-6 | 1H-NMR (DMSO, 400 MHz): δ (ppm) = 7.75-7.86 (m, 10H, ArH), 7.63 (s, 2H, ArH), 5.76 (d, 1H, CH), 4.87-5.05 (m, 3H, CH), 4.55 (s, 2H, CH2), 4.23 (m, 1H, CH), 2.28-2.40 (m, 8H, CH3 + oxosultone), 1.43 (s, 9H, t-Butyl) 19F- NMR (DMSO, 376 MHz): δ (ppm) = −106.7 | 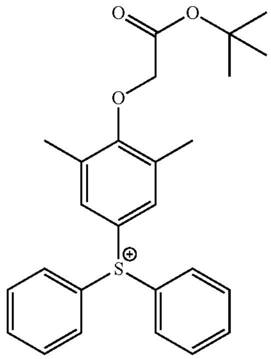 [SMILES: Cc1cc([S+](c2ccccc2)c2ccccc2)cc(C)c1OCC(=O)OC(C)(C)C] | 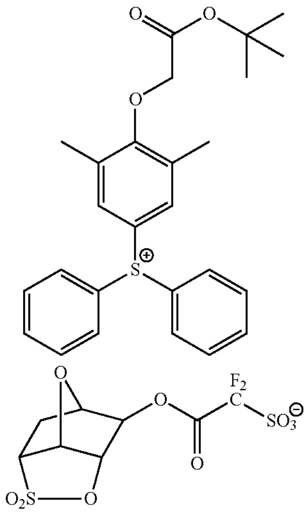 |
| (B)-7 | 1H-NMR (DMSO, 400 MHz): δ (ppm) = 7.72-7.84 (m, 10H, ArH), 7.59 (s, 2H, ArH), 5.76 (d, 1H, CH), 4.87-5.05 (m, 3H, CH), 4.64 (s, 2H, CH2), 4.23 (m, 1H, CH), 3.70 (s, 3H, OCH3), 2.28-2.40 (m, 8H, CH3 + oxosultone) 19F-NMR (DMSO, 376 MHz): δ (ppm) = −106.7 | 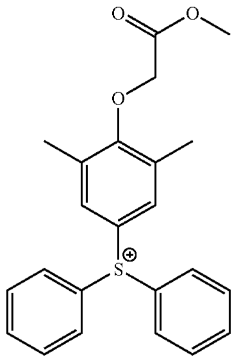 [SMILES: COC(=O)COc1c(C)cc([S+](c2ccccc2)c2ccccc2)cc1C] | 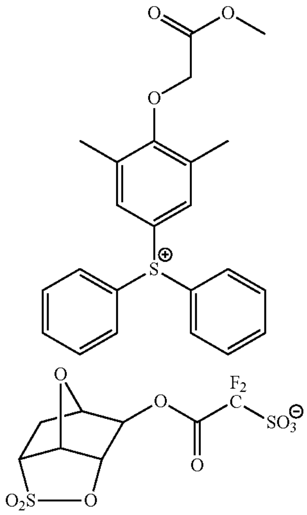 |

TABLE 3

| Compound | NMR | Cation | Product |
|---|---|---|---|
| (B)-8 | 1H-NMR (DMSO, 400 MHz): δ (ppm) = 8.49 (d, 2H, ArH), 8.30 (d, 2H, ArH), 7.93 (t, 2H, ArH), 7.73 (t, 2H, ArH), 7.30 (s, 2H, ArH), 5.76 (d, 1H, CH), 4.87-5.05 (m, 3H, CH), 4.52 (s, 2H, CH2), 4.23 (m, 1H, CH), 2.16-2.40 (m, 10H, CH3 + Adamantane + oxosultone), 1.44-1.92 (m, 15H, Adamantane + CH3)<br>19F-NMR (DMSO, 376 MHz): δ (ppm) = −106.7 | 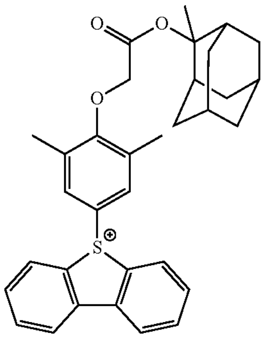 [SMILES: Cc1cc(-[s+]2c3ccccc3c3ccccc32)cc(C)c1OCC(=O)OC1(C)C2CC3CC(C2)CC1C3] | 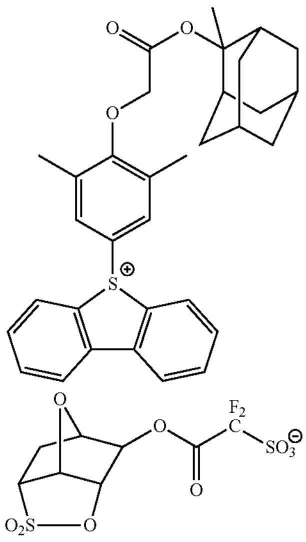 |
| (B)-9 | 1H-NMR (DMSO, 400 MHz): δ (ppm) = 10.05 (s, 1H, OH), 7.64-7.87 (m, 10H, ArH), 7.56 (s, 2H, ArH), 5.76 (d, 1H, CH), 4.87-5.05 (m, 3H, CH), 4.23 (m, 1H, CH), 2.22-2.40 (m, 8H, CH3 + oxosultone)<br>19F-NMR (DMSO, 376 MHz): δ (ppm) = −106.7 | 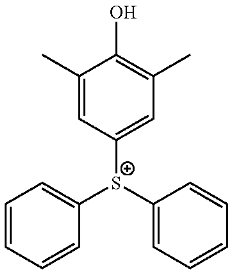 [SMILES: Cc1cc([S+](c2ccccc2)c2ccccc2)cc(C)c1O] | 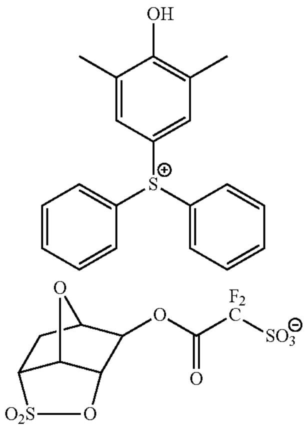 |
| (B)-10 | 1H-NMR (DMSO, 400 MHz): δ (ppm) = 7.71-7.89 (m, 10H, ArH), 7.59 (s, 2H, ArH), 5.76 (d, 1H, CH), 4.87-5.05 (m, 3H, CH), 4.53 (s, 2H, CH2), 4.23 (m, 1H, CH), 2.28-2.40 (m, 8H, CH3 + oxosultone)<br>1 9F-NMR (DMSO, 376 MHz): δ (ppm) = −106.7 | 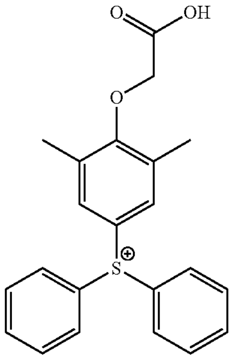 [SMILES: Cc1cc([S+](c2ccccc2)c2ccccc2)cc(C)c1OCC(=O)O] | 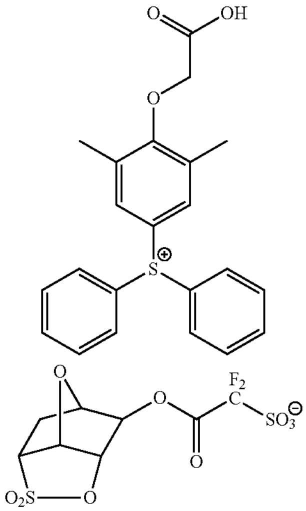 |

TABLE 4

| Compound | NMR | Cation | Product |
|---|---|---|---|
| (B)-11 | 1H-NMR (DMSO, 400 MHz); δ (ppm) = 9.73 (s, 1H, OH), 8.47 (d, 2H, ArH), 8.24 (d, 2H, ArH), 7.91 (t, 2H, ArH), 7.71 (t, 2H, ArH), 7.18 (s, 2H, ArH), 5.76 (d, 1H, CH), 4.87-5.05 (m, 3H, CH), 4.23 (m, 1H, CH), 2.10-2.40 (m, 8H, CH3 + oxosultone)<br>19F-NMR (DMSO, 376 MHz): δ (ppm) = −106.7 | 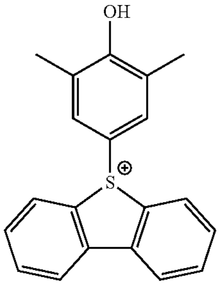 [SMILES: Cc1cc(-[s+]2c3ccccc3c3ccccc32)cc(C)c1O] | 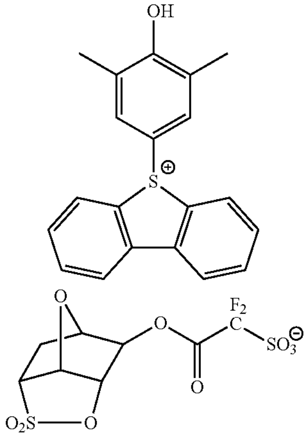 |
| (B)-12 | 1H NMR (DMSO, 400 MHz): δ (ppm) = 7.75-7.87 (m, 10H, ArH), 7.63 (s, 2H, ArH), 5.76 (d, 1H, CH), 4.84-5.05 (m, 7H, OCH2CF2 + CH2 + CH), 2.28-2.40 (m, 8H, CH3 + oxosultone)<br>19F-NMR (DMSO, 376 MHz) : δ (ppm) = −80.4, −106.7, −119.7 | 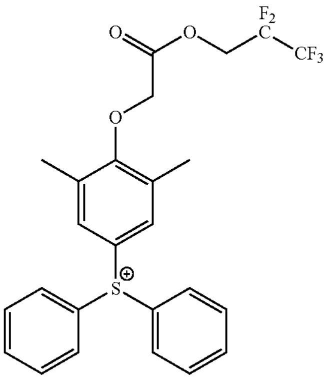 [SMILES: Cc1cc([S+](c2ccccc2)c2ccccc2)cc(C)c1OCC(=O)OCC(F)(F)C(F)(F)F] | 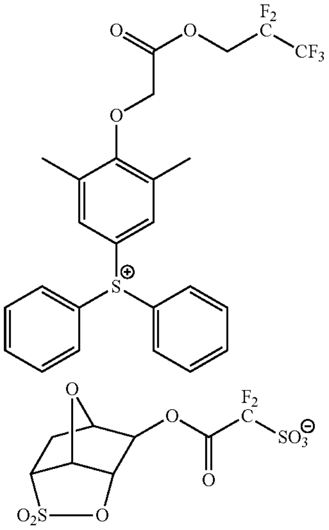 |
| (B)-13 | 1H-NMR (DMSO, 400 MHz): δ (ppm) = 7.72-7.83 (m, 10H, ArH), 7.59 (s, 2H, ArH), 5.76 (d, 1H, CH), 4.87-5.05 (m, 4H, sultone + CH), 4.62-4.68 (m, 3H, CH2 + suttone), 4.23 (m, 1H, CH), 3.83-3.89 (m, 1H, sultone), 3.43 (m, 1H, sultone), 1.75-2.49 (m, 13H, sultone + CH3 + oxosultone)<br>19F-NMR (DMSO, 376 MHz): δ (ppm) = −106.7 | 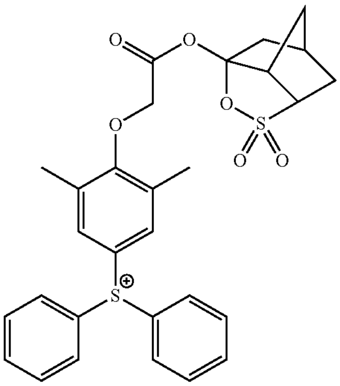 [SMILES: Cc1cc([S+](c2ccccc2)c2ccccc2)cc(C)c1OCC(=O)OC12CC3CC1C(C3)S(=O)(=O)O2] | 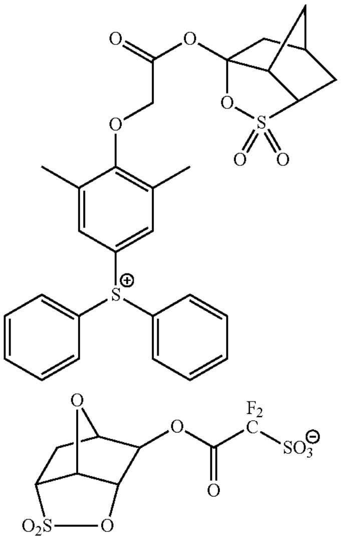 |

TABLE 5

| Compound | NMR | Cation | Product |
|---|---|---|---|
| (B)-14 | 1H-NMR (DMSO, 400 MHz): δ (ppm) = 7.74-7.84 (m, 10H, ArH), 7.61 (s, 2H, ArH), 5.76 (d, 1H, CH), 5.42 (t, 1H, oxo-norbornane), 4.87-5.05 (m, 4H, CH + oxo-norbornane), 4.67-4.71 (m, 4H, CH2 + oxo-norbornane), 4.23 (m, 1H, CH), 2.69-2.73 (m, 1H, oxo-norbornane), 2.28-2.40 (m, 8H, CH3 + oxosultone), 2.06-2.16 (m, 2H, oxo-norbornane)<br>19F-NMR (DMSO, 376 MHz): δ (ppm) = −106.7 | 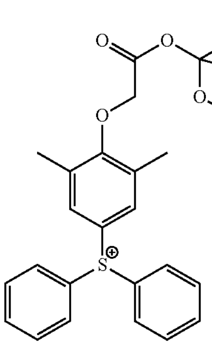 | 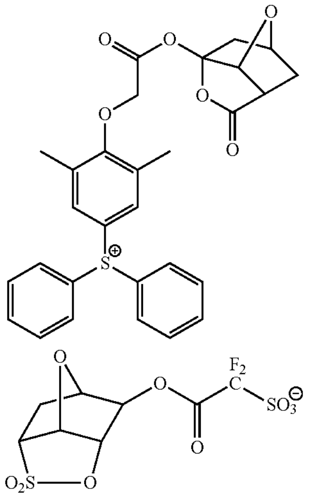 |
| (B)-15 | 1H-NMR (DMSO, 400 MHz): δ (ppm) = 7.74-7.84 (m, 10H, ArH), 7.61 (s, 1H, ArH), 5.76 (d, 1H, CH), 4.87-5.05 (m, 3H, CH), 4.49-4.66 (m, 4H, norbornane + OCH2), 4.23 (m, 1H, CH), 3.24 (m, 1H, norbornane), 2.28-2.54 (m, 10H, norbornane + CH3 + oxosultone), 1.91-2.06 (m, 2H, norbornane), 1.57-1.67 (m, 2H, norbornane)<br>19F-NMR (DMSO, 376 MHz): δ (ppm) = −106.7 | 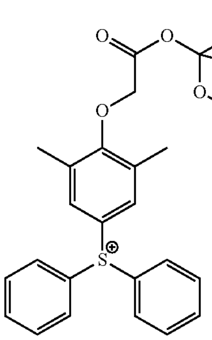 | 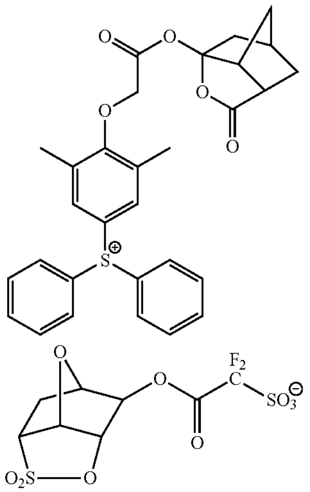 |
| (B)-16 | 1H-NMR (DMSO, 400 MHz): δ (ppm) = 7.77-7.89 (m, 10H, ArH), 7.64 (s, 2H, ArH), 5.70-5.76 (m, 2H, CH + OCHC═O), 4.87-5.05 (m, 5H, CH + CH2), 4.23-4.46 (m, 3H, CH2 + CH), 2.71-2.64 (m, 1H, OCH2CH2), 2.24-2.40 (m, 9H, CH3 + CH2 + oxosultone)<br>19F-NMR (DMSO, 376 MHz): δ (ppm) = −106.7 | 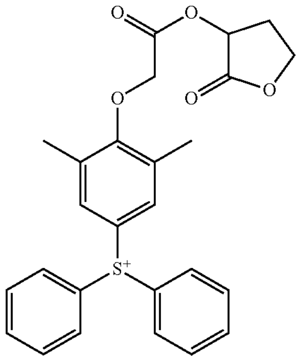 [SMILES: Cc1cc([S+](c2ccccc2)c2ccccc2)cc(C)c1OCC(=O)OC1CCOC1=O] | 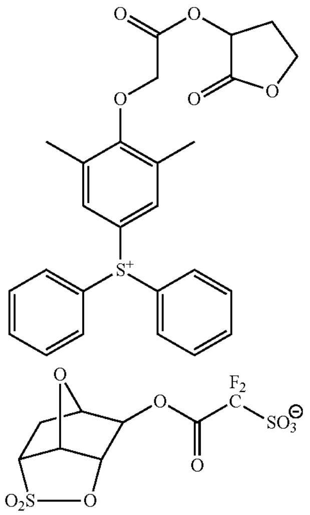 |

TABLE 6

| Compound | NMR | Cation | Product |
|---|---|---|---|
| (B)-17 | 1H-NMR (DMSO, 400 MHz): δ (ppm) = 7.76-7.90 (m, 12H, ArH), 5.76 (d, 1H, CH), 4.87-5.05 (m, 4H, Hyper-lactone + CH), 4.77 (s, 2H, Hyper-lactone), 4.27 (m, 2H, Hyper-lactone + CH), 2.94 (s, 1H, Hyper-lactone), 2.28-2.40 (m, 2H, oxosultone), 2.13 (d, 6H, CH3), 2.11-1.73 (m, 9H, Hyper-lactone), 1.53 (d, 1H, Hyper-lactone) 19F-NMR (DMSO, 376 MHz): δ (ppm) = −106.7 | 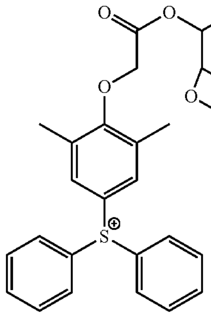 | 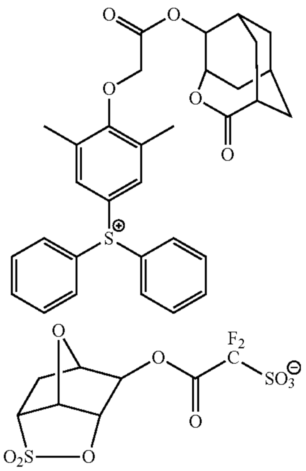 |
| (B)-18 | 1H-NMR (DMSO, 400 MHz): δ (ppm) = 7.72-7.83 (m, 10H, ArH), 7.59 (s, 2H, ArH), 5.90 (d, 1H, oxosultone), 5.76 (d, 1H, oxosultone), 4.87-5.05 (m, 6H, oxosultone), 4.62-4.68 (m, 2H, CH2), 4.23 (m, 2H, oxosultone), 1.75-2.48 (m, 10H, CH3 + oxosultone) 19F-NMR (DMSO, 376 MHz): δ (ppm) = −106.7 | 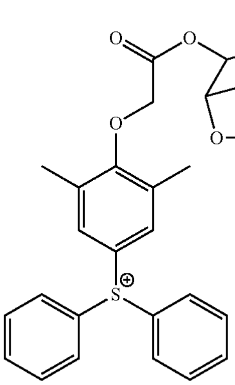 | 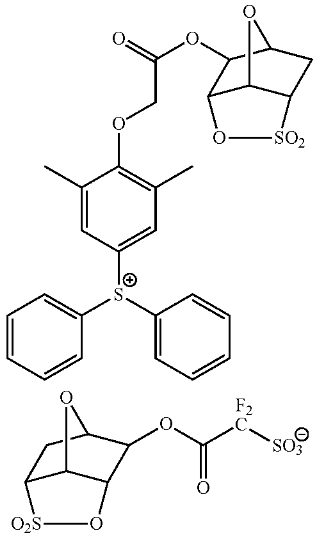 |
| (B)-19 | 1H-NMR (DMSO, 400 MHz): δ (ppm) = 7.73-7.85 (m, 10H, ArH), 7.59 (S, 2H, ArH), 5.76 (d, 1H, CH), 4.87-5.05 (m, 3H, CH), 4.23 (m, 1H, CH), 3.83 (t, 2H, OCH2), 2.28-2.40 (m, 8H, CH3 + oxosultone), 1.45 (m, 4H, CH2), 1.29 (m, 4H, CH2), 0.87 (t, 3H, CH3) 19F-NMR (DMSO, 376 MHz): δ (ppm) = −106.7 | 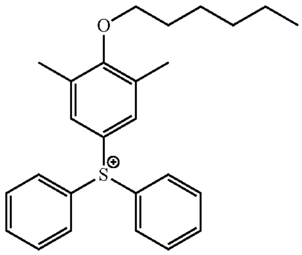 [SMILES: CCCCCCOc1c(C)cc([S+](c2ccccc2)c2ccccc2)cc1C] | 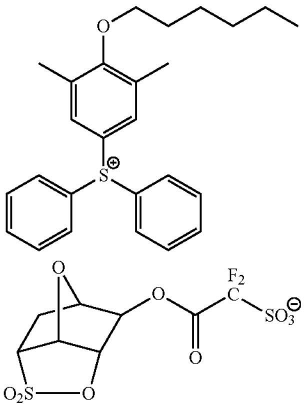 |

TABLE 7

| Compound | NMR | Cation | Product |
|---|---|---|---|
| (B)-20 | 1H-NMR (DMSO, 400 MHz): δ (ppm) = 7.84 (d, 6H, ArH), 7.78 (d, 6H, ArH), 5.76 (d, 1H, CH), 4.87-5.05 (m, 3H, CH), 4.23 (m, 1H, CH), 2.28-2.40 (m, 2H, oxosultone), 1.33 (s, 27H, tBu—CH3) 19F-NMR (DMSO, 376 MHz): δ (ppm) = −106.7 | 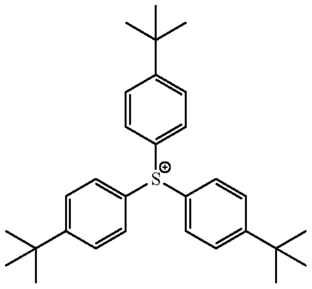 [SMILES: CC(C)(C)c1ccc([S+](c2ccc(C(C)(C)C)cc2)c2ccc(C(C)(C)C)cc2)cc1] | 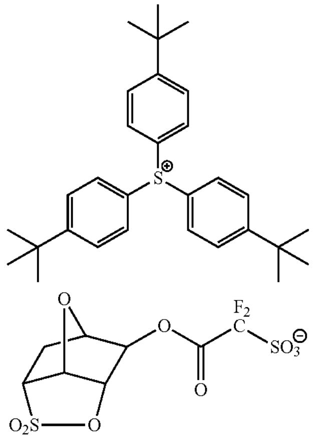 |
| (B)-21 | 1H-NMR (DMSO, 400 MHz): δ (ppm) = 8.05 (d, 2H, ArH), 7.74 (d, 2H, ArH), 5.76 (d, 1H, CH), 4.87-5.05 (m, 3H, CH), 4.23 (m, 1H, CH), 3.85 (s, 3H, S—CH3), 2.28-2.40 (m, 2H, oxosultone), 1.30 (s, 18H, t-Bu) 19F-NMR (DMSO, 376 MHz): δ (ppm) = −106.7 | 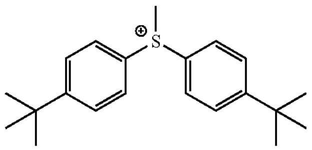 [SMILES: C[S+](c1ccc(C(C)(C)C)cc1)c1ccc(C(C)(C)C)cc1] | 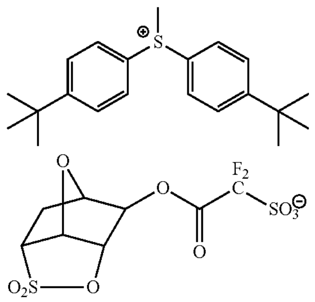 |
| (B)-22 | 1H-NMR (DMSO, 400 MHz): δ (ppm) = 8.53 (d, 2H, ArH), 8.27 (d, 2H, ArH), 7.95 (t, 2H, ArH), 7.74 (t, 2H, ArH), 7.20 (s, 1H, ArH), 6.38 (s, 1H, ArH), 5.76 (d, 1H, CH), 4.87-5.05 (m, 3H, CH), 4.23 (m, 1H, CH), 4.05 (t, 2H, CH2), 2.86 (s, 3H, ArCH3), 2.28-2.40 (m, 2H, oxosultone), 1.84 (s, 3H, ArCH3), 1.69 (quin, 2H, CH2), 1.37 (quin, 2H, CH2), 1.24-1.26 (m, 4H, CH2), 0.82 (t, 3H, CH3) 19F-NMR(DMSO, 376 MHz): δ (ppm) = −106.7 | 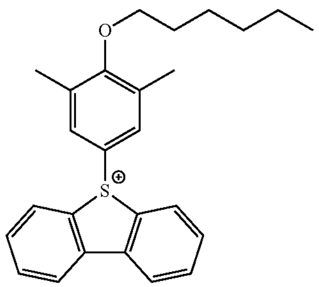 [SMILES: CCCCCCOc1c(C)cc(-[s+]2c3ccccc3c3ccccc32)cc1C] | 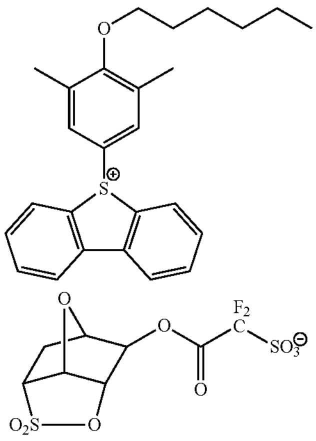 |

TABLE 8
| Compound | NMR | Cation | Product |
|---|---|---|---|
| (B)-23 | 1H-NMR (DMSO, 400 MHz): δ (ppm) = 7.99-8.01 (d, 2H, ArH), 7.73-7.76 (t, 1H, ArH), 7.58-7.61 (t, 2H, ArH), 5.76 (d, 1H, CH), 5.31 (s, 2H, SCH2C=O), 4.87-5.05 (m, 3H, CH), 4.23 (m, 1H, CH), 3.49-3.62 (m, 4H, CH2), 2.18-2.49 (m, 6H, CH2 + oxosultone) 19F-NMR (DMSO, 376 MHz): δ (ppm) = −106.7 | 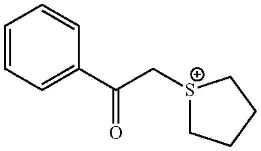 [SMILES: O=C(C[S+]1CCCC1)c1ccccc1] | 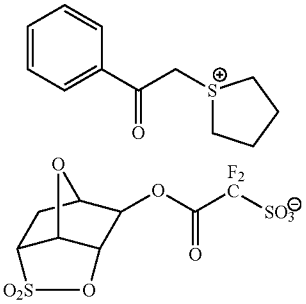 |
| (B)-24 | 1H-NMR (DMSO, 400 MHz): δ (ppm) = 8.02-8.05 (m, 2H, ArH), 7.61-7.73 (m, 3H, ArH), 5.76 (d, 1H, CH), 4.87-5.05 (m, 3H, CH), 4.23 (m, 1H, CH), 3.76-3.86 (m, 4H, SCH2), 2.28-2.40 (m, 2H, oxosultone), 2.09-2.12 (m, 2H, CH2), 1.84-1.93 (m, 2H, CH2), 1.61-1.70 (m, 2H, CH2) 19F-NMR (DMSO, 376 MHz): δ (ppm) = −106.7 | 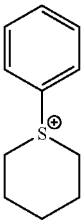 [SMILES: c1ccc([S+]2CCCCC2)cc1] | 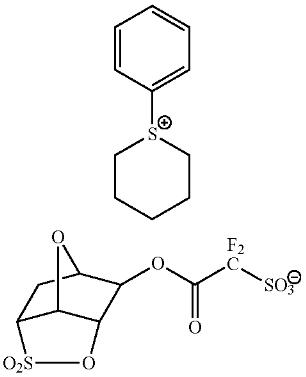 |
| (B)-25 | 1H-NMR (DMSO, 400 MHz): δ (ppm) = 8.04-8.09 (m 2H, ArH), 7.69-7.79 (m, 3H, ArH), 5.76 (d, 1H, CH), 4.87-5.05 (m, 3H, CH), 4.23 (m, 1H, CH), 3.29 (s, 6H, CH3), 2.28-2.40 (m, 2H, oxosultone) 19F-NMR (DMSO, 376 MHz): δ (ppm) = −106.7 | 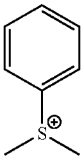 | 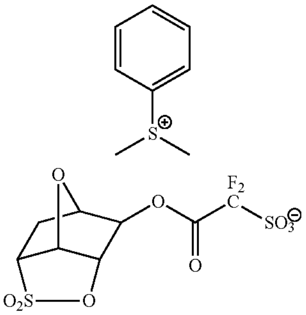 |

TABLE 9
| Compound | NMR | Cation | Product |
|---|---|---|---|
| (B)-26 | 1H-NMR (DMSO, 400 MHz): δ (ppm) = 8.07 (d, 2H, ArH), 7.81 (d, 2H, ArH), 5.76 (d, 1H, CH), 4.87-5.05 (m, 3H, CH), 4.23 (m, 1H, CH), 4.10 (t, 2H, CH2), 3.59 (d, 2H, CH2), 1.71-2.40 (m, 8H, CH2 + CH2 + oxosultone), 1.23 (s, 9H, t-Bu) 19F-NMR (DMSO, 376 MHz): δ (ppm) = −106.7 | 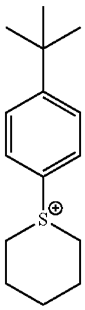 [SMILES: CC(C)(C)c1ccc([S+]2CCCCC2)cc1] | 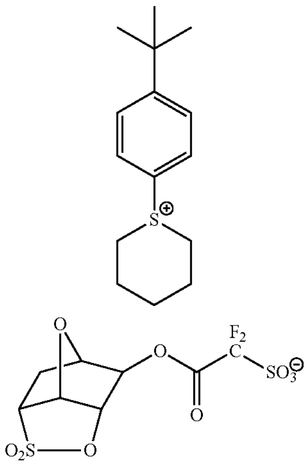 |
| (B)-27 | 1H-NMR (DMSO, 400 MHz): δ (ppm) = 7.75 (s, 2H, ArH), 5.76 (d, 1H, CH), 4.87-5.05 (m, 3H, CH), 4.23(m, 1H, CH), 3.91-3.96 (m, 2H CH2), 3.72-3.79 (m, 2H, CH2), 2.29-2.41 (m, 6H, CH2 + oxosultone), 1.75-2.19 (m, 21H, CH3 + Adamantane) 19F-NMR (DMSO, 376 MHz): δ (ppm) = −106.7 | 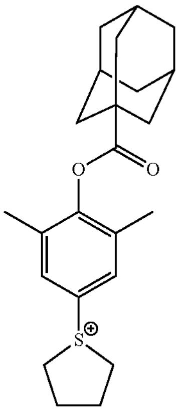 [SMILES: Cc1cc([S+]2CCCC2)cc(C)c1OC(=O)C12CC3CC(CC(C3)C1)C2] | 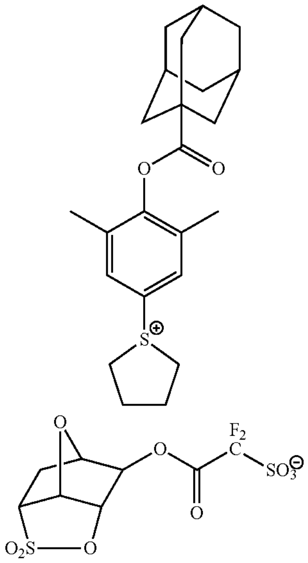 |

TABLE 9-continued

| Compound | NMR | Cation | Product |
|---|---|---|---|
| (B)-28 | 1H-NMR (DMSO, 400 MHz): δ (ppm) = 7.82 (m, 2H, ArH), 5.76 (d, 1H, CH), 4.87-5.05 (m, 3H, CH), 4.23 (m, 1H, CH), 3.73-3.91 (m, 4H, CH2), 1.56-2.43 (m, 29H, CH3 + CH2 + adamantane + oxosultone)<br>19F-NMR (DMSO, 376 MHz): δ (ppm) = −106.7 | 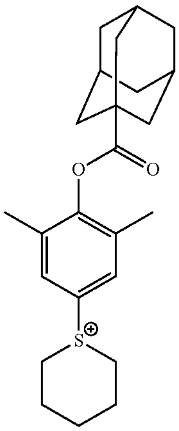 [SMILES: Cc1cc([S+]2CCCCC2)cc(C)c1OC(=O)C12CC3CC(CC(C3)C1)C2] | 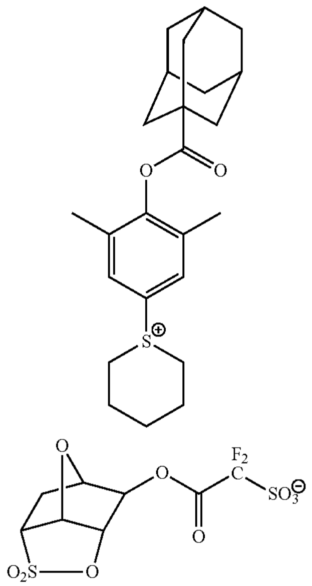 |

TABLE 10

| Compound | NMR | Cation | Product |
|---|---|---|---|
| (B)-29 | 1H-NMR (DMSO, 400 MHz): δ (ppm) = 8.28 (d, 2H, ArH), 8.12 (d, 1H, ArH), 7.86 (t, 1H, ArH), 7.63-7.81 (m, 7H, ArH), 5.76 (d, 1H, CH), 4.87-5.05 (m, CH), 4.23 (m, 1H, CH), 2.28-2.40 (m, 2H, oxosultone)<br>19F-NMR (DMSO, 376 MHz): δ (ppm) = −106.7 | 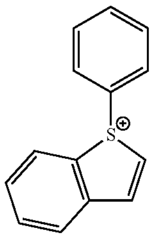 [SMILES: c1ccc(-[s+]2ccc3ccccc32)cc1] | 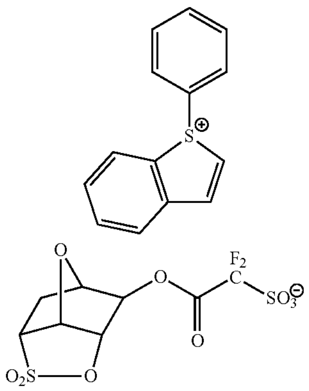 |
| (B)-30 | 1H-NMR (DMSO, 400 MHz): δ (ppm) = 8.28 (d, 2H, ArH), 8.12 (d, 1H, ArH), 7.88 (t, 1H, ArH), 7.80 (d, 1H, ArH), 7.62-7.74 (m, 5H, ArH), 5.76 (d, 1H, CH), 4.87-5.05 (m, 3H, CH), 4.23 (m, 1H, CH), 2.28-2.40 (m, 2H, oxosultone), 1.27 (s, 9H, CH3)<br>19F-NMR (DMSO, 376 MHz): δ (ppm) = −106.7 | 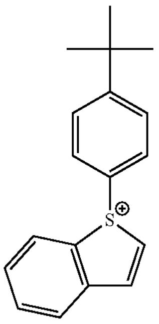 [SMILES: CC(C)(C)c1ccc(-[s+]2ccc3ccccc32)cc1] | 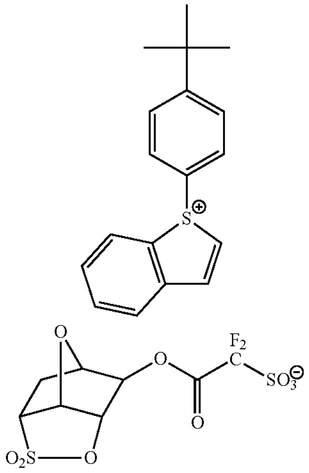 |

TABLE 10-continued

| Compound | NMR | Cation | Product |
|---|---|---|---|
| (B)-31 | 1H-NMR (DMSO, 400 MHz): δ (ppm) = 8.50 (d, 2H, ArH), 8.37 (d, 2H, ArH), 7.93 (t, 2H, ArH), 7.55-7.75 (m, 7H, ArH), 5.76 (d, 1H, CH), 4.87-5.05 (m, 3H, CH), 4.23 (m, 1H, CH), 2.28-2.40 (m, 2H, oxosultone) 19F-NMR (DMSO, 376 MHz): δ (ppm) = −106.7 | 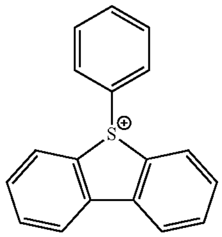 [SMILES: c1ccc(-[s+]2c3ccccc3c3ccccc32)cc1] | 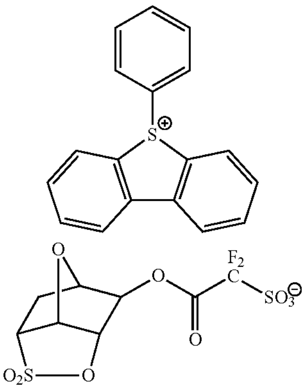 |

TABLE 11

| Compound | NMR | Cation | Product |
|---|---|---|---|
| (B)-32 | 1H-NMR (DMSO, 400 MHz): δ (ppm) = 8.44 (d, 1H, ArH), 8.22 (m, 2H, ArH), 7.73-7.89 (m, 13H, ArH), 7.50 (d, 1H, ArH), 5.76 (d, 1H, CH), 4.87-5.05 (m, 3H, CH), 4.23 (m, 1H, CH), 2.28-2.40 (m, 2H, oxosultone) 19F-NMR (DMSO, 376 MHz): δ (ppm) = −106.7 | 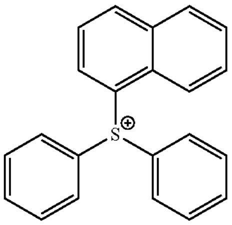 [SMILES: c1ccc([S+](c2ccccc2)c2cccc3ccccc23)cc1] | 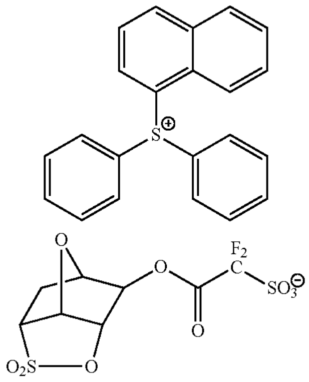 |
| (B)-33 | 1H-NMR (DMSO, 400 MHz): δ (ppm) = 8.41 (m, 2H ArH), 3.12 (d, 1H, ArH), 7.73-7.93 (m, 2H, ArH), 7.19 (d, 1H, ArH), 5.76 (d, 1H, CH), 5.23 (s, 2H, CH2), 4.87-5.05 (m, 4H, Adamantane + CH), 4.23 (m, 3H, CH2S + CH), 3.75 (m, 2H, CH2S), 2.27-2.43 (m, 6H, SCH2CH2 + oxolactone), 1.42-1.99 (m, 14H, Adamantane) 19F-NMR (DMSO, 376 MHz): δ (ppm) = −106.7 | 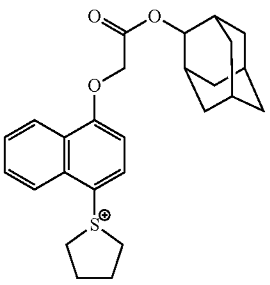 [SMILES: O=C(COc1ccc([S+]2CCCC2)c2ccccc12)OC1C2CC3CC(C2)CC1C3] | 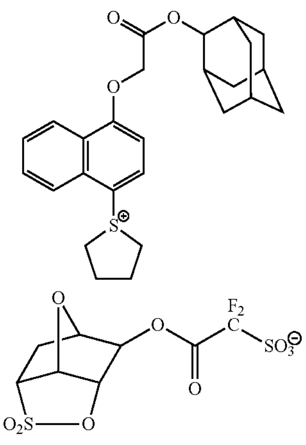 |

TABLE 11-continued

| Compound | NMR | Cation | Product |
|---|---|---|---|
| (B)-34 | 1H-NMR (DMSO, 400 MHz): δ (ppm) = 8.42 (m, 2H ArH), 8.17 (d, 1H, ArH), 7.78-7.91 (m, 2H, ArH), 7.23 (d, 1H, ArH), 5.76 (d, 1H, CH), 5.26 (s, 2H, CH2), 4.87-5.05 (m, 3H, CH), 3.75-4.23 (m, 8H, SCH2 + CH3 + CH), 2.28-2.60 (m, 6H, SCH2CH2 + oxolactone) 19F-NMR (DMSO, 376 MHz): δ (ppm) = −106.7 | 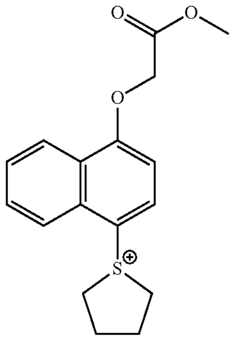 [SMILES: COC(=O)COc1ccc([S+]2CCCC2)c2ccccc12] | 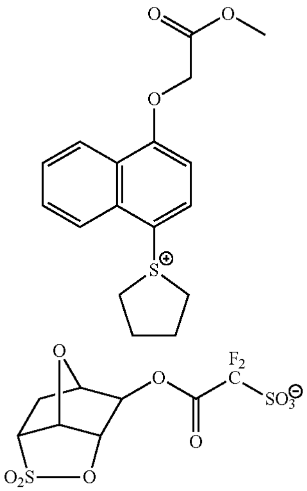 |

TABLE 12

| Compound | NMR | Cation | Product |
|---|---|---|---|
| (B)-35 | 1H-NMR (DMSO, 400 MHz): δ (ppm) = 8.55 (d, 2H, ArH), 8.38 (d, 2H, ArH), 8.32 (d, 2H, ArH), 8.03 (d, 2H, ArH), 7.93-7.97 (m, 1H, ArH), 7.82-7.88 (m, 8H, ArH), 7.55 (d, 2H, ArH), 5.76 (d, 1H, CH), 4.87-5.05 (m, 3H, CH), 4.23 (m, 1H, CH), 2.28-2.40 (m, 2H, oxosultone) 19F-NMR (DMSO, 376 MHz): δ (ppm) = −106.7 | 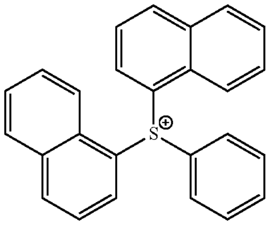 [SMILES: c1ccc([S+](c2cccc3ccccc23)c2cccc3ccccc23)cc1] | 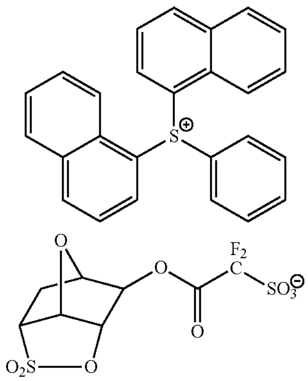 |
| (B)-36 | 1H-NMR (DMSO, 400 MHz): δ (ppm) = 7.78-7.89 (m, 10H, ArH), 7.64 (s, 2H, ArH), 5.76 (d, 1H, CH), 4.87-5.05 (m, 3H, CH), 4.23 (m, 1H, CH), 3.79 (s, 3H, OCH3), 2.28-2.40 (m, 8H, CH3 + oxosultone) 19F-NMR (DMSO, 376 MHz): δ (ppm) = −106.7 | 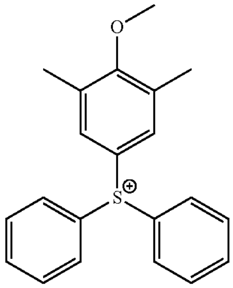 [SMILES: COc1c(C)cc([S+](c2ccccc2)c2ccccc2)cc1C] | 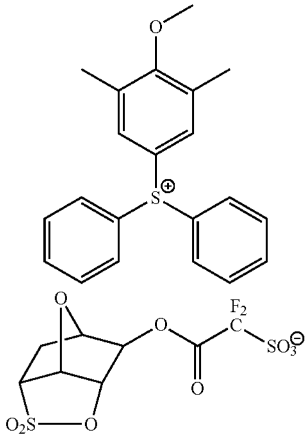 |

TABLE 12-continued

| Compound | NMR | Cation | Product |
|---|---|---|---|
| (B)-37 | 1H-NMR (DMSO, 400 MHz): δ (pprn) = 7.72-7.84 (m, 10H, ArH), 1.59 (s, 2H, ArH), 5.76 (d, 1H, CH) 4.87-5.05 (m, 3H, CH), 4.56 (s, 2H, CH2), 4.23 (m, 1H, CH), 2.27-2.48 (m, 17H, CH3 + Adamantane + oxosultane), 1.94-1.97 (m, 2H, Adamantane), 1.72-1.79 (m, 2H, Adamantane)<br>19F-NMR (DMSO, 376 MHz): δ (ppm) = −106.7 | 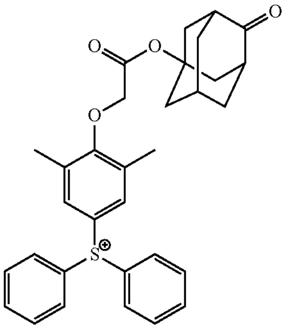 [SMILES: Cc1cc([S+](c2ccccc2)c2ccccc2)cc(C)c1OCC(=O)OC12CC3CC(C1)C(=O)C(C3)C2] | 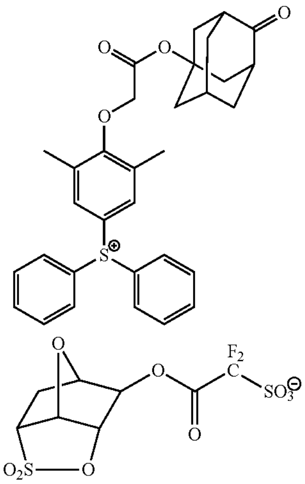 |

TABLE 13

| Compound | NMR | Cation | Product |
|---|---|---|---|
| (B)-38 | 1H-NMR (DMSO, 400 MHz): δ (ppm) = 7.77-7.98 (m, 10H, ArH), 7.64 (s, 2H, ArH), 5.76 (d, 1H, CH), 4.87-5.05 (m, 3H, CH), 4.57 (s, 2H, CH2O), 4.23 (m, 1H, CH), 2.25-2.40 (m, 17H, CH3 + Adamantane + oxosultone), 1.76 (br s, 6H, Adamantane)<br>19F-NMR (DMSO, 376 MHz): δ (ppm) = −106.7 | 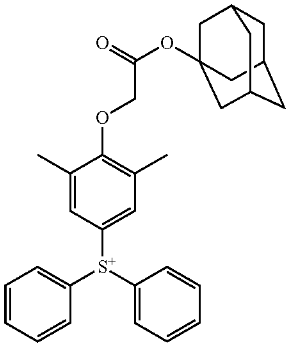 [SMILES: Cc1cc([S+](c2ccccc2)c2ccccc2)cc(C)c1OCC(=O)OC12CC3CC(CC(C3)C1)C2] | 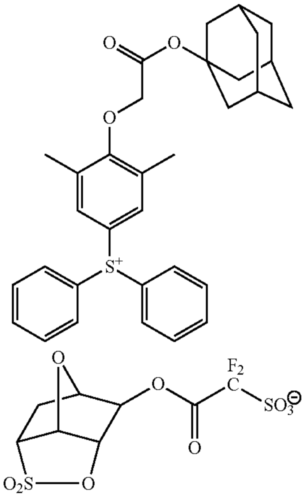 |
| (B)-39 | 1H-NMR (DMSO, 400 MHz): δ (ppm) = 7.76-7.87 (m, 10H, ArH), 7.69 (s, 2H, ArH), 5.76 (d, 1H, CH), 4.87-5.05 (m, 3H, CH), 4.23 (m, 1H, CH), 2.18-2.40 (m, 8H, CH3 + oxosultone), 1.66-2.03 (m, 15H, Adamantane)<br>19F-NMR (DMSO, 376 MHz): δ (ppm) = −106.7 | 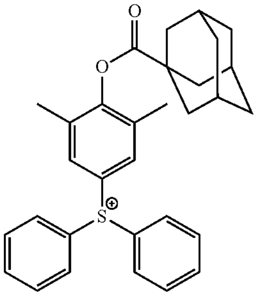 [SMILES: Cc1cc([S+](c2ccccc2)c2ccccc2)cc(C)c1OC(=O)C12CC3CC(CC(C3)C1)C2] | 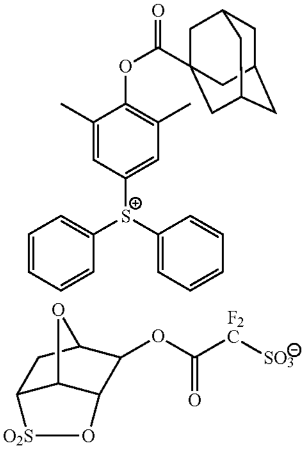 |

TABLE 13-continued

| Compound | NMR | Cation | Product |
|---|---|---|---|
| (B)-40 | 1H-NMR (DMSO, 400 MHz): δ (ppm) = 7.77-7.89 (m, 10H, ArH), 7.71 (s, 2H, ArH), 5.76 (d, 1H, CH), 4.87-5.05 (m, 3H, CH), 4.23 (m, 1H, CH), 2.51 (s, 2H, CH2), 2.28-2.40 (m, 8H, CH3 + oxosultone), 1.97 (s, 3H, Adamantane), 1.62-1.73 (m, 12H, Adamantane) 19F-NMR (DMSO, 376 MHz): δ (ppm) = −106.7 | 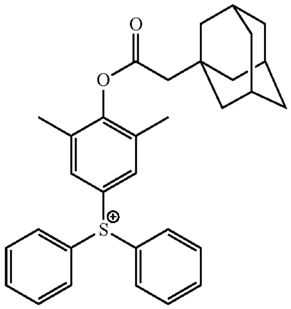 [SMILES: Cc1cc([S+](c2ccccc2)c2ccccc2)cc(C)c1OC(=O)CC12CC3CC(CC(C3)C1)C2] | 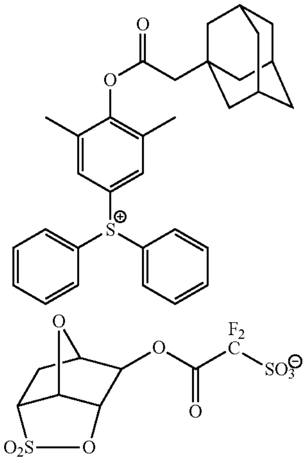 |

TABLE 14

| Compound | NMR | Cation | Product |
|---|---|---|---|
| (B)-41 | 1H-NMR (DMSO, 400 MHz): δ (ppm) = 7.79-7.93 (m, 12H, ArH), 5.76 (d, 1H, CH), 4.87-5.05 (m, 3H, CH), 4.23 (m, 1H, CH), 2.73 (t, 2H, CO—CH2), 2.20-2.40 (m, 8H, CH3 + oxosultone), 1.65-1.72 (m, 2H, CH2), 1.25-1.38 (m, 14H, CH2), 0.85 (t, 3H, CH3) 19F-NMR (DMSO, 376 MHz): δ (ppm) = −106.7 | 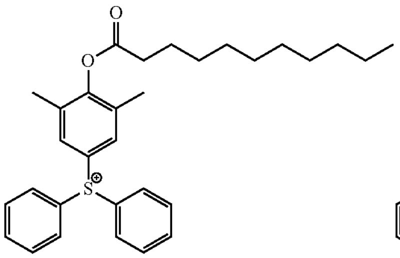 | 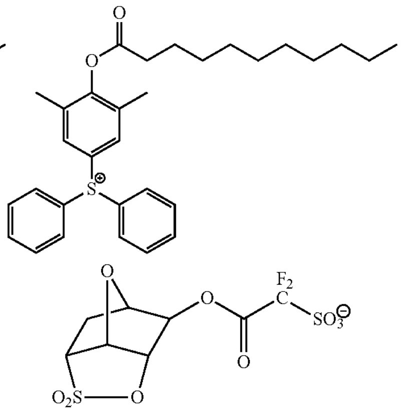 |
| (B)-42 | 1H-NMR (DMSO, 400 MHz): δ (ppm) = 8.29 (d, 4H, ArH), 7.93-8.09 (m, 6H, ArH), 5.76 (d, 1H, CH), 4.87-5.05 (m, 3H, CH), 4.23 (m, 1H, CH), 2.28-2.40 (m, 2H, oxosultone) 19F-NMR (DMSO, 376 MHz): δ (ppm) = −47.9, −106.7 | 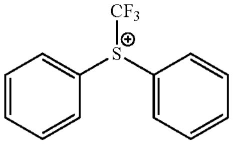 [SMILES: FC(F)(F)[S+](c1ccccc1)c1ccccc1] | 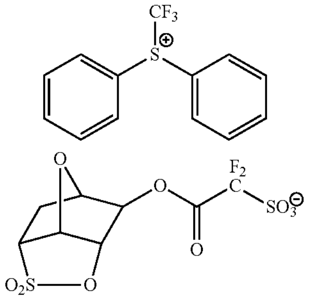 |

TABLE 14-continued

| Compound | NMR | Cation | Product |
|---|---|---|---|
| (B)-43 | 1H-NMR (DMSO, 400 MHz): δ (ppm) = 8.24 (d, 4H, ArH), 7.59 (t, 2H, ArH), 7.47 (t, 4H, ArH), 5.76 (d, 1H, CH), 4.87-5.05 (m, 3H, CH), 4.23 (m, 1H, CH), 2.28-2.40 (m, 2H, oxosultone) 19F-NMR (DMSO, 376 MHz): δ (ppm) = −106.7 | 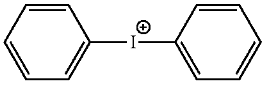 [SMILES: c1ccc([I+]c2ccccc2)cc1] | 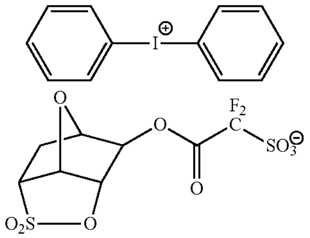 |

TABLE 15

| Compound | NMR | Cation | Product |
|---|---|---|---|
| (B)-44 | 1H-NMR (DMSO, 400 MHz): δ (ppm) = 5.76 (d, 1H, CH), 4.87-5.05 (m, 3H, CH), 4.23 (m, 1H, CH), 3.36 (t, 6H, CH2), 2.28-2.40 (m, 2H, oxosultone) 1.68 (quintet, 6H, CH2), 1.35-1.44 (m, 6H, CH2), 0.81-0.93 (m, 9H, CH3) 19F-NMR (DMSO, 376 MHz): δ (ppm) = −106.7 | 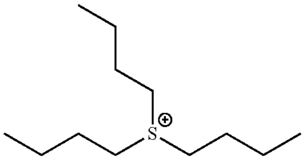 | 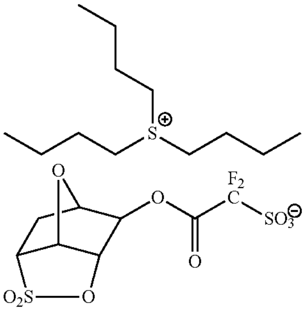 |
| (B)-45 | 1H-NMR (DMSO, 400 MHz): δ (ppm) = 7.75-7.87 (m, 10H ArH), 7.62 (s, 2H, ArH), 5.76 (d, 1H, CH), 4.87-5.05 (m, 3H, CH), 4.23 (m, 1H, CH), 3.97 (t, 2H, CH2), 2.03-2.56 (m, 12H CH2 + CH3 + oxosultone) 19F-NMR (DMSO, 376 MHz): δ (ppm) = −123.5, −121.8, −111.8, −106.7, −78.3 | 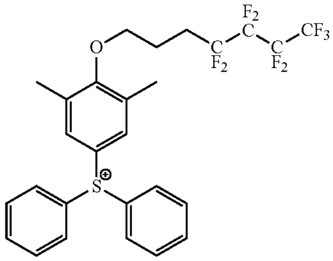 [SMILES: Cc1cc([S+](c2ccccc2)c2ccccc2)cc(C)c1OCCCC(F)(F)C(F)(F)C(F)(F)C(F)(F)F] | 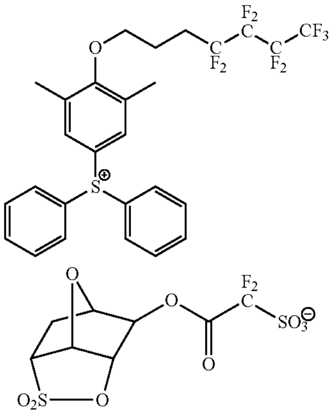 |
| (B)-46 | 1H-NMR (DMSO, 400 MHz): δ (ppm) = 7.75-7.86 (m, 10H, ArH), 7.60 (s, 2H, ArH), 5.76 (d, 1H, CH), 4.87-5.05 (m, 3H, CH), 4.23 (m, 1H, CH), 3.87 (t, 2H, CH2), 2.23-2.40 (m, 10H, CH2 + CH3 + oxosultone), 2.12 (m, 6H, N—CH3), 1.86 (t, 2H, CH2) 19F-NMR (DMSO, 376 MHz): δ (ppm) = −106.7 | 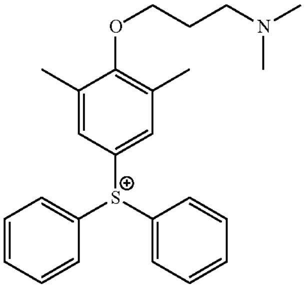 [SMILES: Cc1cc([S+](c2ccccc2)c2ccccc2)cc(C)c1OCCCN(C)C] | 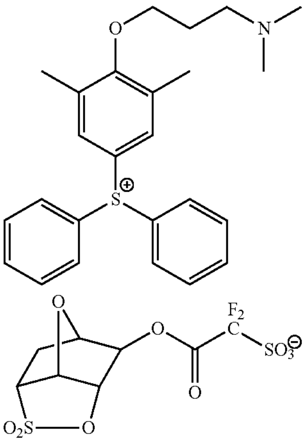 |

Examples 1 to 51, Comparative Examples 1 to 47

The components shown in Tables 16 to 21 were mixed together and dissolved to obtain positive resist compositions.

TABLE 16

| | Component (A) | Component (B) | Component (D) | Component (E) | Component (S) | |
|---|---|---|---|---|---|---|
| Example 1 | (A)-1 [100] | (B)-1 [8.70] | (D)-1 [1.20] | (E)-1 [1.32] | (S)-1 [10] | (S)-2 [2577] |
| Example 2 | (A)-1 [100] | (B)-2 [8.76] | (D)-1 [1.20] | (E)-1 [1.32] | (S)-1 [10] | (S)-2 [2577] |
| Example 3 | (A)-1 [100] | (B)-3 [8.00] | (D)-1 [1.20] | (E)-1 [1.32] | (S)-1 [10] | (S)-2 [2577] |
| Example 4 | (A)-1 [100] | (B)-4 [11.45] | (D)-1 [1.20] | (E)-1 [1.32] | (S)-1 [10] | (S)-2 [2577] |
| Example 5 | (A)-1 [100] | (B)-5 [11.06] | (D)-1 [1.20] | (E)-1 [1.32] | (S)-1 [10] | (S)-2 [2577] |
| Example 6 | (A)-1 [100] | (B)-6 [10.70] | (D)-1 [1.20] | (E)-1 [1.32] | (S)-1 [10] | (S)-2 [2577] |
| Example 7 | (A)-1 [100] | (B)-7 [10.12] | (D)-1 [1.20] | (E)-1 [1.32] | (S)-1 [10] | (S)-2 [2577] |
| Example 8 | (A)-2 [100] | (B)-8 [11.95] | (D)-1 [1.20] | (E)-1 [1.32] | (S)-1 [10] | (S)-2 [2577] |
| Example 9 | (A)-2 [100] | (B)-9 [9.12] | (D)-1 [1.20] | (E)-1 [1.32] | (S)-1 [10] | (S)-2 [2577] |
| Example 10 | (A)-1 [100] | (B)-10 [9.92] | (D)-1 [1.20] | (E)-1 [1.32] | (S)-1 [10] | (S)-2 [2577] |
| Example 11 | (A)-1 [100] | (B)-11 [9.09] | (D)-1 [1.20] | (E)-1 [1.32] | (S)-1 [10] | (S)-2 [2577] |
| Example 12 | (A)-1 [100] | (B)-12 [11.76] | (D)-1 [1.20] | (E)-1 [1.32] | (S)-1 [10] | (S)-2 [2577] |
| Example 13 | (A)-1 [100] | (B)-13 [12.31] | (D)-1 [1.20] | (E)-1 [1.32] | (S)-1 [10] | (S)-2 [2577] |
| Example 14 | (A)-1 [100] | (B)-14 [11.84] | (D)-1 [1.20] | (E)-1 [1.32] | (S)-1 [10] | (S)-2 [2577] |
| Example 15 | (A)-1 [100] | (B)-15 [11.81] | (D)-1 [1.20] | (E)-1 [1.32] | (S)-1 [10] | (S)-2 [2577] |
| Example 16 | (A)-1 [100] | (B)-16 [11.09] | (D)-1 [1.20] | (E)-1 [1.32] | (S)-1 [10] | (S)-2 [2577] |
| Example 17 | (A)-1 [100] | (B)-17 [12.20] | (D)-1 [1.20] | (E)-1 [1.32] | (S)-1 [10] | (S)-2 [2577] |

TABLE 17

| | Component (A) | Component (B) | Component (D) | Component (E) | Component (S) | |
|---|---|---|---|---|---|---|
| Example 18 | (A)-1 [100] | (B)-18 [12.34] | (D)-1 [1.20] | (E)-1 [1.32] | (S)-1 [10] | (S)-2 [2577] |
| Example 19 | (A)-1 [100] | (B)-19 [10.29] | (D)-1 [1.20] | (E)-1 [1.32] | (S)-1 [10] | (S)-2 [2577] |
| Example 20 | (A)-1 [100] | (B)-20 [10.84] | (D)-1 [1.20] | (E)-1 [1.32] | (S)-1 [10] | (S)-2 [2577] |
| Example 21 | (A)-1 [100] | (B)-21 [9.20] | (D)-1 [1.20] | (E)-1 [1.32] | (S)-1 [10] | (S)-2 [2577] |
| Example 22 | (A)-1 [100] | (B)-22 [10.26] | (D)-1 [1.20] | (E)-1 [1.32] | (S)-1 [10] | (S)-2 [2577] |
| Example 23 | (A)-1 [100] | (B)-23 [7.73] | (D)-1 [1.20] | (E)-1 [1.32] | (S)-1 [10] | (S)-2 [2577] |
| Example 24 | (A)-1 [100] | (B)-24 [7.34] | (D)-1 [1.20] | (E)-1 [1.32] | (S)-1 [10] | (S)-2 [2577] |
| Example 25 | (A)-1 [100] | (B)-25 [6.78] | (D)-1 [1.20] | (E)-1 [1.32] | (S)-1 [10] | (S)-2 [2577] |
| Example 26 | (A)-1 [100] | (B)-26 [8.12] | (D)-1 [1.20] | (E)-1 [1.32] | (S)-1 [10] | (S)-2 [2577] |
| Example 27 | (A)-1 [100] | (B)-27 [10.01] | (D)-1 [1.20] | (E)-1 [1.32] | (S)-1 [10] | (S)-2 [2577] |
| Example 28 | (A)-2 [100] | (B)-28 [10.20] | (D)-1 [1.20] | (E)-1 [1.32] | (S)-1 [10] | (S)-2 [2577] |
| Example 29 | (A)-2 [100] | (B)-29 [7.78] | (D)-1 [1.20] | (E)-1 [1.32] | (S)-1 [10] | (S)-2 [2577] |
| Example 30 | (A)-1 [100] | (B)-30 [8.56] | (D)-1 [1.20] | (E)-1 [1.32] | (S)-1 [10] | (S)-2 [2577] |
| Example 31 | (A)-1 [100] | (B)-31 [8.48] | (D)-1 [1.20] | (E)-1 [1.32] | (S)-1 [10] | (S)-2 [2577] |
| Example 32 | (A)-1 [100] | (B)-32 [9.20] | (D)-1 [1.20] | (E)-1 [1.32] | (S)-1 [10] | (S)-2 [2577] |
| Example 33 | (A)-1 [100] | (B)-33 [10.73] | (D)-1 [1.20] | (E)-1 [1.32] | (S)-1 [10] | (S)-2 [2577] |
| Example 34 | (A)-1 [100] | (B)-34 [9.06] | (D)-1 [1.20] | (E)-1 [1.32] | (S)-1 [10] | (S)-2 [2577] |

TABLE 18

| | Component (A) | Component (B) | Component (D) | | Component (E) | Component (S) | |
|---|---|---|---|---|---|---|---|
| Example 35 | (A)-1 [100] | (B)-35 [9.90] | (D)-1 [1.20] | | (E)-1 [1.32] | (S)-1 [10] | (S)-2 [2577] |
| Example 36 | (A)-1 [100] | (B)-36 [9.31] | (D)-1 [1.20] | | (E)-1 [1.32] | (S)-1 [10] | (S)-2 [2577] |
| Example 37 | (A)-1 [100] | (B)-37 [11.98] | (D)-1 [1.20] | | (E)-1 [1.32] | (S)-1 [10] | (S)-2 [2577] |
| Example 38 | (A)-1 [100] | (B)-38 [11.79] | (D)-1 [1.20] | | (E)-1 [1.32] | (S)-1 [10] | (S)-2 [2577] |
| Example 39 | (A)-1 [100] | (B)-39 [11.37] | (D)-1 [1.20] | | (E)-1 [1.32] | (S)-1 [10] | (S)-2 [2577] |
| Example 40 | (A)-1 [100] | (B)-40 [11.56] | (D)-1 [1.20] | | (E)-1 [1.32] | (S)-1 [10] | (S)-2 [2577] |
| Example 41 | (A)-1 [100] | (B)-41 [11.45] | (D)-1 [1.20] | | (E)-1 [1.32] | (S)-1 [10] | (S)-2 [2577] |
| Example 42 | (A)-1 [100] | (B)-45 [12.73] | (D)-1 [1.20] | | (E)-1 [1.32] | (S)-1 [10] | (S)-2 [2577] |
| Example 43 | (A)-1 [100] | (B)-42 [8.39] | (D)-1 [1.20] | | (E)-1 [1.32] | (S)-1 [10] | (S)-2 [2577] |
| Example 44 | (A)-1 [100] | (B)-43 [8.75] | (D)-1 [1.20] | | (E)-1 [1.32] | (S)-1 [10] | (S)-2 [2577] |
| Example 45 | (A)-2 [100] | (B)-1 [8.70] | (D)-1 [1.20] | | (E)-1 [1.32] | (S)-1 [10] | (S)-2 [2577] |
| Example 46 | (A)-2 [100] | (B)-3 [11.26] | (D)-1 [1.20] | | (E)-1 [1.32] | (S)-1 [10] | (S)-2 [2577] |
| Example 47 | (A)-1 [100] | (B)-1 [8.70] | (D)-2 [2.61] | | (E)-1 [1.32] | (S)-1 [10] | (S)-2 [2577] |
| Example 48 | (A)-1 [100] | (B)-1 [8.70] | (D)-1 [1.20] | (D)-2 [3.79] | (E)-1 [1.32] | (S)-1 [10] | (S)-2 [2577] |

TABLE 18-continued

| | Component (A) | Component (B) | Component (D) | Component (E) | Component (S) | |
|---|---|---|---|---|---|---|
| Example 49 | (A)-1 [100] | (B)-1 [8.70] | (D)-3 [3.10] | (E)-1 [1.32] | (S)-1 [10] | (S)-2 [2577] |
| Example 50 | (A)-1 [100] | (B)-1 [8.70] | (D)-4 [2.40] | (E)-1 [1.32] | (S)-1 [10] | (S)-2 [2577] |
| Example 51 | (A)-1 [100] | (B)-1 [8.70] | (D)-5 [2.76] | (E)-1 [1.32] | (S)-1 [10] | (S)-2 [2577] |

TABLE 19

| | Component (A) | Component (B) | Component (D) | Component (E) | Component (S) | |
|---|---|---|---|---|---|---|
| Comparative Example 1 | (A)-1 [100] | (B)-1A [8.80] | (D)-1 [1.20] | (E)-1 [1.32] | (S)-1 [10] | (S)-2 [2577] |
| Comparative Example 2 | (A)-1 [100] | (B)-1B [8.00] | (D)-1 [1.20] | (E)-1 [1.32] | (S)-1 [10] | (S)-2 [2577] |
| Comparative Example 3 | (A)-1 [100] | (B)-2A [12.08] | (D)-1 [1.20] | (E)-1 [1.32] | (S)-1 [10] | (S)-2 [2577] |
| Comparative Example 4 | (A)-1 [100] | (B)-3A [11.36] | (D)-1 [1.20] | (E)-1 [1.32] | (S)-1 [10] | (S)-2 [2577] |
| Comparative Example 5 | (A)-1 [100] | (B)-4A [11.55] | (D)-1 [1.20] | (E)-1 [1.32] | (S)-1 [10] | (S)-2 [2577] |
| Comparative Example 6 | (A)-1 [100] | (B)-5A [11.16] | (D)-1 [1.20] | (E)-1 [1.32] | (S)-1 [10] | (S)-2 [2577] |
| Comparative Example 7 | (A)-1 [100] | (B)-6A [10.80] | (D)-1 [1.20] | (E)-1 [1.32] | (S)-1 [10] | (S)-2 [2577] |
| Comparative Example 8 | (A)-2 [100] | (B)-7A [10.21] | (D)-1 [1.20] | (E)-1 [1.32] | (S)-1 [10] | (S)-2 [2577] |
| Comparative Example 9 | (A)-2 [100] | (B)-8A [12.05] | (D)-1 [1.20] | (E)-1 [1.32] | (S)-1 [10] | (S)-2 [2577] |
| Comparative Example 10 | (A)-1 [100] | (B)-9A [9.21] | (D)-1 [1.20] | (E)-1 [1.32] | (S)-1 [10] | (S)-2 [2577] |
| Comparative Example 11 | (A)-1 [100] | (B)-10A [10.02] | (D)-1 [1.20] | (E)-1 [1.32] | (S)-1 [10] | (S)-2 [2577] |
| Comparative Example 12 | (A)-1 [100] | (B)-11A [9.19] | (D)-1 [1.20] | (E)-1 [1.32] | (S)-1 [10] | (S)-2 [2577] |
| Comparative Example 13 | (A)-1 [100] | (B)-12A [11.85] | (D)-1 [1.20] | (E)-1 [1.32] | (S)-1 [10] | (S)-2 [2577] |
| Comparative Example 14 | (A)-1 [100] | (B)-13A [12.41] | (D)-1 [1.20] | (E)-1 [1.32] | (S)-1 [10] | (S)-2 [2577] |
| Comparative Example 15 | (A)-1 [100] | (B)-14A [11.94] | (D)-1 [1.20] | (E)-1 [1.32] | (S)-1 [10] | (S)-2 [2577] |
| Comparative Example 16 | (A)-1 [100] | (B)-15A [11.91] | (D)-1 [1.20] | (E)-1 [1.32] | (S)-1 [10] | (S)-2 [2577] |
| Comparative Example 17 | (A)-1 [100] | (B)-16A [11.19] | (D)-1 [1.20] | (E)-1 [1.32] | (S)-1 [10] | (S)-2 [2577] |

TABLE 20

| | Component (A) | Component (B) | Component (D) | Component (E) | Component (S) | |
|---|---|---|---|---|---|---|
| Comparative Example 18 | (A)-1 [100] | (B)-17A [12.30] | (D)-1 [1.20] | (E)-1 [1.32] | (S)-1 [10] | (S)-2 [2577] |
| Comparative Example 19 | (A)-1 [100] | (B)-18A [12.44] | (D)-1 [1.20] | (E)-1 [1-32] | (S)-1 [10] | (S)-2 [2577] |
| Comparative Example 20 | (A)-1 [100] | (B)-19A [10.38] | (D)-1 [1.20] | (E)-1 [1.32] | (S)-1 [10] | (S)-2 [2577] |
| Comparative Example 21 | (A)-1 [100] | (B)-20A [10.94] | (D)-1 [1.20] | (E)-1 [1.32] | (S)-1 [10] | (S)-2 [2577] |
| Comparative Example 22 | (A)-1 [100] | (B)-21A [9.30] | (D)-1 [1.20] | (E)-1 [1-32] | (S)-1 [10] | (S)-2 [2577] |
| Comparative Example 23 | (A)-1 [100] | (B)-22A [10.35] | (D)-1 [1.20] | (E)-1 [1.32] | (S)-1 [10] | (S)-2 [2577] |
| Comparative Example 24 | (A)-1 [100] | (B)-23A [7.82] | (D)-1 [1.20] | (E)-1 [1.32] | (S)-1 [10] | (S)-2 [2577] |
| Comparative Example 25 | (A)-1 [100] | (B)-24A [7.44] | (D)-1 [1.20] | (E)-1 [1.32] | (S)-1 [10] | (S)-2 [2577] |
| Comparative Example 26 | (A)-1 [100] | (B)-25A [6.88] | (D)-1 [1.20] | (E)-1 [1.32] | (S)-1 [10] | (S)-2 [2577] |
| Comparative Example 27 | (A)-1 [100] | (B)-26A [8.21] | (D)-1 [1.20] | (E)-1 [1.32] | (S)-1 [10] | (S)-2 [2577] |

TABLE 20-continued

| | Component (A) | Component (B) | Component (D) | Component (E) | Component (S) | |
|---|---|---|---|---|---|---|
| Comparative Example 28 | (A)-2 [100] | (B)-27A [10.10] | (D)-1 [1.20] | (E)-1 [1.32] | (S)-1 [10] | (S)-2 [2577] |
| Comparative Example 29 | (A)-2 [100] | (B)-28A [10.30] | (D)-1 [1.20] | (E)-1 [1.32] | (S)-1 [10] | (S)-2 [2577] |
| Comparative Example 30 | (A)-1 [100] | (B)-29A [7.88] | (D)-1 [1.20] | (E)-1 [1.32] | (S)-1 [10] | (S)-2 [2577] |
| Comparative Example 31 | (A)-1 [100] | (B)-30A [8.66] | (D)-1 [1.20] | (E)-1 [1.32] | (S)-1 [10] | (S)-2 [2577] |
| Comparative Example 32 | (A)-1 [100] | (B)-31A [8.57] | (D)-1 [1.20] | (E)-1 [1.32] | (S)-1 [10] | (S)-2 [2577] |
| Comparative Example 33 | (A)-1 [100] | (B)-32A [9.30] | (D)-1 [1.201 | (E)-1 [1.32] | (S)-1 [10] | (S)-2 [2577] |
| Comparative Example 34 | (A)-1 [100] | (B)-33A [10.83] | (D)-1 [1.20] | (E)-1 [1.32] | (S)-1 [10] | (S)-2 [2577] |

TABLE 21

| | Component (A) | Component (B) | Component (D) | Component (E) | Component (S) | |
|---|---|---|---|---|---|---|
| Comparative Example 35 | (A)-1 [100] | (B)-34A [9.16] | (D)-1 [1.20] | (E)-1 [1.32] | (S)-1 [10] | (S)-2 [2577] |
| Comparative Example 36 | (A)-1 [100] | (B)-35A [9.99] | (D)-1 [1.20] | (E)-1 [1.32] | (S)-1 [10] | (S)-2 [2577] |
| Comparative Example 37 | (A)-1 [100] | (B)-36A [9.41] | (D)-1 [1.20] | (E)-1 [1.32] | (S)-1 [10] | (S)-2 [2577] |
| Comparative Example 38 | (A)-1 [100] | (B)-37A [12.08] | (D)-1 [1.20] | (E)-1 [1.32] | (S)-1 [10] | (S)-2 [2577] |
| Comparative Example 39 | (A)-1 [100] | (B)-38A [11.88] | (D)-1 [1.20] | (E)-1 [1.32] | (S)-1 [10] | (S)-2 [2577] |
| Comparative Example 40 | (A)-1 [100] | (B)-39A [11.47] | (D)-1 [1.20] | (E)-1 [1.32] | (S)-1 [10] | (S)-2 [2577] |
| Comparative Example 41 | (A)-1 [100] | (B)-40A [11.66] | (D)-1 [1.20] | (E)-1 [1.32] | (S)-1 [10] | (S)-2 [2577] |
| Comparative Example 42 | (A)-1 [100] | (B)-41A [11.55] | (D)-1 [1.20] | (E)-1 [1.32] | (S)-1 [10] | (S)-2 [2577] |
| Comparative Example 43 | (A)-1 [100] | (B)-45A [12.83] | (D)-1 [1.20] | (E)-1 [1.32] | (S)-1 [10] | (S)-2 [2577] |
| Comparative Example 44 | (A)-1 [100] | (B)-42A [8.49] | (D)-1 [1.20] | (E)-1 [1.32] | (S)-1 [10] | (S)-2 [2577] |
| Comparative Example 45 | (A)-1 [100] | (B)-43A [8.85] | (D)-1 [1.20] | (E)-1 [1.32] | (S)-1 [10] | (S)-2 [2577] |
| Comparative Example 46 | (A)-2 [100] | (B)-1A [8.80] | (D)-1 [1.20] | (E)-1 [1.32] | (S)-1 [10] | (S)-2 [2577] |
| Comparative Example 47 | (A)-2 [100] | (B)-3A [11.36] | (D)-1 [1.20] | (E)-1 [1.32] | (S)-1 [10] | (S)-2 [2577] |

In Tables 16 to 21, the reference characters indicate the following. Further, the values in brackets [ ] indicate the amount (in terms of parts by weight) of the component added.

(A)-1: polymeric compound (A)-1 shown below (Mw=7,000, Mw/Mn=1.70, l/m/n=45/35/20 (molar ratio).

(A)-2: polymeric compound (A)-2 shown below (Mw=7,900, Mw/Mn=1.56, l/m/n/o/p=35/24/16/13/12 (molar ratio).

(B)-1 to (B)-45: compounds (B)-1 to (B)-45 shown below.

(B)-1A to (B)-45A: compounds in which anions in the compounds (B)-1 to (B)-45 have been replaced by an anion represented by following formula (B)-A.

Specific examples of the structure of the compound (B)-1A is shown below.

(B)-1B: compound (B)-1B shown below (D)-1: tri-n-pentylamine (D)-2: compound (D)-2 shown below (D)-3: compound (D)-3 shown below (D)-4: compound (D)-4 shown below (D)-5: compound (D)-5 shown below (E)-1: salicylic acid (S)-1: γ-butyrolactone (S)-2: a mixed solvent of PGMEA/PGME/cyclohexanone=45/35/20 (weight ratio)

[Chemical Formula 78]

(A)-1

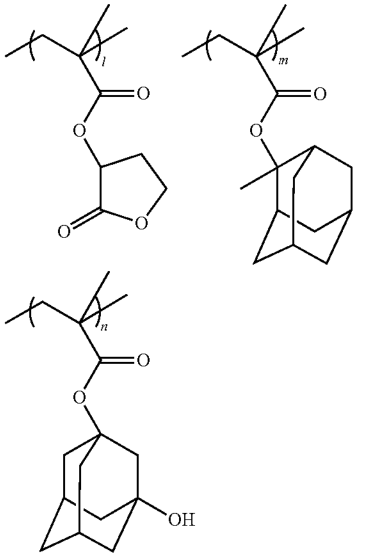

(A)-2

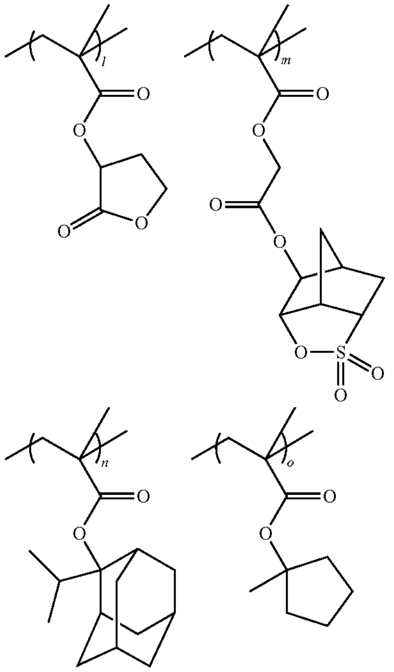

-continued

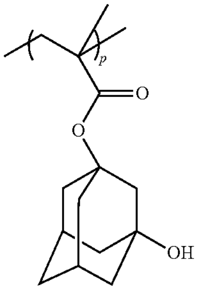

(B)-A

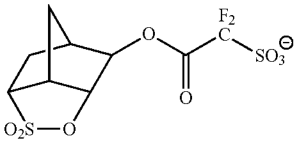

(B)-1A

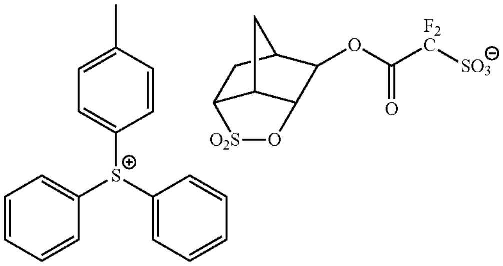

(B)-1B

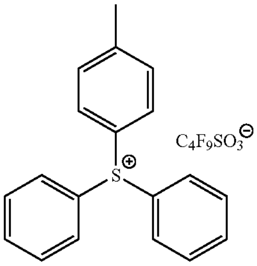

[Chemical Formula 79]

(D)-2

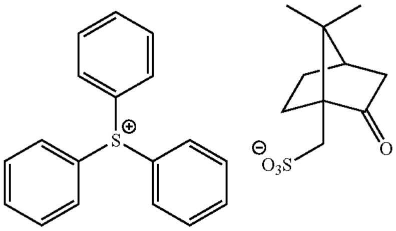

(D)-3

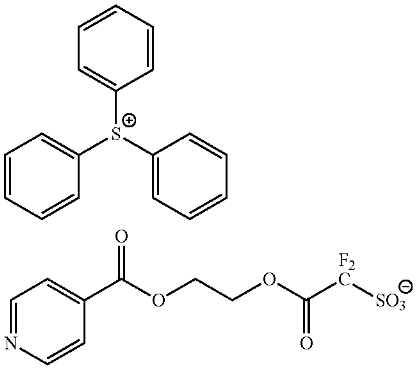

-continued (D)-4

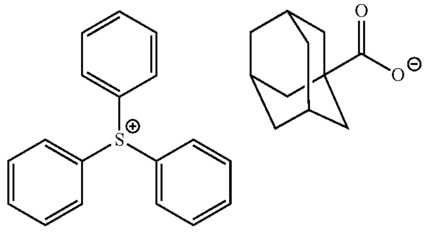

(D)-5

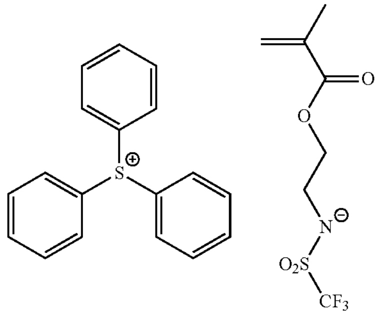

Using the obtained positive resist compositions, resist patterns were formed in the following manner, and the following evaluations were conducted.

[Formation of Resist Pattern]

An organic anti-reflection film composition (product name: ARC29A, manufactured by Brewer Science Ltd.) was applied to an 8-inch silicon wafer using a spinner, and the composition was then baked on a hot plate at 205° C. for 60 seconds, thereby forming an organic anti-reflection film having a film thickness of 82 nm.

Then, each positive resist composition obtained in the examples was applied to the organic anti-reflection film using a spinner, and was then prebaked (PAB) on a hotplate at a temperature indicated in Tables 22 to 25 for 60 seconds and dried, thereby forming a resist film having a film thickness of 150 nm.

Subsequently, the resist film was selectively irradiated with an ArF excimer laser (193 nm) through a mask pattern, using an ArF exposure apparatus NSR-S302A (manufactured by Nikon Corporation, NA (numerical aperture)=0.60, 2/3 annular illumination).

Next, a PEB treatment was conducted at a temperature indicated in Tables 20 to 23 for 60 seconds, followed by alkali development for 30 seconds at 23° C. in a 2.38% by weight aqueous tetramethylammonium hydroxide (TMAH) solution. Then, the resist was washed for 15 seconds with pure water, followed by drying by shaking.

As a result, in each of the examples, a 1:1 line and space pattern (LS pattern) having a line width of 120 nm and a pitch of 240 nm was formed.

The optimum exposure dose Eop (mJ/cm$^2$; sensitivity) with which the LS pattern was formed was determined. The results are shown in Tables 22 to 25.

[Evaluation of Line Width Roughness (LWR)]

With respect to each of the 1:1 LS patterns formed with the above optimum exposure dose Eop and having a space width of 120 nm and a pitch of 240 nm, the space width at 400 points in the lengthwise direction of the space were measured using a measuring scanning electron microscope (SEM) (product name: S-9380, manufactured by Hitachi High-Technologies Corporation; acceleration voltage: 300V). From the results, the value of 3 times the standard deviation s (i.e., 3s) was determined, and the average of the 3s values at 400 points was calculated as a yardstick of LWR. The results are shown in Tables 22 to 25.

The smaller this 3s value is, the lower the level of roughness of the line width, indicating that a LS pattern with a uniform width was obtained.

[Evaluation of Exposure Latitude (EL Margin)]

With respect to the above optimum exposure dose Eop, the exposure dose with which an LS pattern having a dimension of the target dimension ±5% was determined, and the EL margin (unit: %) was determined by the following formula. The results are shown in Tables 22 to 25.

$$EL\ \text{margin}\ (\%)=(|E1-E2|/Eop)\times 100$$

In the formula, E1 represents the exposure dose (mJ/cm$^2$) for forming an LS pattern having a119 line width of 114 nm, and E2 represents the exposure dose (mJ/cm$^2$) for forming an LS pattern having a line width of 126 nm.

The larger the value of the "EL margin", the smaller the change in the pattern size by the variation of the exposure dose.

[Evaluation of Mask Error Factor (MEF)]

In the same manner as described above, with the above Eop, LS patterns were formed using a mask pattern targeting a space width of 120 nm and a pitch of 260 nm, and a mask pattern targeting a space width of 130 nm and a pitch of 260 nm, and the MEF value was calculated by the following formula.

$$MEF=|CD_{130}-CD_{120}|/|MD_{130}-MD_{120}|$$

In the formula, $CD_{130}$ and $CD_{120}$ represent the respective line widths (nm) of the actual LS patterns respectively formed using the mask pattern targeting a line width of 130 nm and the mask pattern targeting a line width of 120 nm. $MD_{130}$ and $MD_{120}$ represent the respective target line widths (nm), meaning $MD_{130}$=130, and $MD_{120}$=120.

A MEF value closer to 1 indicates that a resist pattern faithful to the mask pattern was formed. The results are shown in Tables 22 to 25.

[Evaluation of Pattern Shape]

With respect to each 1:1 LS pattern formed with the above optimum exposure dose Eop, the cross-sectional shape was observed using a scanning electron microscope (product name: SU-8000, manufactured by Hitachi High-Technologies Corporation), and the cross-sectional shape was evaluated with the following criteria. The results are shown in Tables 22 to 25.

A: Extremely high rectangularity and particularly good shape

B: moderate rectangularity

C: Top-rounded shape, and low rectangularity

TABLE 22

| | PAB (° C.) | PEB (° C.) | Eop (mJ/cm$^2$) | LWR (nm) | EL (%) | MEF | Shape |
|---|---|---|---|---|---|---|---|
| Example 1 | 110 | 110 | 43.8 | 12.5 | 7.34 | 2.30 | A |
| Example 2 | 110 | 110 | 59.8 | 7.6 | 9.20 | 2.52 | A |
| Example 3 | 110 | 110 | 59.4 | 7.5 | 9.21 | 2.53 | A |
| Example 4 | 110 | 110 | 55.1 | 7.6 | 9.71 | 2.52 | A |
| Example 5 | 110 | 110 | 58.6 | 8.1 | 9.18 | 2.61 | A |
| Example 6 | 110 | 110 | 59.4 | 7.7 | 8.98 | 2.61 | A |
| Example 7 | 110 | 110 | 57.4 | 7.3 | 9.75 | 2.61 | A |
| Example 8 | 110 | 110 | 70.8 | 8.5 | 9.73 | 2.79 | A |
| Example 9 | 110 | 110 | 52.4 | 9.2 | 8.01 | 2.78 | A |
| Example 10 | 110 | 110 | 54.0 | 8.7 | 7.79 | 3.04 | A |
| Example 11 | 110 | 110 | 65.9 | 7.5 | 9.98 | 3.04 | A |
| Example 12 | 110 | 110 | 57.4 | 7.5 | 9.31 | 2.53 | A |

TABLE 22-continued

| | PAB (° C.) | PEB (° C.) | Eop (mJ/cm$^2$) | LWR (nm) | EL (%) | MEF | Shape |
|---|---|---|---|---|---|---|---|
| Example 13 | 110 | 110 | 55.0 | 7.5 | 10.20 | 2.51 | A |
| Example 14 | 110 | 110 | 53.6 | 7.9 | 9.07 | 2.51 | A |
| Example 15 | 110 | 110 | 55.0 | 7.9 | 9.01 | 2.51 | A |
| Example 16 | 110 | 110 | 51.1 | 7.3 | 10.55 | 2.51 | A |
| Example 27 | 110 | 110 | 57.4 | 7.5 | 11.17 | 2.49 | A |
| Example 18 | 110 | 110 | 48.7 | 7.9 | 8.94 | 2.52 | A |
| Example 19 | 110 | 110 | 57.4 | 7.9 | 9.73 | 2.52 | A |
| Example 20 | 110 | 110 | 67.5 | 7.6 | 10.92 | 2.52 | A |
| Example 21 | 110 | 110 | 64.9 | 7.4 | 9.10 | 2.82 | A |
| Example 22 | 110 | 110 | 83.1 | 7.3 | 9.98 | 2.53 | A |
| Example 23 | 110 | 110 | 95.3 | 8.3 | 11.20 | 2.61 | A |

TABLE 23

| | PAB (° C.) | PEB (° C.) | Eop (mJ/cm2) | LWR (nm) | EL (%) | MEF | Shape |
|---|---|---|---|---|---|---|---|
| Example 24 | 110 | 110 | 71.5 | 8.2 | 10.25 | 2.52 | A |
| Example 25 | 110 | 110 | 76.7 | 8.0 | 10.00 | 2.53 | A |
| Example 26 | 110 | 110 | 72.0 | 7.5 | 9.61 | 2.55 | A |
| Example 27 | 110 | 110 | 53.3 | 7.9 | 10.92 | 3.04 | A |
| Example 28 | 110 | 110 | 80.6 | 8.4 | 9.40 | 2.52 | A |
| Example 29 | 110 | 110 | 57.7 | 7.5 | 10.84 | 2.45 | A |
| Example 30 | 110 | 110 | 65.2 | 7.5 | 10.61 | 2.55 | A |
| Example 31 | 110 | 110 | 76.7 | 7.9 | 9.01 | 2.51 | A |
| Example 32 | 110 | 110 | 50.1 | 7.3 | 10.83 | 2.53 | A |
| Example 33 | 110 | 110 | 55.0 | 7.9 | 11.74 | 2.48 | A |
| Example 34 | 110 | 110 | 50.1 | 8.7 | 8.88 | 2.78 | A |
| Example 35 | 110 | 110 | 59.8 | 8.3 | 11.17 | 2.78 | A |
| Example 36 | 110 | 110 | 54.9 | 7.9 | 9.06 | 2.52 | A |
| Example 37 | 110 | 110 | 60.1 | 7.5 | 11.29 | 2.48 | A |
| Example 38 | 110 | 110 | 65.7 | 7.3 | 10.76 | 2.61 | A |
| Example 39 | 110 | 110 | 56.2 | 7.9 | 9.31 | 2.55 | A |
| Example 40 | 110 | 110 | 64.8 | 7.5 | 10.54 | 2.56 | A |
| Example 41 | 110 | 110 | 56.7 | 8.2 | 10.20 | 2.56 | A |
| Example 42 | 110 | 110 | 58.7 | 7.2 | 10.11 | 2.85 | A |
| Example 43 | 110 | 110 | 43.0 | 8.8 | 9.07 | 2.56 | A |
| Example 44 | 110 | 110 | 47.2 | 7.8 | 8.88 | 2.61 | A |
| Example 45 | 90 | 90 | 42.7 | 12.0 | 7.43 | 2.15 | A |
| Example 46 | 90 | 90 | 57.9 | 7.1 | 9.32 | 2.37 | A |
| Example 47 | 110 | 110 | 37.9 | 12.5 | 6.86 | 2.21 | A |
| Example 48 | 110 | 110 | 42.9 | 12.2 | 6.81 | 2.27 | A |
| Example 49 | 110 | 110 | 40.0 | 12.5 | 7.03 | 2.27 | A |
| Example 50 | 110 | 110 | 38.2 | 12.1 | 6.60 | 2.25 | A |
| Example 51 | 110 | 110 | 43.2 | 12.4 | 7.26 | 2.14 | A |

TABLE 24

| | PAB (° C.) | PEB (° C.) | Eop (mJ/cm$^2$) | LWR (nm) | EL (%) | MEF | Shape |
|---|---|---|---|---|---|---|---|
| Comparative Example 1 | 110 | 110 | 41.4 | 13.3 | 7.00 | 2.68 | B |
| Comparative Example 2 | 110 | 110 | 27.2 | 15.5 | 6.24 | 2.40 | C |
| Comparative Example 3 | 110 | 110 | 56.6 | 9.5 | 7.63 | 3.45 | B |
| Comparative Example 4 | 110 | 110 | 56.1 | 9.3 | 7.64 | 3.47 | B |
| Comparative Example 5 | 110 | 110 | 52.1 | 9.5 | 8.05 | 3.45 | B |
| Comparative Example 6 | 110 | 110 | 55.4 | 10.1 | 7.61 | 3.58 | B |
| Comparative Example 7 | 110 | 110 | 56.1 | 9.6 | 7.45 | 3.58 | B |
| Comparative Example 8 | 110 | 110 | 54.3 | 9.1 | 8.08 | 3.58 | B |
| Comparative Example 9 | 110 | 110 | 66.9 | 10.6 | 8.07 | 3.83 | B |
| Comparative Example 10 | 110 | 110 | 49.6 | 11.5 | 6.64 | 3.81 | B |

TABLE 24-continued

| | PAB (° C.) | PEB (° C.) | Eop (mJ/cm$^2$) | LWR (nm) | EL (%) | MEF | Shape |
|---|---|---|---|---|---|---|---|
| Comparative Example 11 | 110 | 110 | 51.1 | 10.9 | 6.46 | 4.17 | B |
| Comparative Example 12 | 110 | 110 | 62.3 | 9.3 | 8.28 | 4.17 | B |
| Comparative Example 13 | 110 | 110 | 54.3 | 9.3 | 7.72 | 3.47 | B |
| Comparative Example 14 | 110 | 110 | 52.0 | 9.4 | 8.46 | 3.44 | B |
| Comparative Example 15 | 110 | 110 | 50.7 | 9.8 | 7.52 | 3.44 | B |
| Comparative Example 16 | 110 | 110 | 52.0 | 9.8 | 7.47 | 3.44 | B |
| Comparative Example 17 | 110 | 110 | 48.3 | 9.7 | 8.75 | 3.44 | B |
| Comparative Example 18 | 110 | 110 | 54.3 | 9.4 | 9.26 | 3.42 | B |
| Comparative Example 19 | 110 | 110 | 46.0 | 9.9 | 7.41 | 3.45 | B |
| Comparative Example 20 | 110 | 110 | 54.3 | 9.9 | 8.07 | 3.45 | B |
| Comparative Example 21 | 110 | 110 | 63.8 | 9.5 | 9.06 | 3.45 | B |
| Comparative Example 22 | 110 | 110 | 61.4 | 9.2 | 7.55 | 3.87 | B |
| Comparative Example 23 | 110 | 110 | 78.6 | 9.1 | 8.28 | 3.47 | B |

TABLE 25

| | PAB (° C.) | PEB (° C.) | Eop (mJ/cm2) | LWR (nm) | EL (%) | MEF | Shape |
|---|---|---|---|---|---|---|---|
| Comparative Example 24 | 110 | 110 | 90.1 | 10.3 | 9.29 | 3.58 | B |
| Comparative Example 25 | 110 | 110 | 67.6 | 10.2 | 8.50 | 3.45 | B |
| Comparative Example 26 | 110 | 110 | 72.5 | 10.0 | 8.29 | 3.47 | B |
| Comparative Example 27 | 110 | 110 | 68.0 | 9.3 | 7.97 | 3.49 | B |
| Comparative Example 28 | 110 | 110 | 50.4 | 9.9 | 9.06 | 4.17 | B |
| Comparative Example 29 | 110 | 110 | 57.2 | 10.5 | 7.79 | 3.45 | B |
| Comparative Example 30 | 110 | 110 | 54.5 | 9.4 | 8.99 | 3.36 | B |
| Comparative Example 31 | 110 | 110 | 61.6 | 9.3 | 8.80 | 3.49 | B |
| Comparative Example 32 | 110 | 110 | 72.5 | 9.9 | 7.47 | 3.44 | B |
| Comparative Example 33 | 110 | 110 | 47.4 | 9.1 | 8.98 | 3.47 | B |
| Comparative Example 34 | 110 | 110 | 52.0 | 9.9 | 9.74 | 3.40 | B |
| Comparative Example 35 | 110 | 110 | 47.4 | 10.9 | 7.37 | 3.81 | B |
| Comparative Example 36 | 110 | 110 | 56.6 | 10.3 | 9.26 | 3.81 | B |
| Comparative Example 37 | 110 | 110 | 51.9 | 9.9 | 7.51 | 3.45 | B |
| Comparative Example 38 | 110 | 110 | 56.8 | 9.4 | 9.36 | 3.40 | B |
| Comparative Example 39 | 110 | 110 | 62.1 | 9.1 | 8.92 | 3.58 | B |
| Comparative Example 40 | 110 | 110 | 53.1 | 9.8 | 7.72 | 3.49 | B |
| Comparative Example 41 | 110 | 110 | 61.3 | 9.3 | 8.74 | 3.51 | B |
| Comparative Example 42 | 110 | 110 | 53.6 | 10.2 | 8.46 | 3.51 | B |
| Comparative Example 43 | 110 | 110 | 55.5 | 9.0 | 8.38 | 3.90 | B |
| Comparative Example 44 | 110 | 110 | 40.6 | 11.0 | 7.52 | 3.51 | B |

TABLE 25-continued

| | PAB (° C.) | PEB (° C.) | Eop (mJ/cm2) | LWR (nm) | EL (%) | MEF | Shape |
|---|---|---|---|---|---|---|---|
| Comparative Example 45 | 110 | 110 | 44.6 | 9.7 | 7.37 | 3.58 | B |
| Comparative Example 46 | 90 | 90 | 40.4 | 12.7 | 7.08 | 2.51 | B |
| Comparative Example 47 | 90 | 90 | 54.7 | 8.9 | 7.73 | 3.33 | B |

From the results shown in Tables 22 to 25, it was confirmed that the resist compositions of Examples 1 to 51 exhibited excellent lithography properties such as LWR, EL margin and MEF and excellent pattern shape as compared to the resist compositions of Comparative Examples 1 to 47.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition comprising a base component (A) which exhibits changed solubility in a developing solution under action of acid and an acid-generator component (B) which generates acid upon exposure, the acid-generator component (B) comprising an acid generator (B1) composed of a compound represented by the general formula shown below:

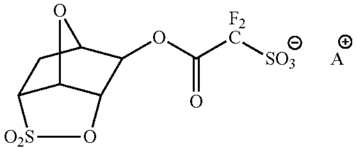

wherein, $A^+$ represents an organic cation.

2. The resist composition according to claim 1, wherein the base component (A) is a base component (A0) which exhibits increased polarity under action of acid.

3. A method of forming a resist pattern, comprising: forming a resist film using the resist composition of claim 1 or 2; conducting exposure of the resist film; and developing the resist film to form a resist pattern.

4. A compound represented by the general formula shown below:

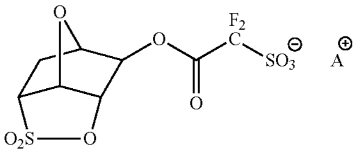

wherein, $A^+$ represents an organic cation.

5. An acid generator comprising the compound of claim 4.

6. The resist composition according to claim 1, wherein the acid generator (B 1) is at least one compound selected from the group consisting of the compounds represented by general formulas shown below:

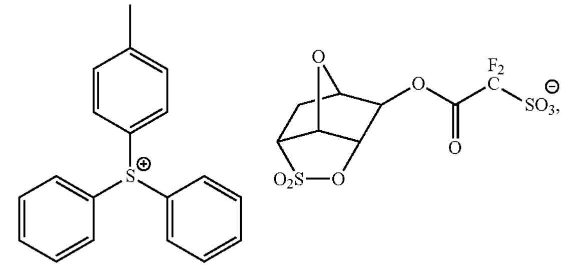

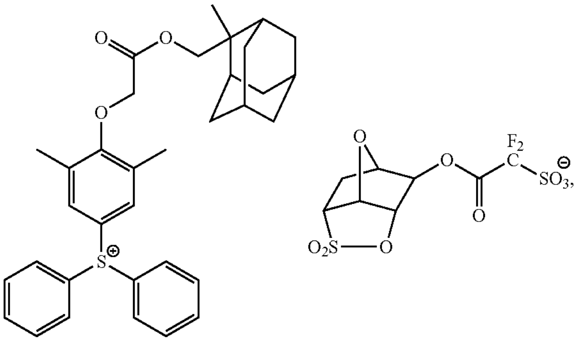

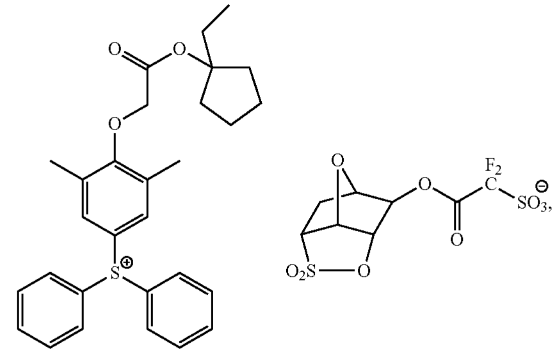

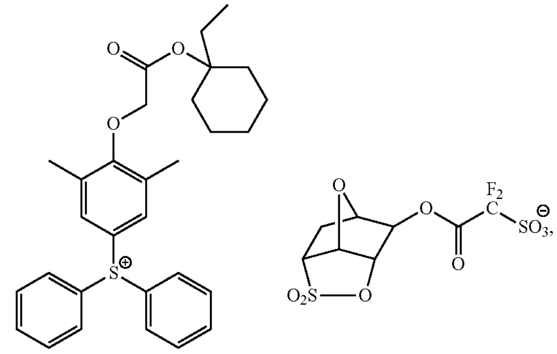

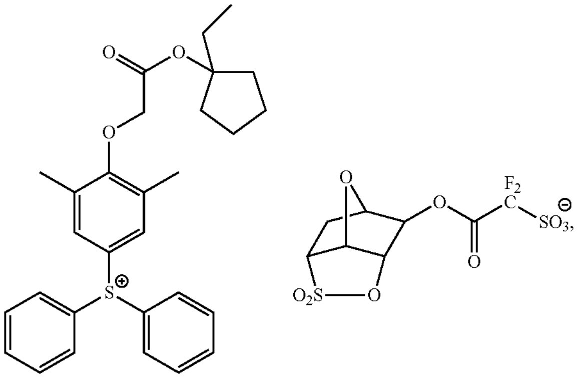

-continued
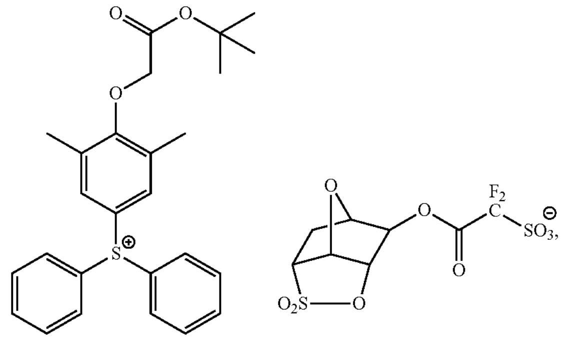
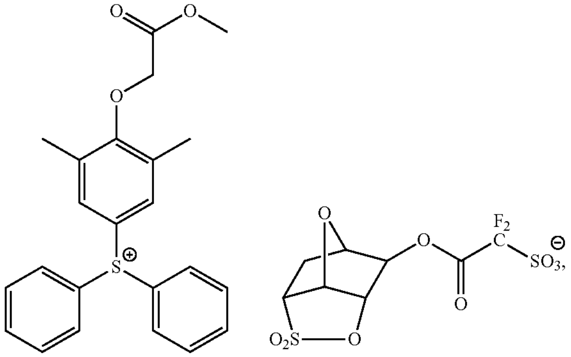
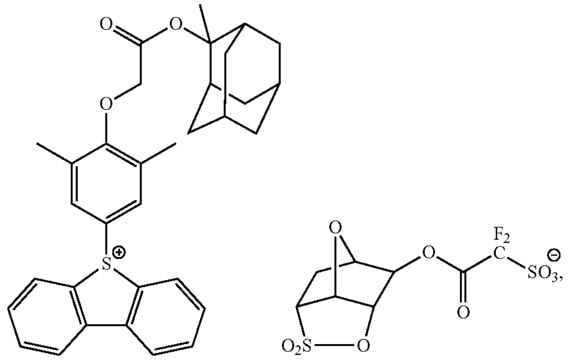
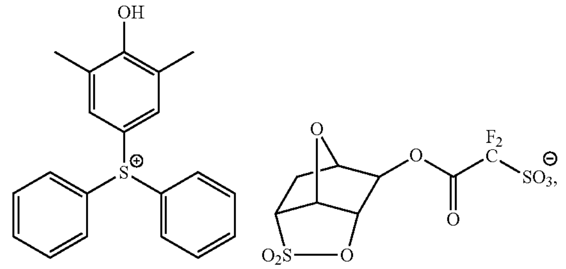
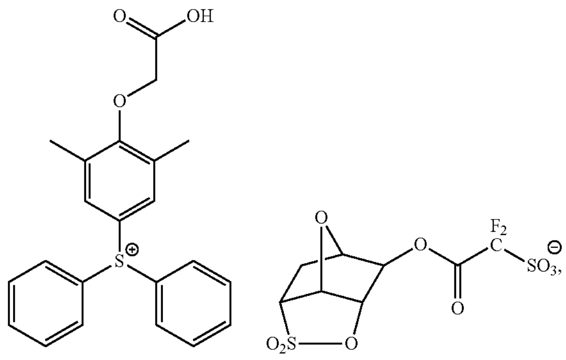
-continued
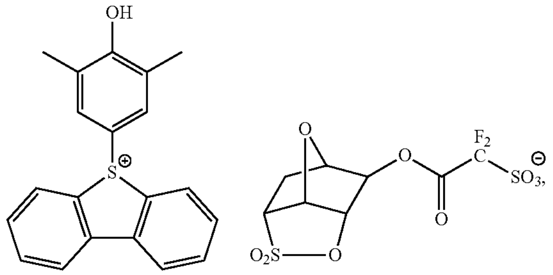
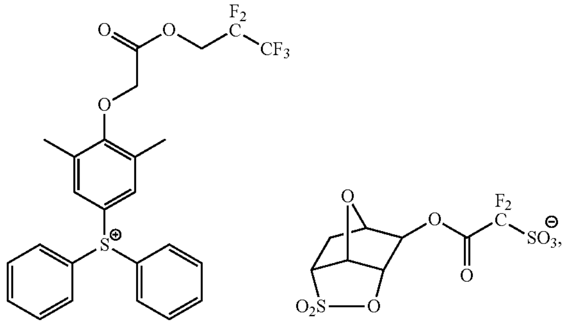
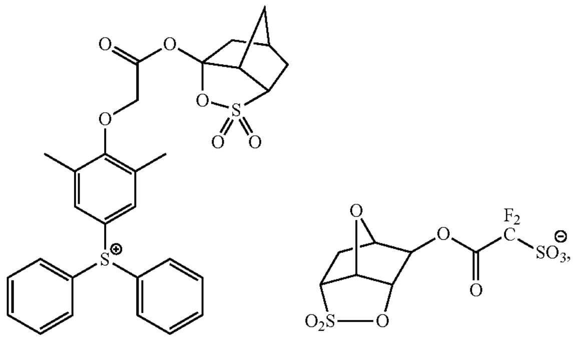
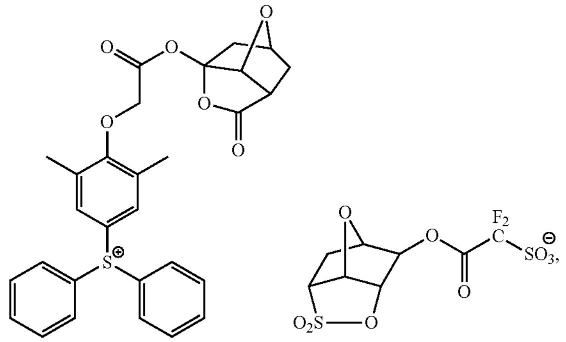
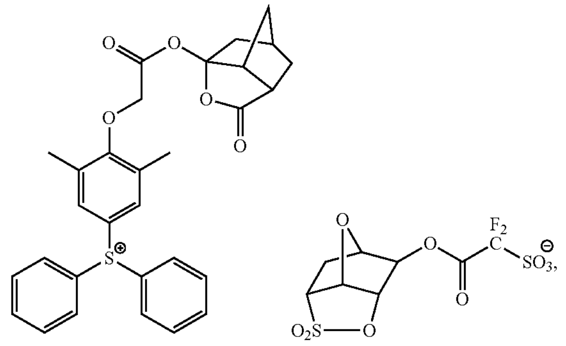

-continued
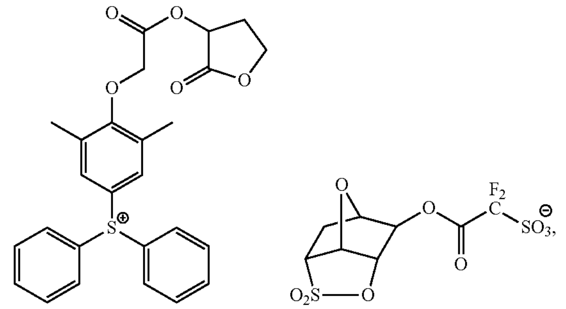
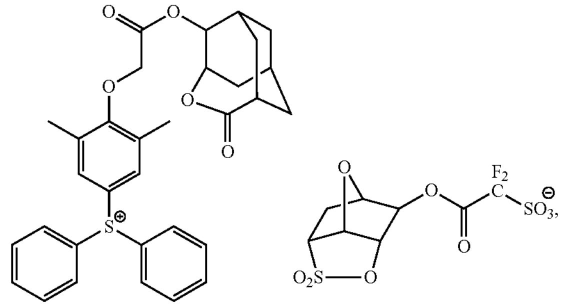
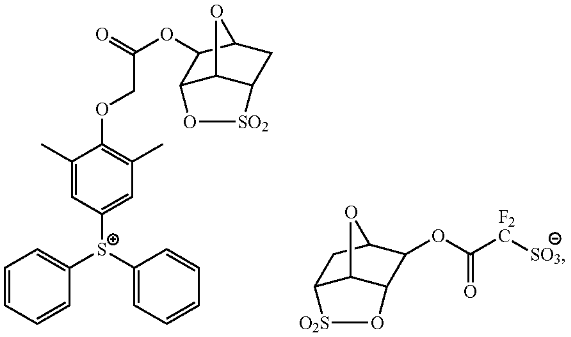
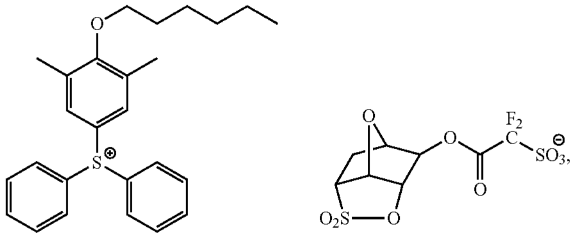
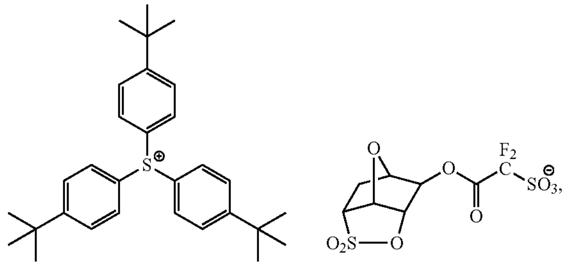
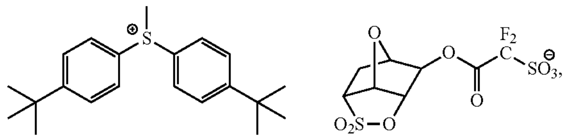
-continued
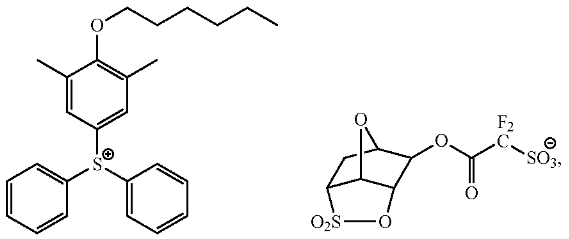
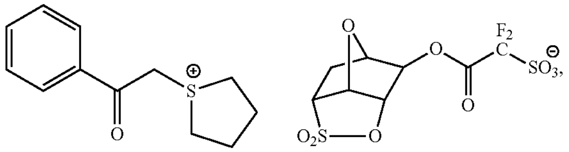
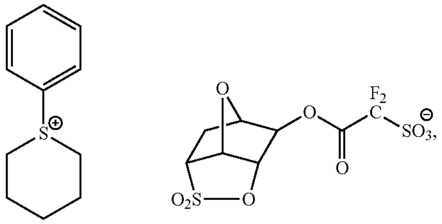
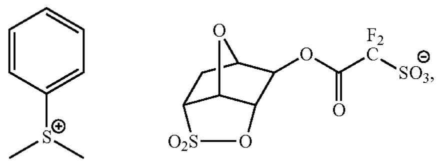
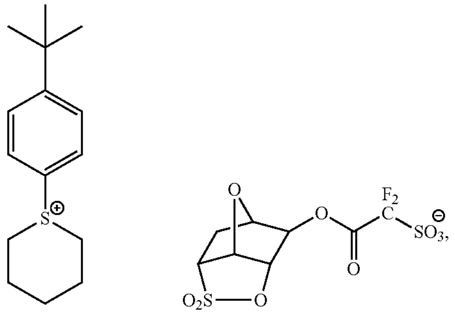
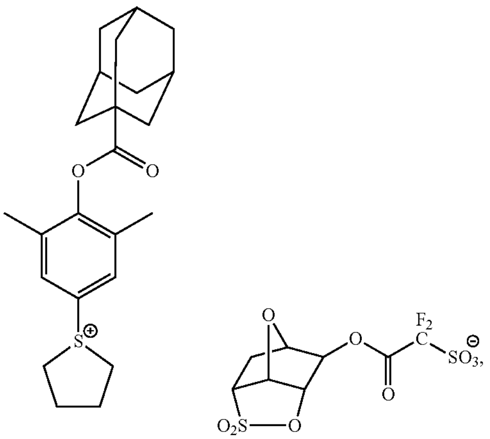

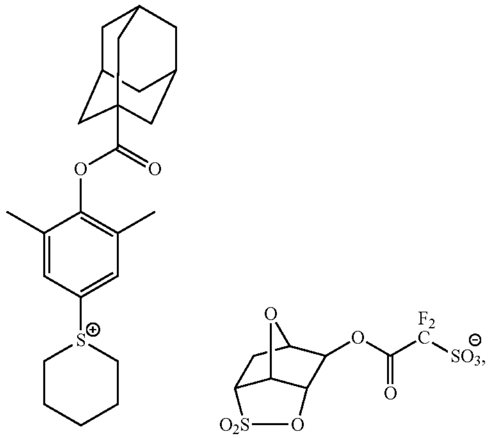
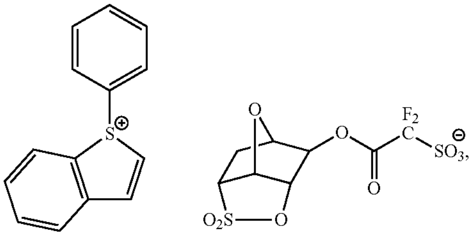
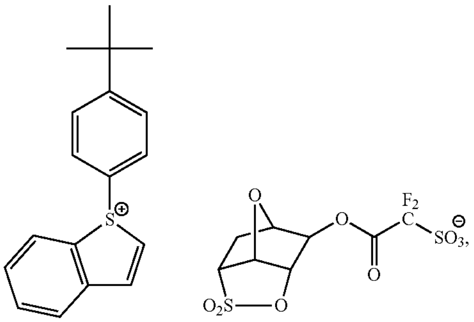
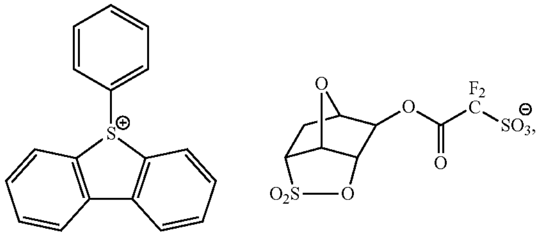
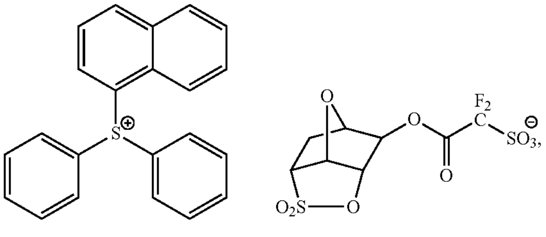
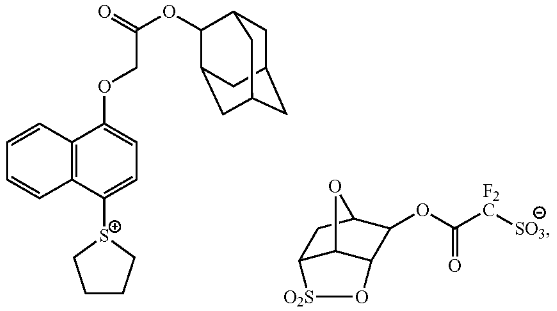
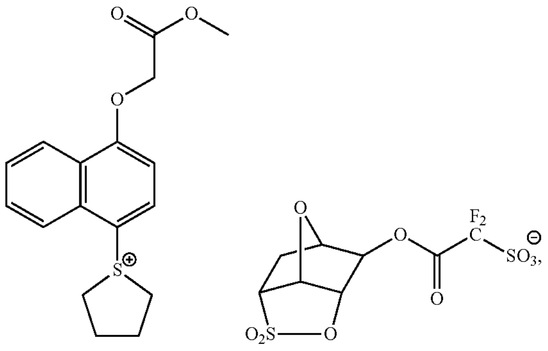
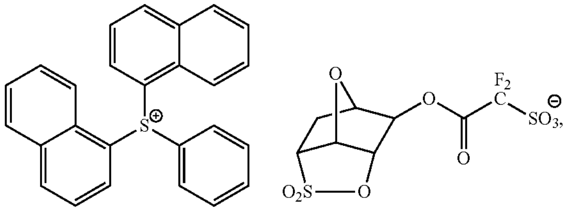
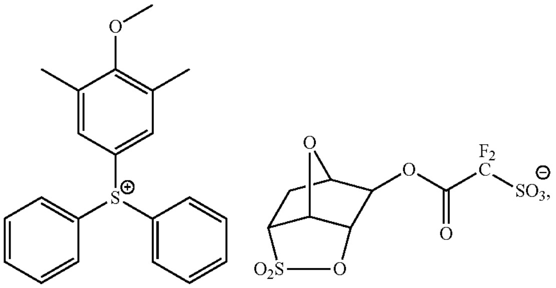
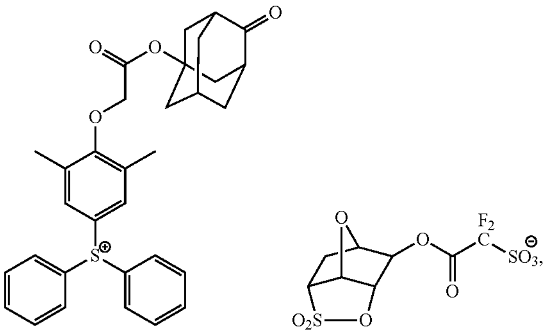

-continued
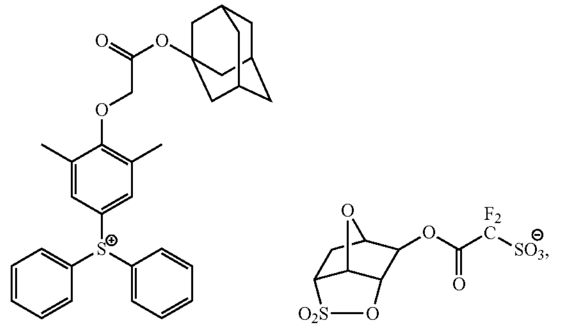
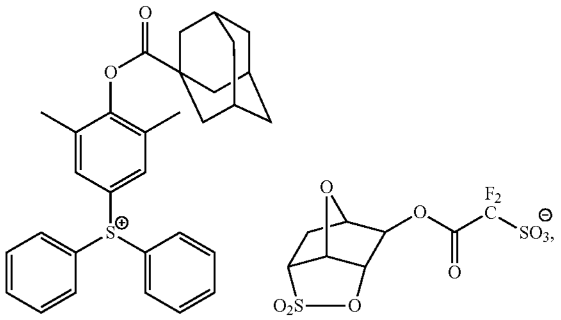
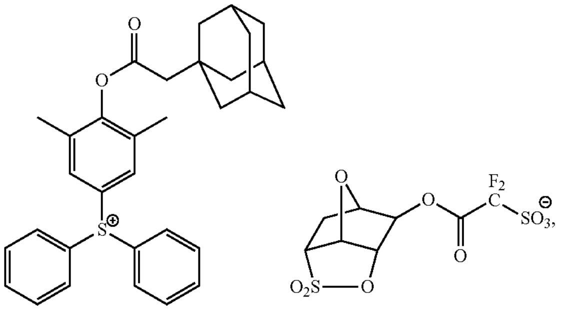
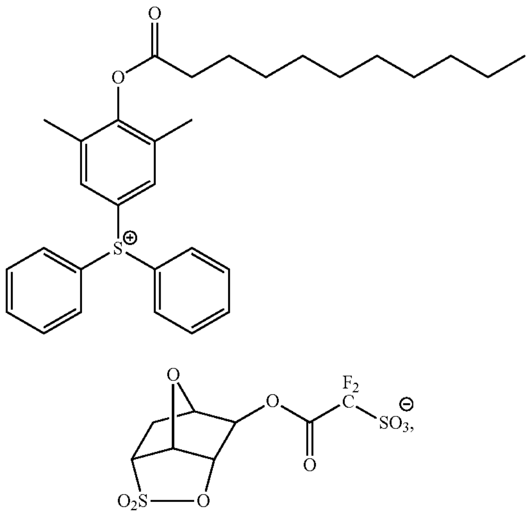
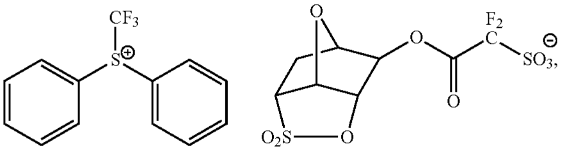
-continued
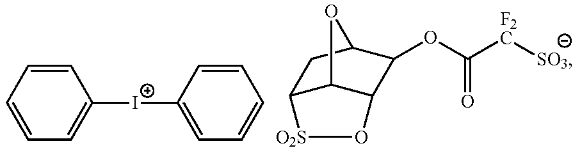
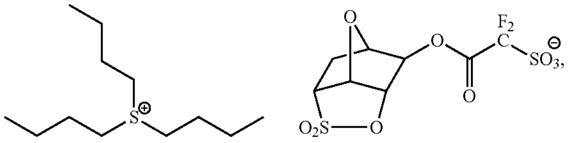
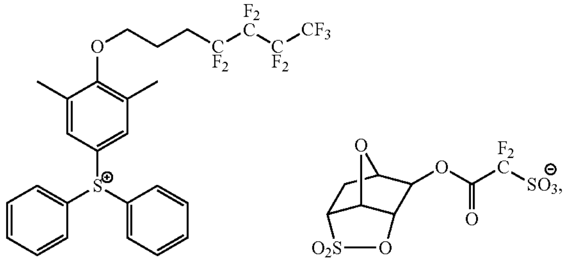
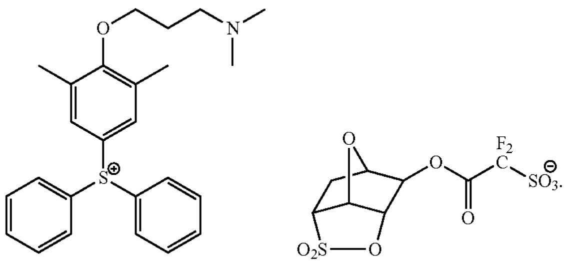
7. The compound according to claim 4, wherein the compound is at least one compound selected from the group consisting of the compounds represented by general formulas shown below:
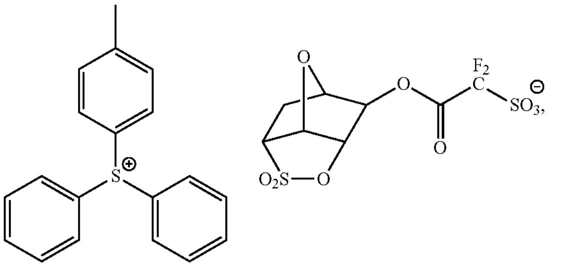
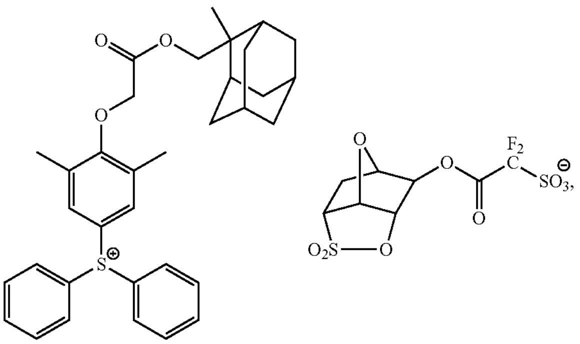

-continued
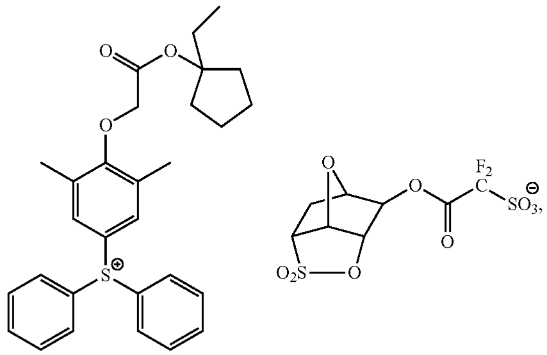
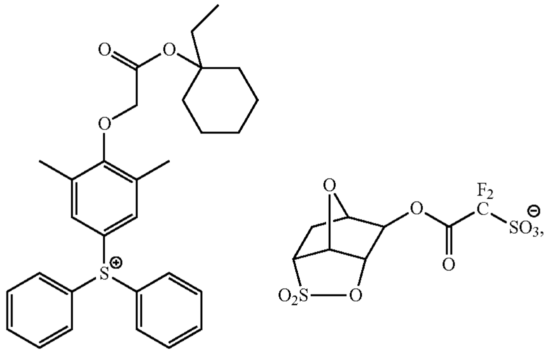
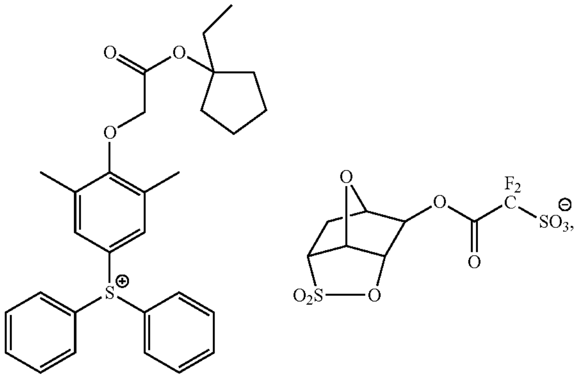
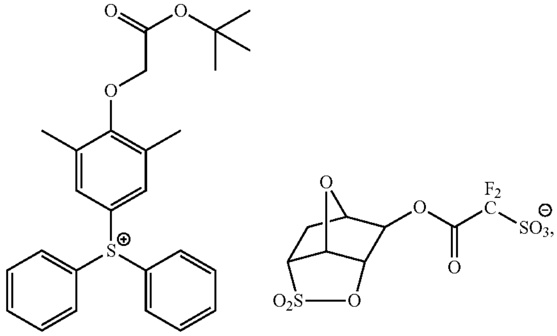
-continued
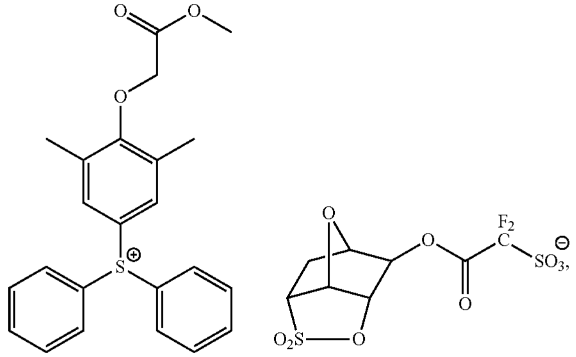
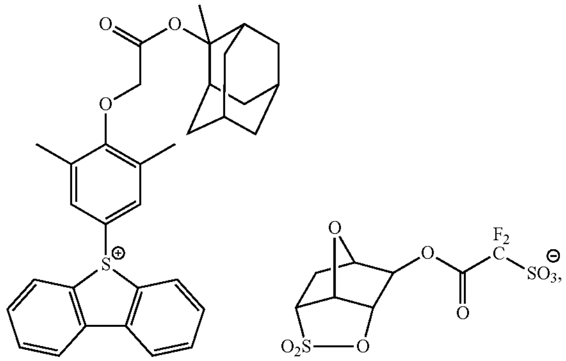
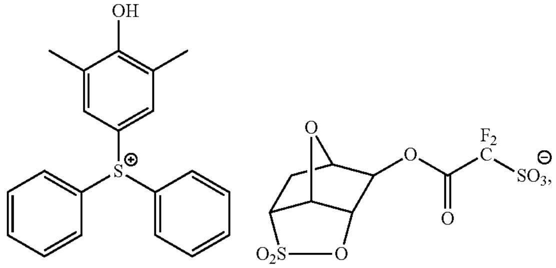
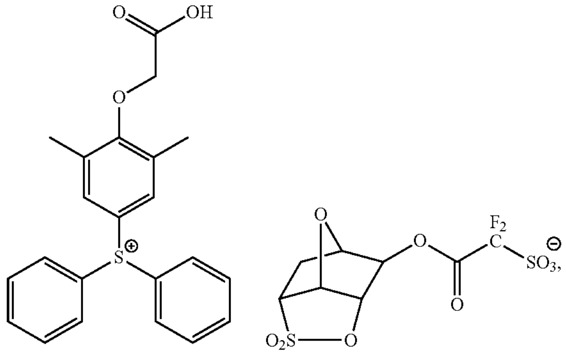
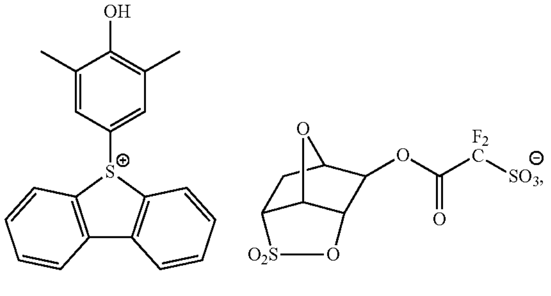

-continued
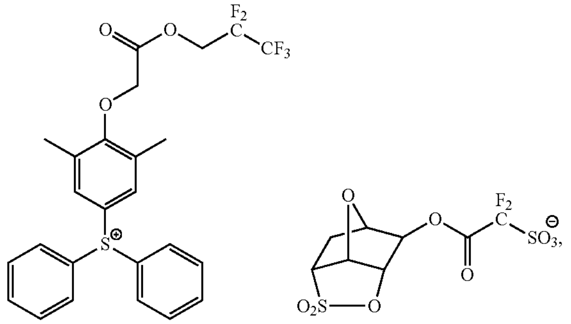
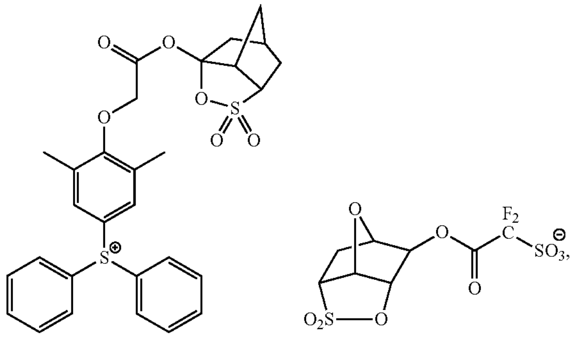
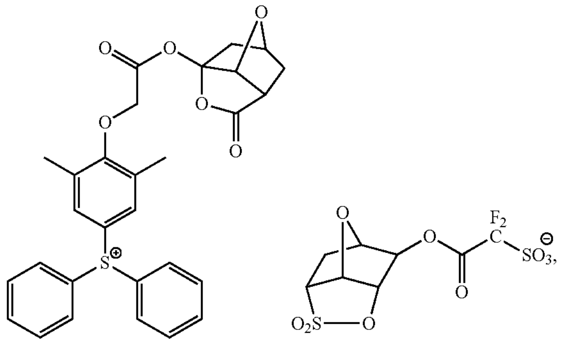
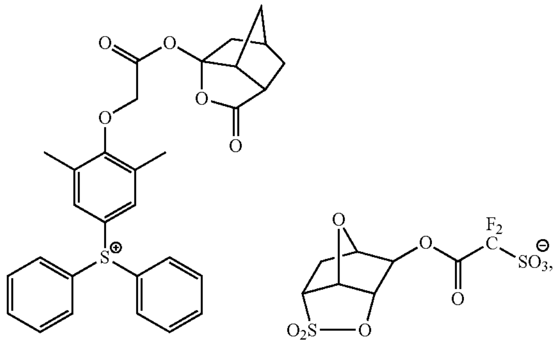
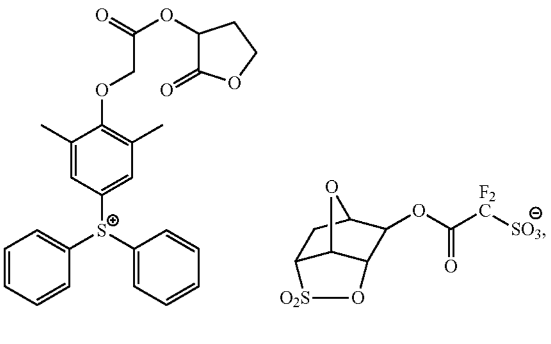
-continued
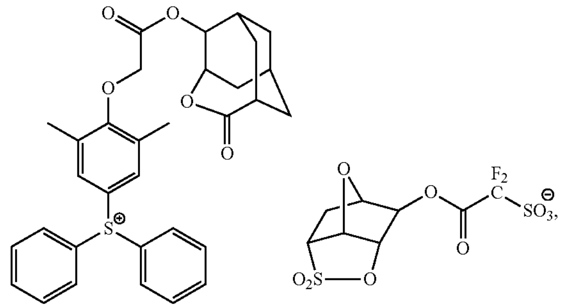
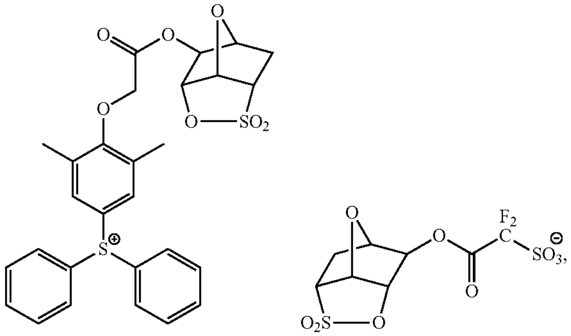
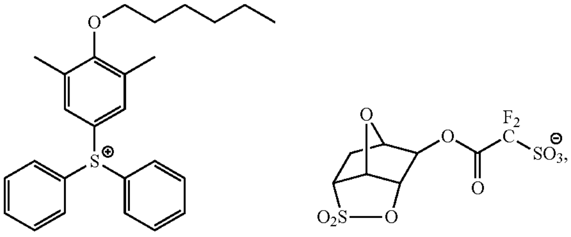
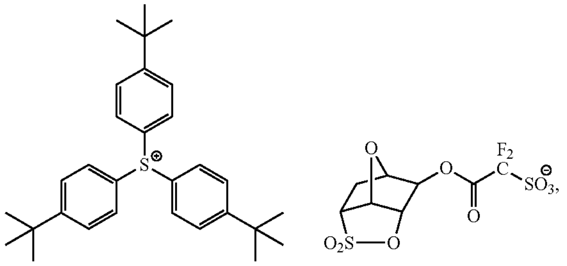
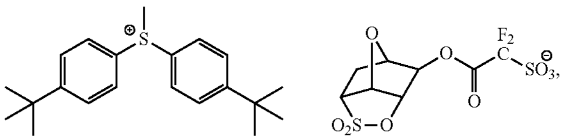
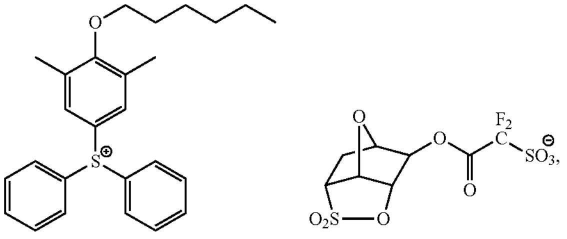
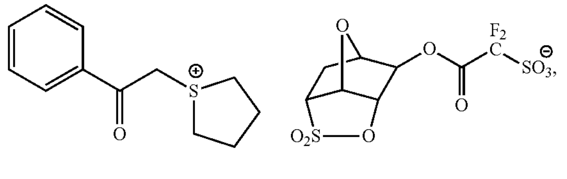

-continued
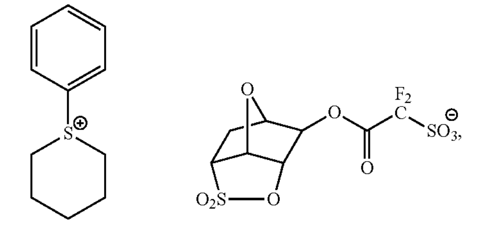
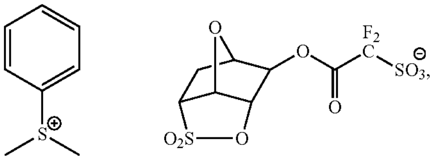
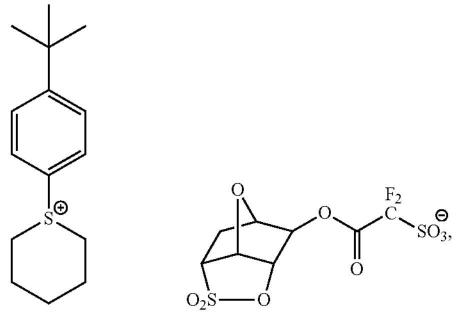
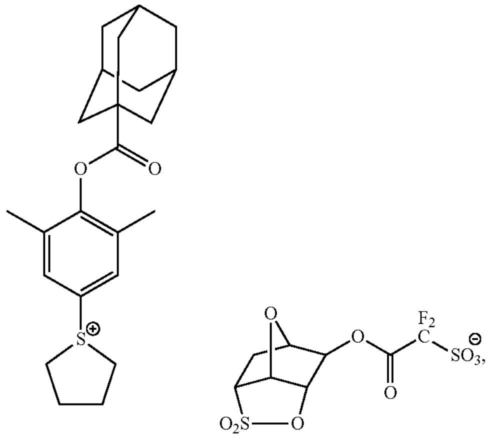
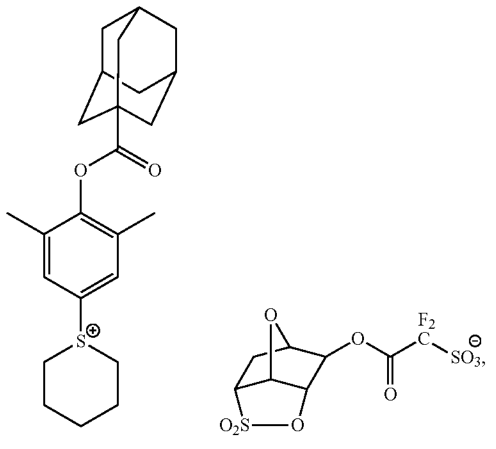
-continued
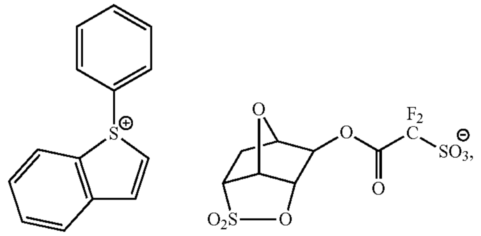
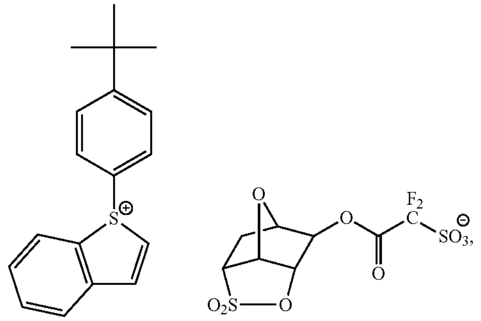
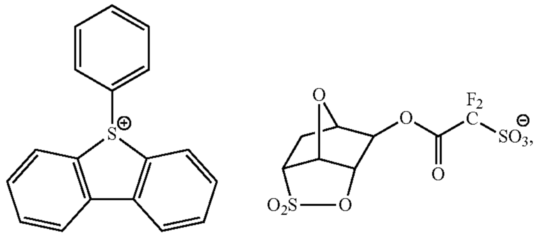
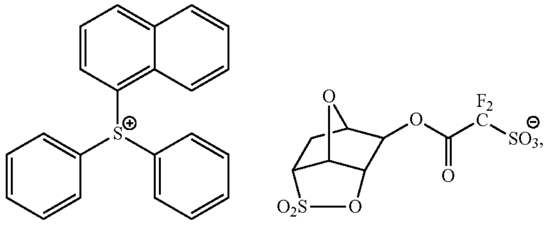
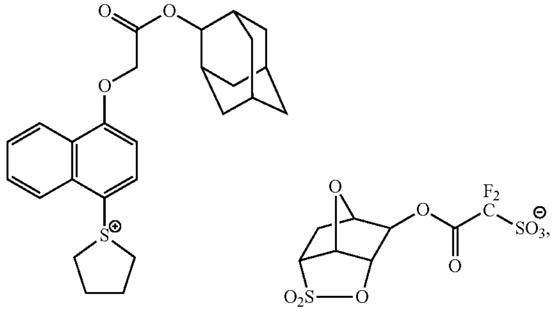
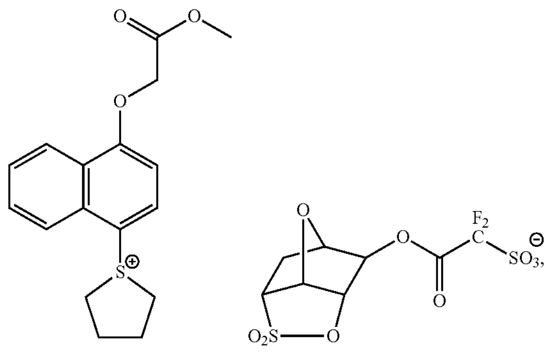

-continued
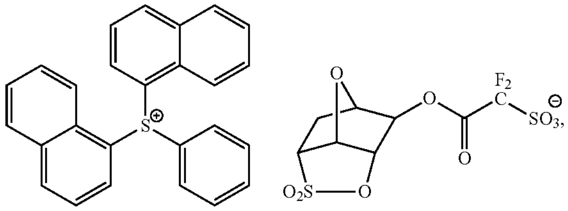
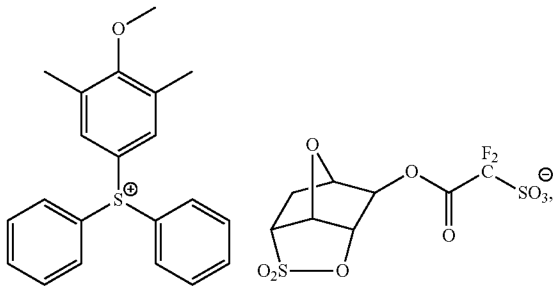
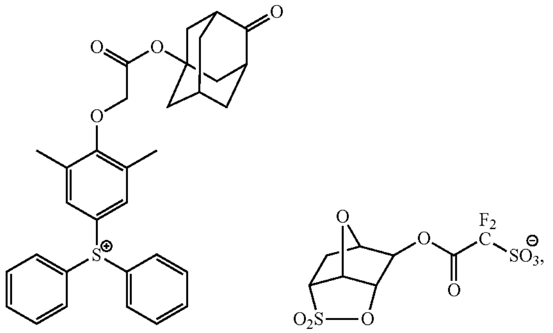
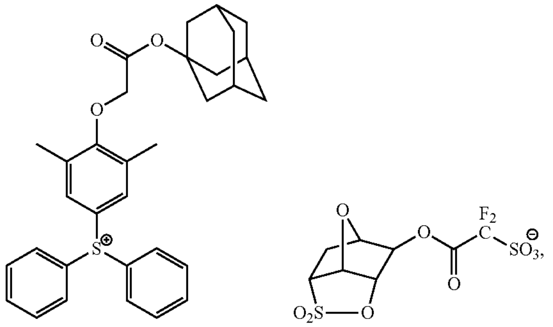
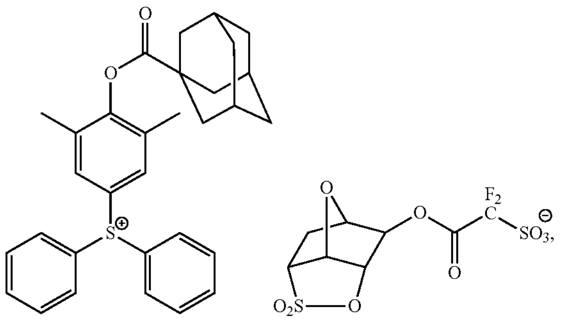
-continued
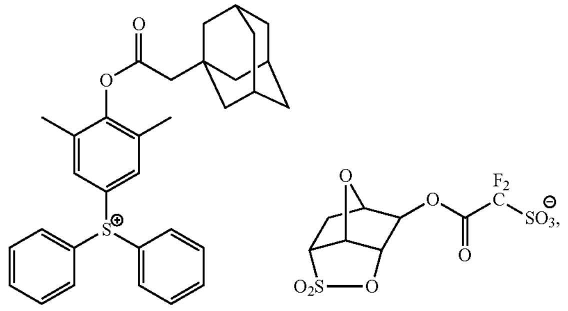
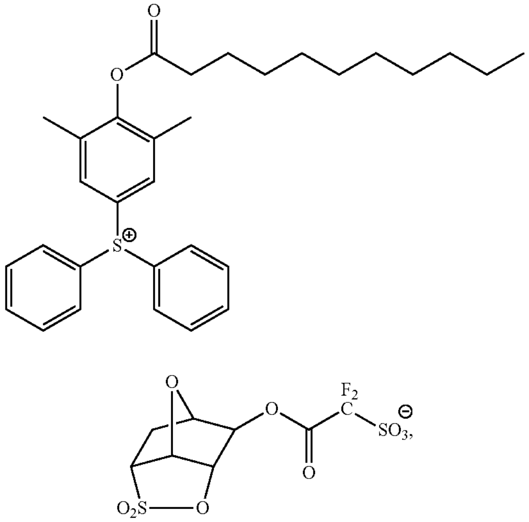
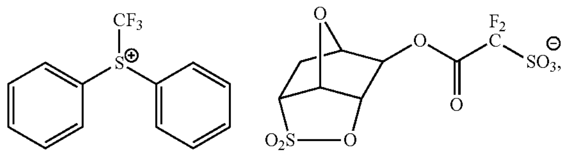
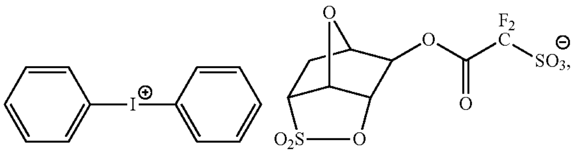
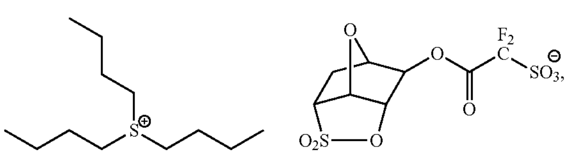
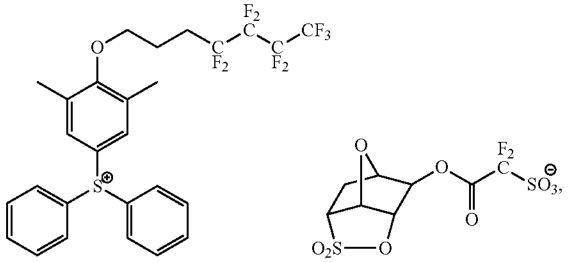

-continued
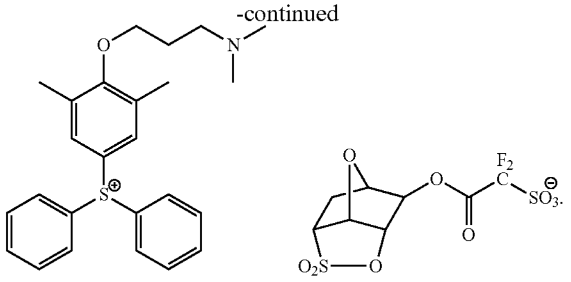
* * * * *

UNITED STATES PATENT AND TRADEMARK OFFICE

CERTIFICATE OF CORRECTION

PATENT NO. : 8,703,387 B2
APPLICATION NO. : 13/478390
DATED : April 22, 2014
INVENTOR(S) : Akiya Kawaue et al.

It is certified that error appears in the above-identified patent and that said Letters Patent is hereby corrected as shown below:

In the Specification

At Column 6, Line 20, Change "sulfoneamide" to --sulfonamide--.

At Column 45, Line 38, Change "(a1-0-01)" to --(a1-1-01)--.

At Column 45, Line 41 (Approx.), Change "(a1-0-02)" to --(a1-1-02)--.

At Column 46, Line 19, Change "(a1-0-01)," to --(a1-1-01),--.

At Column 46, Line 24 (Approx.), Change "(a1-0-02)," to --(a1-1-02),--.

At Column 50, Line 51, After "-O-CH2-," insert -- -CH2-O-CH2-,--.

At Column 56, Line 42, Change "(a1-0-01)" to --(a2-0-1)--.

At Column 59, Line 12 (Approx.), Change "propionolatone," to --propiolactone,--.

At Column 60, Line 46, Change "group" to --group.--.

At Column 89, Line 46 (Approx.), Change "(x-4-1)" to --(x4-1)--.

At Column 97, Line 30 (Approx.), Change "(I1-1-19)" to --(I-1-19)--.

At Column 99, Line 27, Change "R19" to --R10--.

At Column 100, Line 25, After "of" insert --Y11--.

At Column 103, Line 56, Change "anlkylene" to --alkylene--.

Signed and Sealed this
Ninth Day of December, 2014

Michelle K. Lee
*Deputy Director of the United States Patent and Trademark Office*

At Column 109, Line 60-65, Change “ 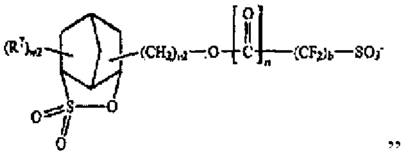 ” to

-- 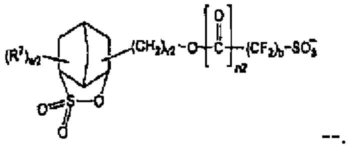 --.

At Column 113, Line 8, Change “phenantryl” to --phenanthryl--.

At Column 119, Line 53, Change “$CH^2$” to --$CH_2$--.

At Column 124, Line 7, Change “Z” to --Z- --.

At Column 124, Line 29, Change “(1-3),” to --(i-3),--.

At Column 129, Line 14, Change “at” to --as--.

At Column 143, Line 4, (Compound (B) – 13), Change “suttone),” to --sultone),--.

At Column 161, Line 4, (Compound (B) – 37), Change “oxosultane),” to --oxosultone),--.

At Column 174, Line 16, Before “line” delete “119”.

In the Claims

At Column 177, Line 65, In Claim 6, change “(B 1)” to --(B1)--.